(12) United States Patent
Potyrailo et al.

(10) Patent No.: US 11,391,716 B2
(45) Date of Patent: Jul. 19, 2022

(54) RESONANT SENSOR PROBE ASSEMBLY

(71) Applicant: Transportation IP Holdings, LLC, Norwalk, CT (US)

(72) Inventors: Radislav Alexandrovich Potyrailo, Niskayuna, NY (US); Craig Mack, Lisburn (GB); Christopher Calvert, Belfast (GB); Brian Scherer, Niskayuna, NY (US); James Schreiner, Erie, PA (US); Najeeb M Kuzhiyil, Lawrence Park, PA (US); Subramani Adhiachari, Bangalore (IN); Partho Kayal, Bangalore (IN); Milan Karunaratne, Lawrence Park, PA (US); Nicholas E. Roddy, Schenectady, NY (US); Janaki Gadiyaram, Bangalore (IN); Steven Go, Schenectady, NY (US); Victor Manuel Salazar, Albany, NY (US)

(73) Assignee: TRANSPORTATION IP HOLDINGS, LLC, Norwalk, CT (US)

( * ) Notice: Subject to any disclaimer, the term of this patent is extended or adjusted under 35 U.S.C. 154(b) by 0 days.

(21) Appl. No.: 17/224,969

(22) Filed: Apr. 7, 2021

(65) Prior Publication Data
US 2021/0270798 A1 Sep. 2, 2021

Related U.S. Application Data

(63) Continuation of application No. 16/146,322, filed on Sep. 28, 2018, now Pat. No. 10,996,210.

(60) Provisional application No. 62/612,855, filed on Jan. 2, 2018.

(51) Int. Cl.
| | |
|---|---|
| G01M 15/09 | (2006.01) |
| G01N 33/28 | (2006.01) |
| B61L 3/00 | (2006.01) |
| G01N 27/22 | (2006.01) |
| G01N 27/02 | (2006.01) |

(52) U.S. Cl.
CPC .......... *G01N 33/2888* (2013.01); *B61L 3/002* (2013.01); *G01M 15/09* (2013.01); *G01N 27/026* (2013.01); *G01N 27/221* (2013.01); *G01N 33/28* (2013.01)

(58) Field of Classification Search
CPC .............................. G01M 15/09; G01N 33/28
See application file for complete search history.

(56) References Cited

U.S. PATENT DOCUMENTS

| | | | |
|---|---|---|---|
| 7,043,402 B2* | 5/2006 | Phillips | G01N 27/02 324/600 |
| 10,261,036 B2* | 4/2019 | Potyrailo | G01N 27/026 |
| 2010/0188111 A1* | 7/2010 | Fougere | G01N 33/2823 324/698 |

(Continued)

*Primary Examiner* — Jamel E Williams
(74) *Attorney, Agent, or Firm* — Will Breeze; The Small Patent Law Group LLC

(57) ABSTRACT

A resonant sensor probe assembly includes a substrate formed from one or more dielectric materials and free-standing electrodes coupled with the substrate. The free-standing electrodes are configured to be placed into the fluid and to generate an electric field between the free-standing electrodes. A controller measures an impedance response of the sensor to the fluid between the electrodes to determine an aging effect of the sensor.

20 Claims, 34 Drawing Sheets

(56) References Cited

U.S. PATENT DOCUMENTS

| | | | |
|---|---|---|---|
| 2014/0002111 A1* | 1/2014 | Potyrailo | G01N 27/026 324/655 |
| 2015/0115983 A1* | 4/2015 | Potyrailo | G01N 27/026 324/693 |
| 2017/0081997 A1* | 3/2017 | Potyrailo | G01N 27/026 |
| 2017/0138922 A1* | 5/2017 | Potyrailo | G01M 13/021 |
| 2017/0363555 A1* | 12/2017 | Potyrailo | G01N 27/026 |
| 2020/0408733 A1* | 12/2020 | Haye | F01D 25/20 |

* cited by examiner

RESONANT SENSOR PROBE ASSEMBLY

CROSS-REFERENCE TO RELATED APPLICATIONS

This application is a continuation of U.S. patent application Ser. No. 16/146,322, filed 28 Sep. 2018, which claims priority to U.S. Provisional Application No. 62/612,855, filed 2 Jan. 2018. The entire disclosures of these applications are incorporated herein by reference.

BACKGROUND

Technical Field

Embodiments of the subject matter disclosed herein generally relate to sensor probe assemblies that monitor the health of oil in various environments, such as when oil is utilized as a lubricant in engines, gearboxes, or generators, or as an electrical isolator in electrical transformers. Not all embodiments of the subject matter described herein, however, is limited to monitoring the health of oil in engines, gearboxes, or transformers.

Discussion of Art

Real time monitoring of health of engine or gearbox lubricating oil can be important for various applications such as vehicles (e.g., locomotives, marine vessels, automobiles, and others), and wind turbine gearboxes where early detection of engine or gearbox lubricating oil degradation, oil aging, and/or leaks of other fluids into the oil. Some known sensors measure various aspects of oil health include mechanical resonating sensors (such as tuning forks and acoustic wave devices), capacitive sensors, conductometric sensors, sensor arrays, dielectric spectroscopy sensors, and complex permittivity sensors. These sensors have several limitations, such as low sensitivity and little to no resolution between different effects on oil. These limitations can prevent use of the sensors for early diagnosis of leaks of process fluids into engine oil.

Dissolved gas analysis (DGA) of isolating transformer oil is used for diagnostic measurements of transformer health and prognosis. Additionally, monitoring substation transformer health via DGA of the insulating oil is important for predicting potentially catastrophic faults and failures. Concentrations of dissolved gases in oil are measured at the part-per-million (ppm) level, with target gases such as hydrogen $H_2$, carbon monoxide CO, carbon dioxide $CO_2$, methane $CH_4$, acetylene $C_2H_2$, ethylene $C_2H_4$, ethane $C_2H_6$, or the like. Current DGA systems use a method to extract gas from oil (e.g. headspace or membrane) and then measure in the gas phase to infer the ppm concentration in oil. Examples of existing technologies for the gas determination and sensing are gas chromatography and infrared spectroscopy. To selectively measure the required fault gases, the extraction and gas sensor components can be expensive and complex, have many moving parts, can have a wide range of failure modes or performance challenges, or the like. If conventional sensors are used in DGA systems, these sensors exhibit drift over time. Such drift prevents the use of these sensors for accurate DGA determinations in long term applications.

BRIEF DESCRIPTION

In one embodiment, a system is provided that includes a resonant sensor probe assembly coupled to a reservoir. The sensor probe assembly includes a substrate formed from one or more dielectric materials and free-standing electrodes coupled with the substrate. The free-standing electrodes are configured to be placed into a fluid, to generate an electric field between the free-standing electrodes, and to measure an impedance response of the sensor to the fluid between the electrodes.

In one embodiment, a method for monitoring a health of equipment lubricant is provided. The method includes monitoring previous operational conditions of a powered system that operates using fuel and a lubricant, identifying one or more of an impurity content of the fuel supplied to the powered system or an elapsed time since a previous addition of additional lubricant to the lubricant in the powered system, and determining whether a change of the lubricant is required prior to continued operation of the powered system based on the previous operational conditions and the one or more of the impurity content of the fuel or the elapsed time since the previous addition of the additional lubricant to the lubricant in the powered system.

In one embodiment, a system includes a reservoir configured to hold a fluid and a sensor probe assembly having a substrate formed from one or more dielectric materials and free-standing electrodes coupled with the substrate and configured to be placed into the fluid. The sensor probe assembly is configured to generate an electric field between the electrodes, and to measure an electric response of the sensor to the fluid between the electrodes. The system also includes a controller configured to determine the electric response of the sensor while the sensor is not generating the electric field between the electrodes and to determine the electric response of the sensor while the sensor is generating the electric field between the electrodes. The controller also is configured to determine an aging effect of the sensor based on the electric response that is measured while the sensor is not generating the electric field between the electrodes. The controller is configured to correct the electric response of the sensor that is measured while the sensor is generating the electric field between the electrodes using the aging effect that is determined.

In one embodiment, a resonant sensor probe assembly includes a substrate formed from one or more dielectric materials and free-standing electrodes coupled with the substrate. The free-standing electrodes are configured to be placed into a fluid under examination, to generate an electric field between and in proximity to the free-standing electrodes, and to measure an impedance response of the sensor to the fluid between and in proximity to the electrodes. The fluid can be a gas or a liquid.

In one embodiment, a method includes monitoring previous operational conditions of an engine that operates using fuel and a lubricant, identifying one or more of an impurity content of the fuel supplied to the engine or an elapsed time since a previous addition of additional lubricant to the lubricant in the engine, and determining whether a change of the lubricant is required prior to continued operation of the engine based on the previous operational conditions and the one or more of the impurity content of the fuel or the elapsed time since the previous addition of the additional lubricant to the lubricant in the engine.

In one embodiment, a method includes measuring an electrical response of a sensing material in a gas sensor probe assembly while the gas sensor probe assembly is in an OFF state, determining an aging effect of the gas sensor probe assembly based on the electrical response of the sensing material in the gas sensor probe assembly while the gas sensor probe assembly is in the OFF state, measuring an electrical response of the sensing material in the gas sensor probe assembly while the sensing material is exposed to a fluid under examination and while the gas sensor probe assembly is in an ON state, and correcting the electrical response of the sensing material in the gas sensor probe assembly that is measured while the gas sensor probe assembly is in the ON state using the aging effect of the gas sensor probe assembly.

BRIEF DESCRIPTION OF THE DRAWINGS

The presently described subject matter will be better understood from reading the following description of non-limiting embodiments, with reference to the attached drawings, wherein below.

DETAILED DESCRIPTION

Figure 1:
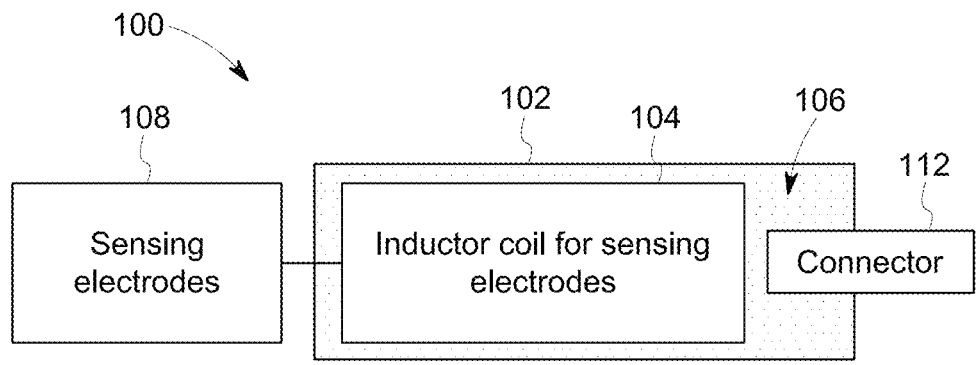
FIG. 1 illustrates a top view of one embodiment of a sensor probe assembly.

Some oil sensors are based on an inductor-capacitor-resistor (LCR) resonator structure that monitors aspects of oil health, such as levels of oil degradation and levels of external contaminants into oil. The LCR resonator operates in a multivariable mode where multiple outputs from the resonator are measured and used to detect independent changes in the oil health due to the leaks of water and fuel into the oil, and oil aging.

These types of sensors can involve a sensor probe comprised of two distinct components such as a sensing substrate onto which an electrode structure was deposited. The sensor probe is a region of the sensor that is in operational contact with the measured industrial fluid (e.g., oil). Other portions of the sensor (such as sensor housing, transformer, electronics, electrical connectors, etc.) are not in operational contact with the measured industrial fluid. The sensing substrate is an inert material that allows the sensing electrodes to be presented to the fluid.

The sensing electrodes may be deposited only on one side of the substrate. This type of design has significant limitations. First, the need for a substrate may not allow the entire surface of the electrodes to be in contact with the fluid under examination. Second, the substrate material can add a significant parasitic capacitance that reduces the sensitivity of the response of the sensor. Third, the substrate material can add a significant parasitic capacitance that reduces the selectivity of the response of the sensor to different constituents in the fluid under examination.

In one embodiment of the inventive subject matter described herein, a sensor probe assembly for monitoring of fluid (e.g., a gas or liquid, such as a lubricant) health and/or other industrial fluid health has significant structural and manufacturing differences as compared to known sensor probes, and has a significant improvement in sensor performance such as sensor sensitivity and sensor selectivity as compared to the known sensor probes. One structural difference in the design of the sensor probe assemblies described herein is in the design of electrodes that does not require a sensor substrate. These free-standing electrodes have a larger area that is in contact with the oil or fluid when compared to the electrodes of the same size of previous sensor probes that were deposited or otherwise mounted on substrates. The larger area can include a material that is sensitive to the presence of impurities in a fluid under examination. Examples of such materials include metal oxide semiconductor materials, such as tin oxide (SnO2), inorganic sorbing materials such as porous alumina, porous silicon, or polymeric sorbing materials such as poly[4,5-difluoro-2,2-bis(trifluoromethyl)-1,3-dioxole-co-tetrafluoroethylene] (Teflon AF) or poly[4,4'-oxydiphenylene-pyromellitimide] (Kapton), or another sensing material. These free-standing electrodes with or without sensing material are a part of a resonant circuit of the sensor probe. Another structural difference in the design of the sensor probe assembly as compared to the known sensors is that the electrodes have openings for an improved flow path of the measured oil or fluid across the electrodes. Another structural difference in the design of the sensor probe assembly as compared to the known sensors is that the free-standing electrodes simultaneously serve as an inductor of the resonant sensor.

The sensor probe assembly can be manufactured using additive manufacturing (e.g., three-dimensional printing) and electrical discharge machining to produce the free-standing electrodes. The resonant components of a circuit of the sensor probe assembly also can be produced using additive manufacturing and electrical discharge machining. Electrical discharge machining is also known as spark machining, spark eroding, burning, die sinking, wire burning, or wire erosion. This type of machining creates a desired shape using electrical discharges, such as sparks.

Figure 2:
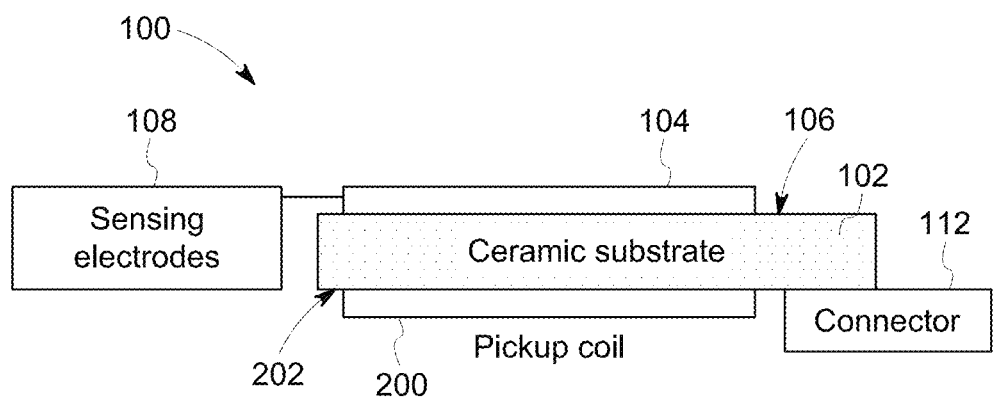
FIG. 2 illustrates a side view of the sensor probe assembly shown in FIG. 1.

FIG. 1 illustrates a top view of one embodiment of a sensor probe assembly 100. FIG. 2 illustrates a side view of the sensor probe assembly 100 shown in FIG. 1. The sensor probe assembly 100 can be included in a measurement system that measures the presence and/or amounts of one or more impurities or other compounds in a fluid of interest, such as oil or another lubricant. The sensor probe assembly 100 includes a substrate 102 formed from a non-conductive material, such as one or more ceramic materials. The substrate 102 can have a planar shape as shown in FIG. 2. A conductive inductor coil 104 is mounted on one side 106 of the substrate 102 and is conductively coupled with one or more free-standing conductive electrodes 108. As shown in FIGS. 1 and 2, the electrodes 108 are not mounted on the substrate 102 in that the electrodes 108 are not directly coupled with, do not directly engage, and do not abut any part or surface of the substrate 102. Moreover, the electrodes 108 are not above or below a footprint of the substrate 102, which is defined by the surface area of the side 106 of the substrate 102 that extends upward and downward in the view of FIG. 2. A conductive pickup coil 200 is coupled with the substrate 102 on a side 202 of the substrate 102 that is opposite of the side 106 to which the inductor coil 104 is mounted. The inductor coil 104 is conductively coupled with one or more electronic connectors 112.

In operation, the sensor probe assembly 100 examines a fluid sample in contact with the electrodes 108 for detection of one or more analytes of interest. The sensor probe assembly 100 may detect characteristics or properties of the fluid via a resonant or non-resonant impedance spectral response of the material on the electrodes 108 (not shown). One or more of the inductor-capacitor-resistor resonant circuits (LCR resonators) that are at least partially formed by the electrodes 108 and the inductor coil 104 may measure the resonant impedance spectral response of a fluid under inspection. A non-resonant impedance spectral response is measured when the circuit does not contain an inductor. The resonant or non-resonant impedance spectrum of the electrodes 108 in proximity to a fluid sample varies based on sample composition and/or components. The measured resonant or non-resonant impedance values Z' (which may be the real part of resonant or non-resonant impedance, Zre) and Z" (which may be the imaginary part of resonant or non-resonant impedance, Zim) reflect the response of the electrodes 108 to the fluid. Optionally, an electrical field may be applied to a sensing material or film of the sensor probe assembly 100 via the electrodes 108. The distance between the electrodes 108, may define the magnitude of the electric field. The electrodes 108 may be in direct contact with the measured fluid. Alternatively, the electrodes 108 may be in direct contact with the sensing material. For example, the sensing element may be a combination of a sensing region and associated circuits and/or the sensing region may be coated with the sensing material. The sensing material may be semiconductor material or metal oxide semiconductor material. The impedance values measured by the electrodes 108 and/or coil 104 can be inductively communicated through or across the substrate 102 to the pickup coil 200, and can then be conducted to the connector 112 to another system (e.g., data acquisition circuitry).

Data from the sensor probe assembly 100 may be acquired via the data acquisition circuitry which is connected with the assembly 100 via the connector 112. The data acquisition circuitry can be connected with a controller or computer workstation where additional processing and analysis of the sensor data may be performed. The data can be indicative of the health of the fluid, the presence of contaminants within the fluid, and/or the age of the fluid.

Figure 3:
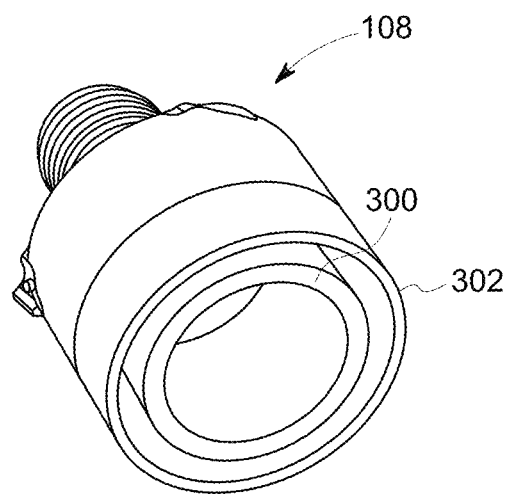
FIG. 3 illustrates a perspective view of an alternative embodiment of electrodes of the sensor probe assembly shown in FIGS. 1 and 2.
Figure 4:
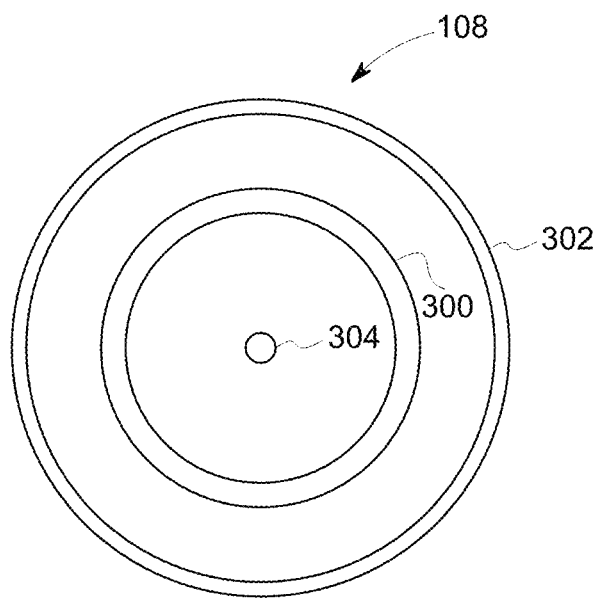
FIG. 4 illustrates an end view of the electrodes shown in FIG. 3.

FIG. 3 illustrates a perspective view of an alternative embodiment of the electrodes 108 of the sensor probe assembly 100 shown in FIGS. 1 and 2. FIG. 4 illustrates an end view of the electrodes 108 shown in FIG. 3. In the illustrated embodiment, the electrodes 108 are arranged as coaxial tubes or circles 300, 302 that extend around and share a common center axis 304. The electrodes 108 are shaped as opposing plates that receive the fluid between the plates in FIGS. 1 and 2, but are tubes or circles in FIGS. 3 and 4. The electrode tubes or circles 300, 302 can be separated from each other by a radial gap so that the electrode tubes or circles 300, 302 are not conductively coupled with each other off of or outside of the substrate 102. The electrode tubes or circles 300, 302 can be placed into the fluid under examination so that at least some of the fluid enters into the gap between the electrode tubes or circles 300, 302. Although not shown in FIGS. 3 and 4, the electrodes can have sensing material (e.g., a metal oxide semiconductor) deposited thereon that responds to the presence of one or more impurities of interest and an electric field generated by the electrodes.

Figure 5:
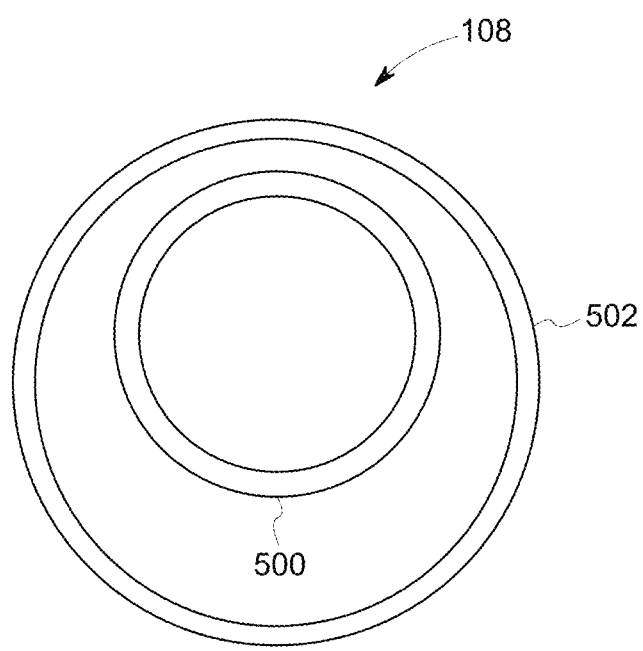
FIG. 5 illustrates an end view of an alternative embodiment of the electrodes of the sensor probe assembly shown in FIGS. 1 and 2.

FIG. 5 illustrates an end view of an alternative embodiment of the electrodes 108 of the sensor probe assembly 100 shown in FIGS. 1 and 2. In the illustrated embodiment, the electrodes 108 are arranged as non-coaxial tubes or circles 500, 502. The tube or circle 502 can extend around the tube or circle 400 without the tubes or circles 500, 502 having the same center axis. The electrode tubes or circles 500, 502 can be separated from each other by a gap so that the electrode tubes or circles 500, 502 are not conductively coupled with each other off of or outside of the substrate 102. The electrode tubes or circles 500, 502 can be placed into the fluid under examination so that at least some of the fluid enters into the gap between the electrode tubes or circles 500, 502. Although not shown in FIG. 5, the electrodes can have sensing material (e.g., a metal oxide semiconductor) deposited thereon that responds to the presence of one or more impurities of interest and an electric field generated by the electrodes.

Figure 6:
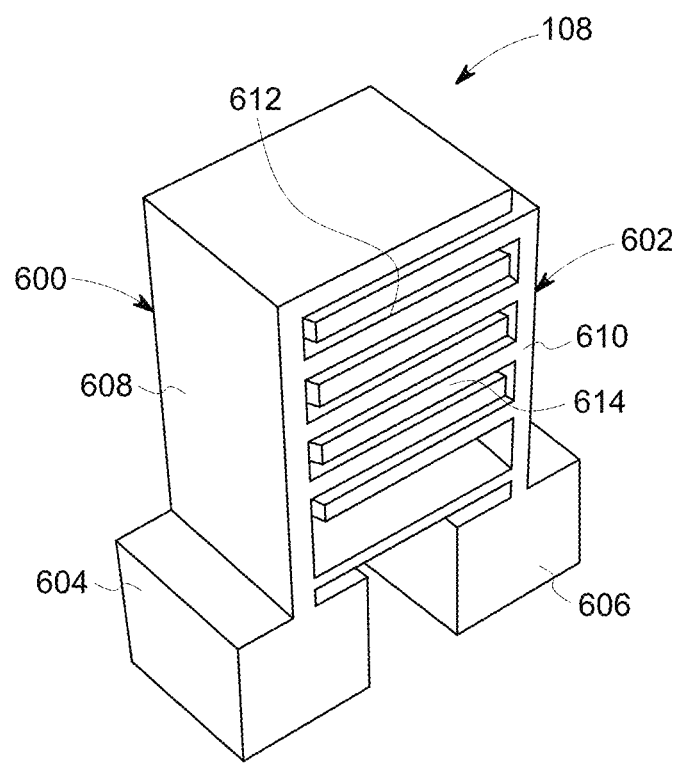
FIG. 6 illustrates a perspective view of another alternative embodiment of the electrodes of the sensor probe assembly shown in FIGS. 1 and 2.
Figure 7:
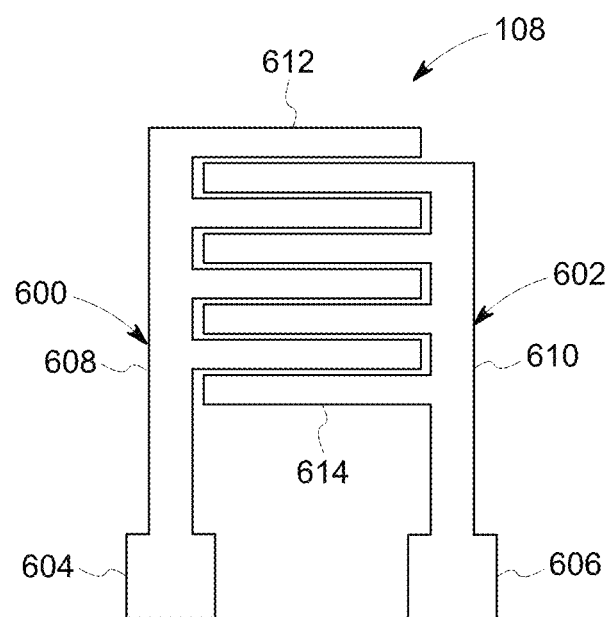
FIG. 7 illustrates a side view of embodiment of the electrodes shown in FIG. 6.
Figure 8:
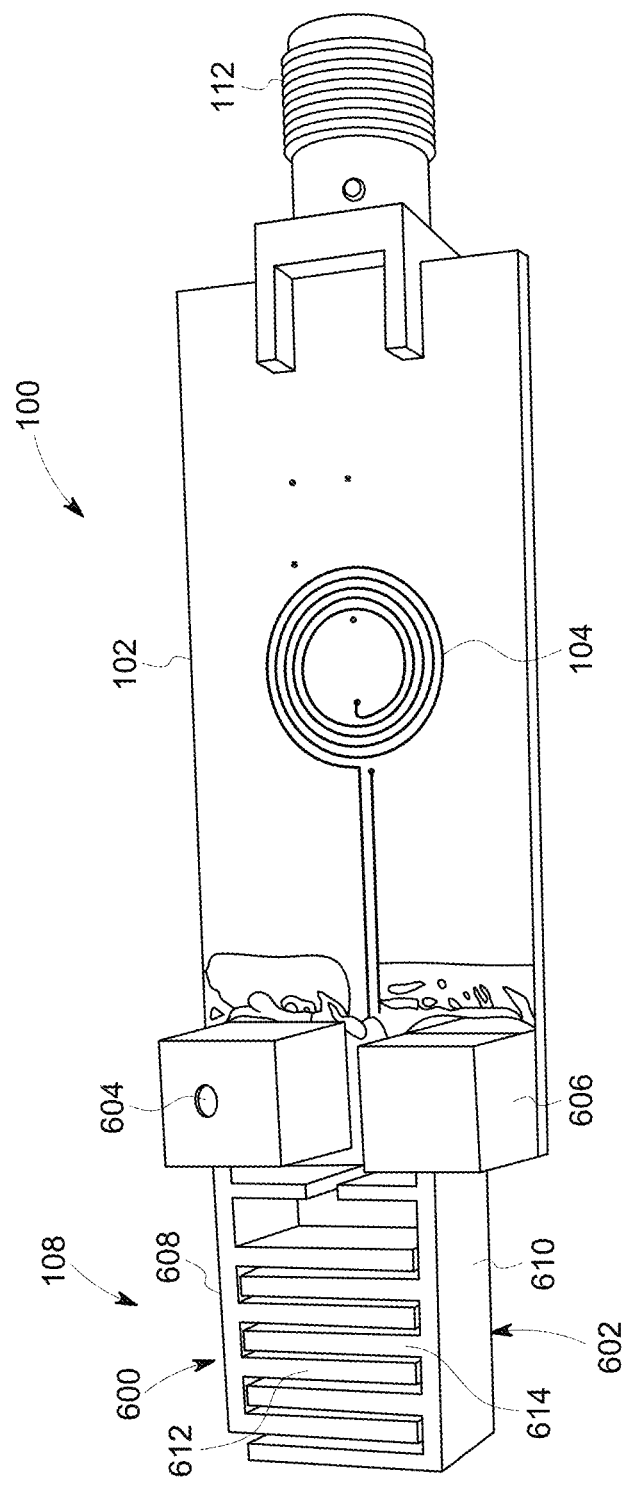
FIG. 8 illustrates the sensor probe assembly shown in FIG. 1 with the embodiment of the electrodes shown in FIGS. 6 and 7.

FIG. 6 illustrates a perspective view of another alternative embodiment of the electrodes 108 of the sensor probe assembly 100 shown in FIGS. 1 and 2. FIG. 7 illustrates a side view of embodiment of the electrodes 108 shown in FIG. 6. FIG. 8 illustrates the sensor probe assembly 100 shown in FIG. 1 with the embodiment of the electrodes 108 shown in FIGS. 6 and 7. In the illustrated embodiment, the electrodes 108 are arranged as interdigital electrodes 600, 602. The interdigital electrodes 600, 602 extend from different connecting ends 604, 606 that are separately coupled with the inductor coil 104 shown in FIG. 1. The connecting ends 604, 606 are part of elongated connecting bars 608, 610 of the electrodes 600, 602. The connecting bars 608, 610 are oriented parallel to each other. Although not shown in FIGS. 6 and 7, the electrodes can have sensing material (e.g., a metal oxide semiconductor, porous alumina oxide, porous silicon, polymer, zeolite, metal organic framework, or another material) deposited thereon that responds to the presence of one or more impurities of interest and an electric field generated by the electrodes.

The electrodes 600, 602 include several elongated fingers 612, 614 that are coupled with a different one of the connecting bars 608, 610, and that extend toward, but are not coupled with, the other connecting bar 608. For example, the fingers 612 are coupled with the connecting bar 608 and extend toward, but are not coupled with and do not engage, the other connecting bar 610. Similarly, the fingers 614 are coupled with the connecting bar 610 and extend toward, but are not coupled with and do not engage, the other connecting bar 608.

The electrode fingers 612, 614 are oriented parallel to each other such that the electrode fingers 612 are spaced apart from the electrode fingers 614 in directions that are perpendicular to the directions in which the fingers 612, 614 are elongated and in directions that are parallel to the directions in which the connecting bars 608, 610 are elongated. The electrode fingers 612, 614 can be placed into the fluid under examination so that at least some of the fluid enters into the gaps between the electrode fingers 612, 614.

Figure 9:
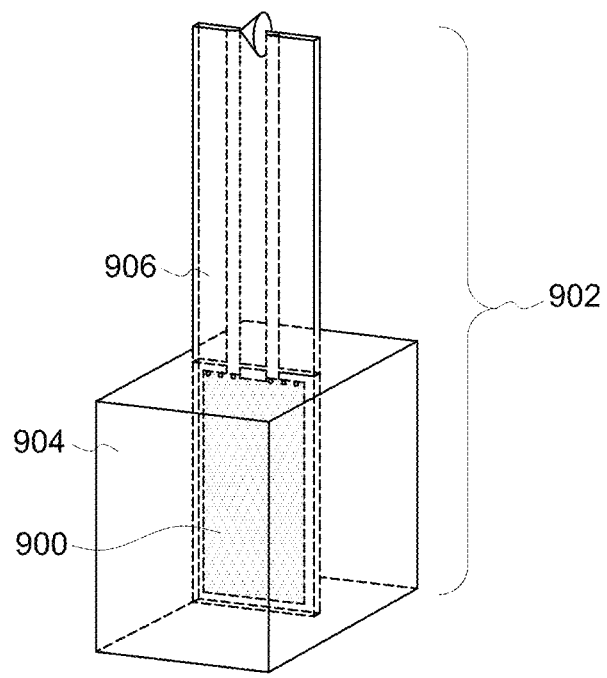
FIG. 9 illustrates partial submersion of electrodes of a known resonant sensor probe assembly into a fluid under examination.
Figure 10:
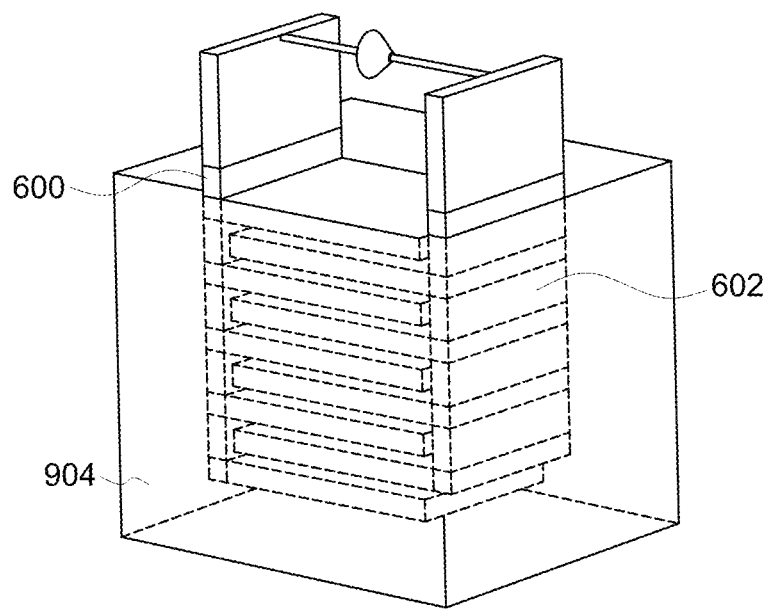
FIG. 10 illustrates partial submersion of the electrodes of the sensor probe assembly shown in FIGS. 6 through 8 into the fluid under examination.

Comparisons of sensitivities was done of a known resonant sensor probe assembly that use electrodes deposited on a substrate and one embodiment of the sensor probe assembly 100 having interdigital free-standing electrodes 600, 602. FIG. 9 illustrates submersion of electrodes 900 of a known resonant sensor probe assembly 902 into a fluid under examination 904 and FIG. 10 illustrates submersion of the electrodes 600, 602 of the sensor probe assembly 100 shown in FIGS. 6 through 8 into the fluid under examination 904. The known probe assembly 902 shown in FIG. 9 includes the electrodes 900 being mounted or disposed upon a substrate 906. In contrast, the electrodes 600, 602 of the probe assembly 100 shown in FIG. 10 are free-standing and are not mounted to any substrate.

As shown in the perspective view of the electrodes 600, 602 shown in FIGS. 6 and 10, the electrodes 600, 602 are larger in three orthogonal directions (e.g., the x-, y-, and z-axes of the Cartesian coordinate system) than the electrodes 900 that are mounted on the substrate 906. The electrodes 900 have a more planar shape as these electrodes 900 are deposited onto the substrate 906 in a thin layer. The electrodes 600, 602 are larger in three dimensions than the electrodes 900.

Figure 11:
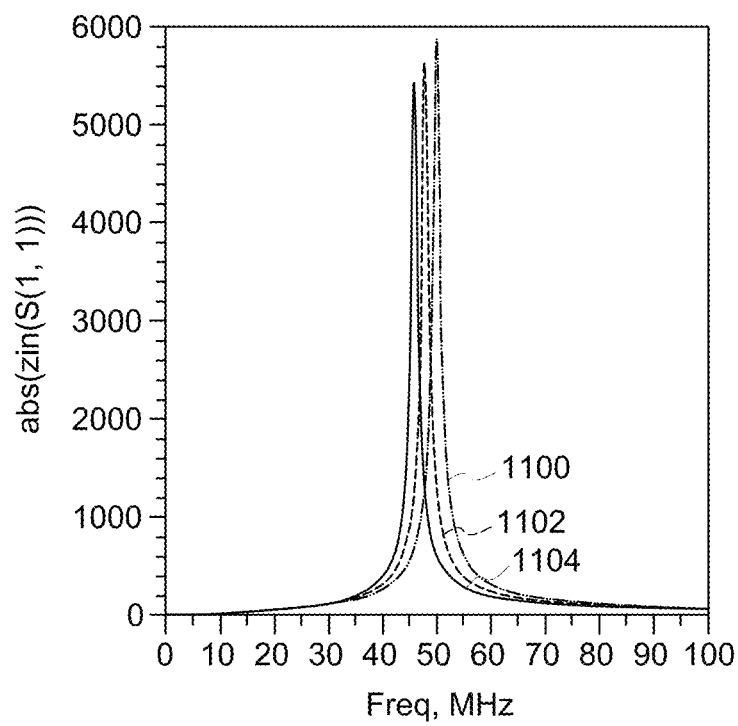
FIG. 11 illustrates resonant spectral responses of the sensor probe assembly with the free-standing electrodes in contact with oil having dielectric constants of 2.1, 2.3, and 2.5, respectively, according to one example.
Figure 12:
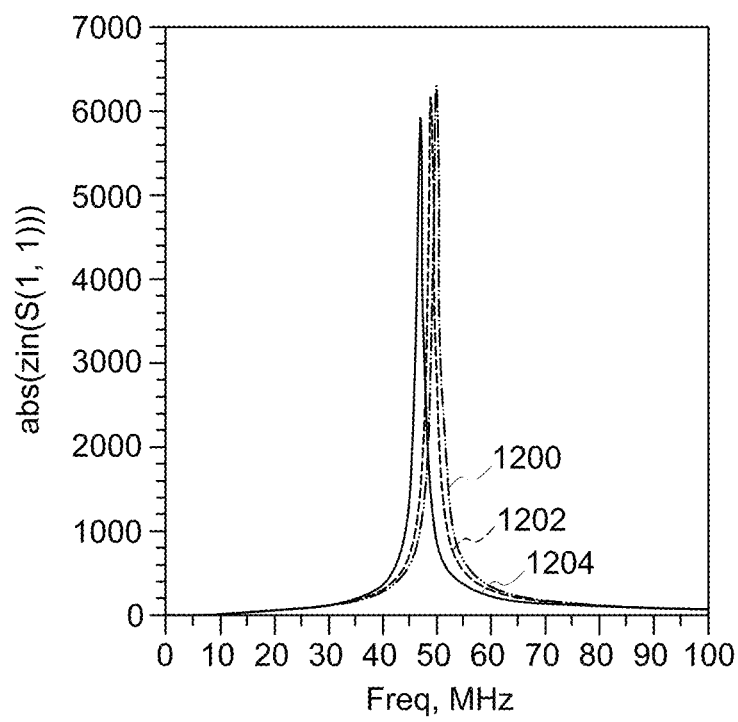
FIG. 12 illustrates resonant spectral responses of the sensor probe assembly with the non-free-standing electrodes deposited onto the substrate having a dielectric constant of one according to a first example.
Figure 13:
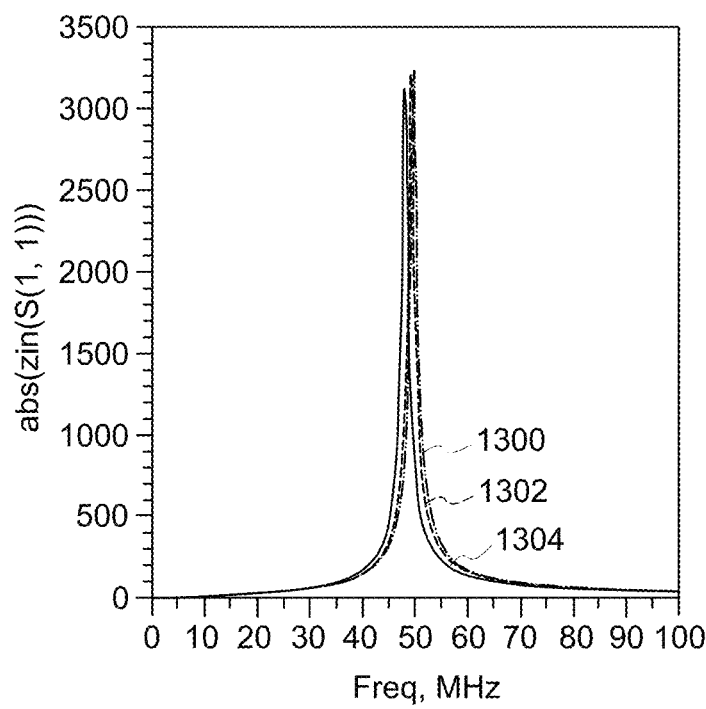
FIG. 13 illustrates resonant spectral responses of the sensor probe assembly with the non-free-standing electrodes deposited onto the substrate having a dielectric constant of 4.5 (e.g., FR4) according to a first example.
Figure 14:
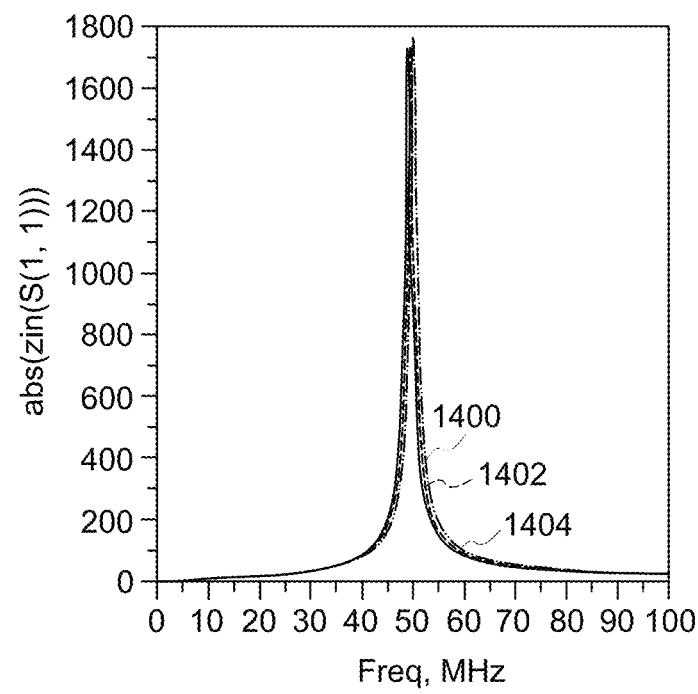
FIG. 14 illustrates resonant spectral responses of the sensor probe assembly with the non-free-standing electrodes deposited onto the substrate having a dielectric constant of 9.1 (e.g., alumina) according to a first example.

Three-dimensional electromagnetic modeling was used to determine the effects of the changes of the dielectric properties of the fluid 904 surrounding sensing regions of the probe assemblies 902, 100 that include the electrodes 900, 600, 602 on the spectral responses of the two different types of the resonant sensor probe assemblies 902, 100. FIG. 11 illustrates resonant spectral responses 1100, 1102, 1104 of the sensor probe assembly 100 with the free-standing electrodes 600, 602 in contact with oil having dielectric constants of 2.1, 2.3, and 2.5, respectively, according to one example. FIG. 12 illustrates resonant spectral responses 1200, 1202, 1204 of the sensor probe assembly 902 with the electrodes 900 deposited onto the substrate 906 having a dielectric constant of one according to a first example. FIG. 13 illustrates resonant spectral responses 1300, 1302, 1304 of the sensor probe assembly 902 with the electrodes 900 deposited onto the substrate 906 having a dielectric constant of 4.5 (e.g., FR4) according to a first example. FIG. 14 illustrates resonant spectral responses 1400, 1402, 1404 of the sensor probe assembly 902 with the electrodes 900 deposited onto the substrate 906 having a dielectric constant of 9.1 (e.g., alumina) according to a first example. The spectral responses shown in FIGS. 11 through 14 are shown alongside horizontal axes representative of frequencies and vertical axes representative of magnitudes of the resonant responses of the sensor probe assemblies to the oil.

Figure 15:
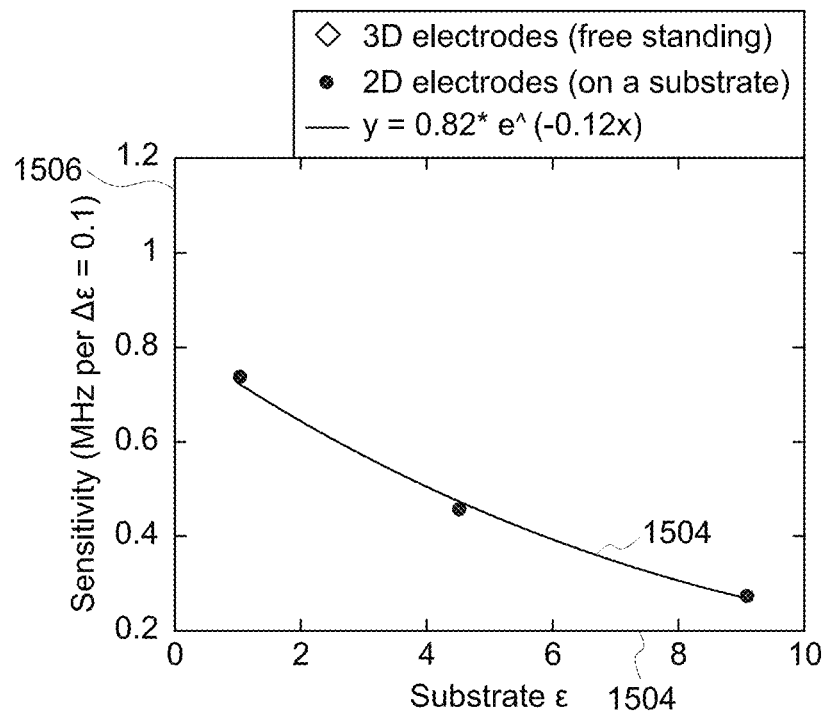
FIG. 15 illustrates a comparison of sensitivities of the sensor probe assemblies associated with the examples of FIGS. 11 through 14 according to one example.

FIG. 15 illustrates a comparison of sensitivities 1500, 1502 of the sensor probe assemblies associated with the examples of FIGS. 11 through 14 according to one example. The sensitivities 1500, 1502 are shown alongside a horizontal axis 1504 representative of the dielectric constants of the surfaces on which the electrodes 600, 602, 900 of the sensor probe assemblies 100, 902 are mounted and a vertical axis 1506 representative of how sensitive the spectral response of the corresponding sensor probe assemblies 100, 902 are to one or more components in the oil. The sensitivity 1500 represents the sensitivity of the probe assembly 100 having the free-standing electrodes 600, 602 while the sensitivities 1502 represent the sensitivities of the probe assemblies 902 having the substrate-mounted electrodes 900 on the substrates with different dielectric constants.

As shown by a comparison of the spectral responses shown in FIGS. 11 through 14, the spectral responses 1100, 1102, 1104 of the sensor probe assembly 100 with the free-standing electrodes 600, 602 demonstrate larger spectral shifts than the spectral responses of the probe assemblies 902 with the electrodes 900 mounted on substrates 906. For example, the peaks of the spectral responses of the sensor probe assembly 100 with the free-standing electrodes 600, 602 are farther apart from each other (along the horizontal axis) than the peaks of the spectral responses of the sensor probe assembly 902 with the substrate-mounted electrodes 900. This indicates that the sensor probe assembly 100 with the free-standing electrodes 600, 602 is more sensitive to, and therefore more accurate in quantifying, the health and/or contents of the oil than the sensor probe assemblies 902 with the substrate-mounted electrodes 900. For example, the spectral responses indicate that the sensitivity of resonant sensor probe assemblies decreases with increases in the dielectric constant of the electrode substrate. Additionally, the sensitivities 1500, 1502 in FIG. 15 show that the sensitivity 1500 of the resonant sensor probe assembly 100 with the free-standing electrodes 600, 602 is significantly higher as compared to that of the sensor probe assembly 902 with electrodes 902 deposited onto a substrate.

When the electrodes are fabricated using additive manufacturing methods, auxiliary sensors may be embedded into the structure of the electrodes. For example, an auxiliary temperature sensor may be built together with the electrodes using 3D printing. The temperature sensor may be used for temperature compensation of the measured variables, for example water content in oil and/or oil aging such as total base number (TBN) or total acid number (TAN). The fabrication method of the electrodes may provide control of the fluid-electrode interface contact angle using electrodes with different morphology, surface finishing and materials with the aim of achieving wetting for a wide range of operating conditions and oils that feature different viscosities and compositions.

When electrodes are fabricated using additive manufacturing methods, the electrodes may be fabricated using more than one material to provide more than one functionality for the sensor. Multi-material 3D printing of electrodes may be done where one or more printed materials are magnetic for detection of metal particles while other printed materials are for detection of other properties such as water content and/or TBN, TAN of the fluid media.

In operation, the electrode structure may be protected with a shield. The shield may be designed to have several functions such as to protect electrodes from mechanical damage, to control flow through the sensing element to allow the sensing electrodes to be fully wetted by the measured fluid, and to control air bubble contact with sensing electrodes, where the openings of the shield may be designed to trap and prevent bubbles to reach the sensing electrodes.

In one embodiment, a resonant sensor probe assembly includes a substrate formed from one or more dielectric materials and free-standing electrodes coupled with the substrate. The free-standing electrodes are configured to be placed into a fluid under examination, to generate an electric field between the free-standing electrodes, and to measure an impedance response of the sensor to the fluid between the electrodes.

Optionally, the free-standing electrodes are not directly mounted on the substrate.

Optionally, the free-standing electrodes are not disposed within a footprint of the substrate.

Optionally, the free-standing electrodes are configured to be placed into the fluid and to measure the impedance response of the sensor to the fluid without the substrate being placed into the fluid.

Optionally, the free-standing electrodes include opposing planar plates positioned to receive at least some of the fluid between the plates.

Optionally, the free-standing electrodes include an inner tube electrode disposed within and spaced apart from an outer tube electrode.

Optionally, the inner and outer tube electrodes are concentric tubes.

Optionally, the free-standing electrodes include opposing supporting bars with elongated, interdigital electrode fingers.

Figure 16:
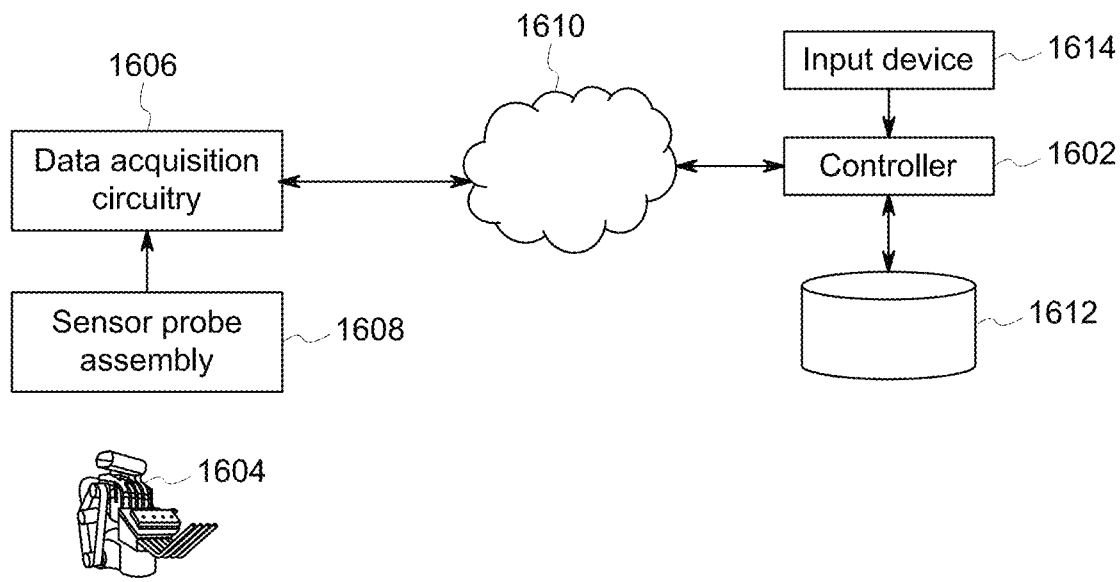
FIG. 16 illustrates one embodiment of a maintenance system.

One example of use of one or more of the sensor probe assemblies described herein (including the assemblies with the free-standing electrodes or the assemblies with the electrodes mounted to substrates) is to measure and quantify the health of engine lubricant, such as oil. FIG. 16 illustrates one embodiment of a maintenance system 1600. The maintenance system 1600 includes a controller 1602 that obtains data from plural different and/or remotely located components and uses the data to create and/or update a model (e.g., digital twin) of equipment 1604. The controller 1602 optionally can use the model to determine when the equipment 1604 (e.g., an engine of a stationary or mobile power-generating machine) needs to have a lubricant (e.g., oil) in the equipment 1604 changed or otherwise replaced. The controller 1602 represents hardware circuitry that includes and/or is coupled with one or more processors (e.g., one or more microprocessors, field-programmable gate arrays, integrated circuits, or the like) that perform the operations described herein.

The controller 1602 obtains measurements of contaminants and other contents of the lubricant from data acquisition circuitry 1606 that receives these measurements from one or more sensor probe assemblies 1608. The sensor probe assemblies 1608 represent one or more of the sensor probe assemblies described herein. The data acquisition circuitry 1606 represents one or more computing hardware systems, such as computers, input devices, or the like, that obtain the measurements of the lubricant as created by the sensor probe assemblies 1608. Because the data acquisition circuitry 1606 and/or sensor probe assemblies 1608 may be remotely located from the controller 1602 (e.g., not in the same room, building, ZIP code, state, or the like), the data acquisition circuitry 1606 can communicate the measurements from the sensor probe assemblies 1608 to the controller 1602 via one or more computerized communication networks 1610, such as one or more public and/or private computer networks.

The controller 1602 is communicatively coupled (e.g., by one or more wired and/or wireless connections) with one or more computer memory devices 1612, such as one or more servers, computer hard drives, optical drives, or the like. The memory devices 1612 can store measurements of the lubricant in the machine 1604 from the sensor probe assemblies 1608, such as the presence of and/or concentrations of one or more contaminants in the oil of the machine 1604 (e.g., water). In one embodiment, the controller 1602 obtains the measurements from the sensor probe assemblies 1608 via the data acquisition circuitry 1606 and stores the measurements in the memory device 1612. Optionally, the data acquisition circuitry 1606 and/or sensor probe assemblies 1608 can send the measurements to the memory device 1612 without the measurements first being sent to or otherwise provided to the controller 1602.

The controller 1602 can examine the measurements provided by the sensor probe assemblies 1608 and use the measurements to predict, self-correct (e.g., using a digital twin of the equipment 1604), and forecast oil change intervals for the equipment 1604. The digital twin of the equipment 1604 is a model of the equipment 1604 that is updated with actual measured characteristics and operational data of the equipment 1604. The digital twin can be used by the controller 1602 to determine an oil change interval for the equipment 1604, which is a prediction of when the oil of the equipment 1604 should be changed based on previous operational data and/or based on hypothetical, planned, or predicted upcoming usage of the equipment 1604.

The oil change interval is a time period between changes of the oil in an engine or a remaining time until an oil change is to occur. The time period may be measured as days, weeks, or months of a calendar; hours and/or minutes of a clock; duty cycles of the engine; or the like. The oil change interval is predicted by the controller 1602 based on a current operational data (e.g., duty cycle) of the engine, as well as oil sample data obtained from one or more of the sensor probe assemblies described herein. This data can include information on which components or impurities are in the oil, as well as the concentration(s) of the impurities. In addition to operational data and oil sample data, fuel sulfur content and an oil top-up date can be obtained as inputs. The fuel sulfur content is a measurement of how much sulfur is in the fuel supplied to the equipment 1604, which can vary widely across different geographical locations. The oil top-up date is the date of the last time that oil was added to the equipment 1604 or a time period since the last time that oil was added to the engine. Optionally, one or more equipment characteristics of the equipment 1604 may be considered, such as whether the engine is a two- or four-stroke engine. As another example, the type of fuel (e.g., gas versus diesel versus a fuel used in hybrid vehicles) can be received as inputs. These inputs can be provided to the controller 1602 by one or more input devices 1614 (and optionally stored in the memory device 1612), or can be provided to and stored in the memory device 1612 from the input device(s) 1614 without first being sent to the controller 1602.

In operation, the controller 1602 obtains information related to the equipment 1604 from the memory device 1612. This information includes operational data, lubricant sample data, and/or lubricant change data. The operational data can include information indicative of usage of the equipment 1604, such as measurements of impurities in oil of the equipment 1604, date of or time since the last oil change, operational cycles of the equipment 1604, locations where the equipment 1604 operated, types of fuel used by the equipment 1604, duration of use of the equipment 1604, temperatures at which the equipment 1604 operated, ambient temperatures in which the equipment 1604 operated, geometrical details or measurements of the equipment 1604 and/or chamber in the equipment 1604 that holds the lubricant, power rating of the equipment 1604, lube system parameters of the equipment 1604 (e.g., lubricant flow rate, lubricant film temperature, combustion characteristics of the equipment 1604, etc.), and the like.

In one embodiment, the operational data obtained by the controller 1602 includes a lubricant top-off date and/or an impurity content of fuel used by the equipment 1604. The top-off date can be the date of or time since lubricant (e.g., oil) was last added to the equipment 1604. The impurity content of the fuel can be the amount of one or more impurities in the fuel consumed by the equipment 1604, such as the sulfur content of fuel supplied to the equipment 1604. Optionally, the operational data obtained by the controller 1602 includes a base oil composition, such as a grade of the lubricant (e.g., different generations of lubricant oils, such as generation 6 or 7).

The lubricant sample data includes measurements of the lubricant in the equipment 1604 obtained by the sensor probe assembly or assemblies 1608. These measurements can include identification of and/or concentrations of one or more impurities in the lubricant, such as water or non-hydrocarbon components. The lubricant change data can include information on when the lubricant was last changed or replaced, as opposed to when lubricant was last added to the equipment 1604. In one embodiment, the measurements obtained from the sensor and/or other systems may be converted from a reference scale (of the sensor or other origin of the measurements) to an absolute scale before providing the measurements to the digital twin. For example, calibration factors used for converting infrared measured soot data may be used. These conversion factors can vary from values of 5 to 60.

Optionally, the measurement of the amount of impurities in the lubricant can include a measurement of one or more additives to the lubricant. For example, base additives can be added to oil to extend the life of the oil. The amount of one or more additives also can be measured and used to determine when a lubricant change is needed. For example, if an impurity measurement trends upward (e.g., soot) and/or an additive measurement trends downward (e.g., a base additive), then a lubricant change may be needed sooner than if the impurity measurement trends downward or remains the same and/or the additive measurement does not decrease.

The controller 1602 can perform an analysis of the obtained information to determine a remaining useful life (RUL) of the lubricant in the equipment 1604 based on the information. The controller 1602 can examine the operational data, lubricant sample data, and/or lubricant change data to determine how much longer the lubricant can be used without being changed or otherwise replaced at a time that is a designated period of time ahead of a scheduled maintenance of the equipment 1604. For example, the equipment 1604 (or a larger powered system that includes the equipment 1604, such as a vehicle) can be scheduled for maintenance or an oil change every three months or three to five thousand miles. At a designated date (e.g., fourteen days ahead of the scheduled oil change or five hundred miles before the next oil change), the controller 1602 can automatically obtain the operational data, lubricant sample data, and/or lubricant change data from the memory device 1612 and determine the remaining useful life of the lubricant based on this information. Depending on how much longer the remaining useful life is, the controller 1602 may direct that the oil change not occur at the next scheduled maintenance, that the next scheduled maintenance be delayed, or that the next scheduled maintenance be performed sooner than the previously scheduled date.

Optionally, the controller 1602 can perform the analysis of the operational data, lubricant sample data, and/or lubricant change data to create and/or update a model (e.g., a digital twin) of the equipment 1604. This model can be used to determine a remaining useful life of the equipment 1604 and/or other systems of the equipment 1604 (e.g., the components that hold and/or direct the flow of lubricant in the equipment 1604). In one embodiment, the digital twin can be used to predict how much longer the equipment 1604 can continue operating with the current lubricant given hypothetical or planned future operating conditions of the equipment 1604. For example, a designated number of upcoming operational cycles of the equipment 1604, one or more designated locations where the equipment 1604 will operate, one or more designated types of fuel that will be used by the equipment 1604, a designated upcoming total duration of use of the equipment 1604, designated temperatures at which the equipment 1604 will operate, designated ambient temperatures in which the equipment 1604 will operate, and the like, can be input into the controller 1602 (e.g., by the input device(s) 1614). Based on the current state or condition of the lubricant (based on the operational data, lubricant sample data, and/or lubricant change data, as described herein), different hypothetical or planned future operating conditions may result in the controller 1602 determining that the lubricant needs to be changed sooner (e.g., than a scheduled maintenance), later (than the scheduled maintenance), that the equipment 1604 cannot safely operate under the designated conditions, or the like. For example, if the operational data, lubricant sample data, and/or lubricant change data indicate a poor state of health of the lubricant, then more upcoming operational cycles, poorer quality fuel (e.g., more impurities), longer upcoming durations of use, hotter operating temperatures, hotter ambient temperatures, and the like, will result in the controller 1602 determining that the equipment 1604 cannot safely operate under the designated upcoming operating conditions without an oil change when compared to fewer upcoming operational cycles, higher quality fuel, shorter upcoming durations of use, cooler operating temperatures, cooler ambient temperatures, and the like.

As the equipment 1604 operates under the planned or other operational conditions, the operating conditions under which the equipment 1604 actually operated can be reported to the controller 1602 and/or stored in the memory device 1612. This information can be used to update the digital twin of the equipment 1604. For example, the total number of operational cycles since a lubricant change, the different types of fuel, the total duration of use since a lubricant change, the operating temperatures and/or ambient temperatures, and the like, can be tracked over time. As the total number of operational cycles since a lubricant change increases, poorer quality fuels are used, the total duration of use since a lubricant change increases, the operating temperatures increase, and/or ambient temperatures increase, the shorter of a time span that the equipment 1604 can operate without an oil change.

Once a lubricant change occurs, however, the controller 1602 can re-set one or more aspects of the digital twin of the equipment 1604. For example, the occurrence of a lubricant change can be input to the controller 1602 via the input device(s) 1614, and the controller 1602 can adjust the digital twin such that data values indicative of previous operating cycles, temperatures, and the like, can be re-set to zero or otherwise changed to indicate that new lubricant is being used in the equipment 1604.

In addition to the operational data, the controller 1602 also uses the sample data to determine whether a change of the lubricant is needed, when a change in the lubricant is needed, and/or whether the equipment 1604 can safely operate under hypothetical or planned upcoming operating conditions without a lubricant change. The sample data can be provided by the sensor probe assemblies 1608 and the controller 1602 can shorten the time span before the next lubricant change and/or determine that the equipment 1604 cannot safely operate without a lubricant change for sample data indicating larger amounts of impurities in the lubricant when compared with sample data indicating smaller or no amounts of impurities in the lubricant.

In one embodiment, the controller 1602 also considers the amount of sulfur in the fuel consumed by the equipment 1604 in determining the remaining useful life of the lubricant in the equipment 1604. For example, one of the inputs considered by the controller 1602 in determining how much longer an engine can continue operating before an oil change is needed can be the amount (e.g., concentration or absolute amount) of sulfur in the fuel supplied to the engine. The controller 1602 can shorten the amount of time or reduce the number of duty cycles that the equipment 1604 can continue operating before a lubricant change is needed for greater amounts of sulfur in the fuel and can lengthen the amount of time or increase the number of duty cycles that the equipment 1604 can continue operating before the lubricant change is needed for lesser amounts of sulfur in the fuel.

The controller 1602 optionally also considers the time or number of duty cycles since a lubricant top-off of the equipment 1604 occurred in determining the remaining useful life of the lubricant in the equipment 1604. For example, one of the inputs considered by the controller 1602 in determining how much longer an engine can continue operating before an oil change is needed can be when the last time oil was added to the engine. The controller 1602 can shorten the amount of time or reduce the number of duty cycles that the equipment 1604 can continue operating before a lubricant change is needed for longer periods of time since lubricant was last added to the equipment 1604 and can lengthen the amount of time or increase the number of duty cycles that the equipment 1604 can continue operating before the lubricant change is needed for shorter time periods since lubricant was last added to the equipment 1604.

Figure 57:
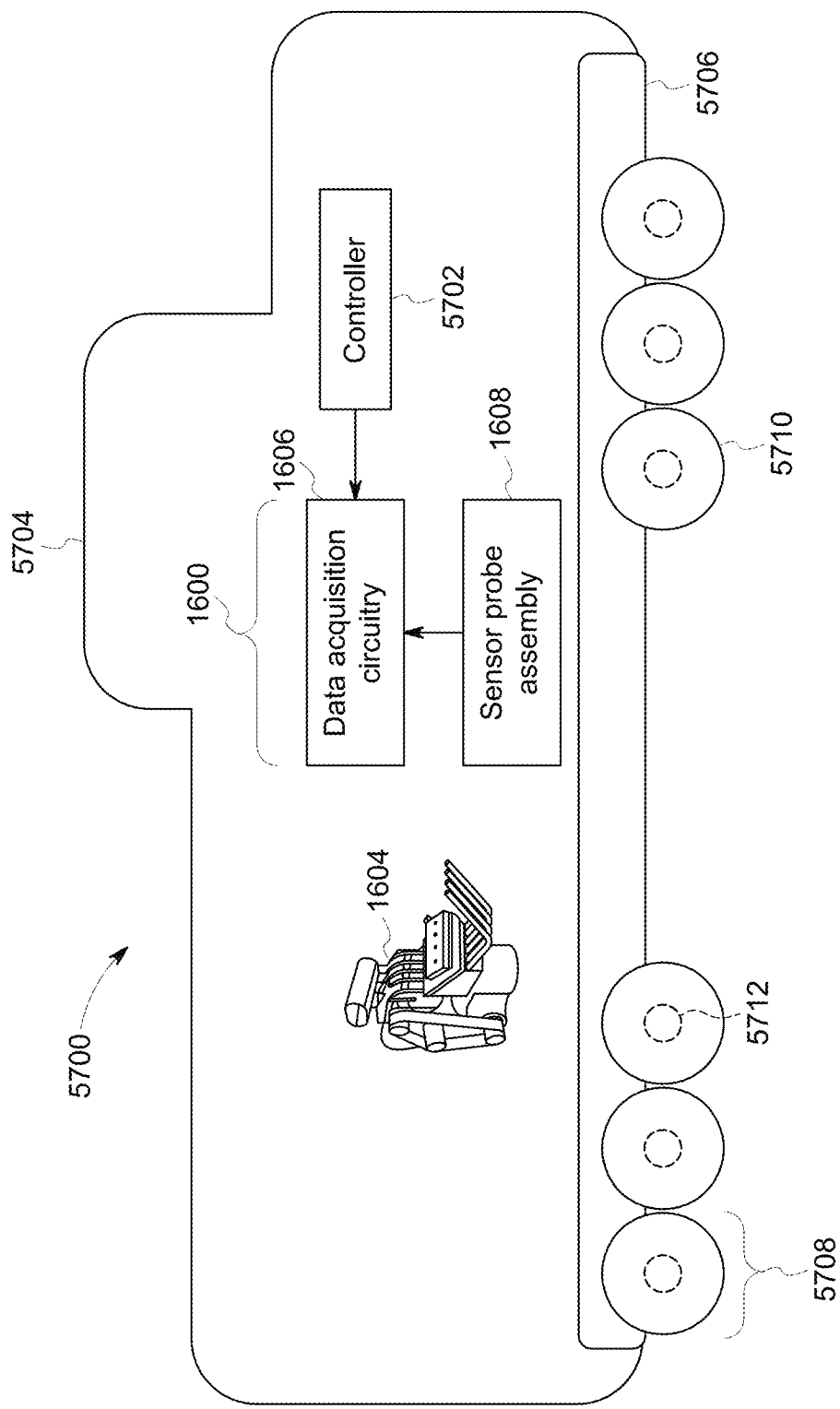
FIG. 57 illustrates another embodiment of the maintenance system used in connection with a powered system.

FIG. 57 illustrates another embodiment of the maintenance system 1600 used in connection with a powered system 5700. The powered system 5700 represents a vehicle 5704, such as a locomotive, that includes a vehicle controller 5702 and the equipment 1604 described above. The vehicle controller 5702 can represent hardware circuitry that includes and/or is connected with one or more processors (e.g., one or more microprocessors, field-programmable gate arrays, integrated circuits, or the like) that control operation of the rail vehicle. For example, the equipment 1604 can represent an engine under control of the vehicle controller 5702 to propel the rail vehicle 5704 along one or more tracks. The rail vehicle 5704 includes a platform 5706, which also can be referred to as a vehicle chassis or body, that supports the maintenance system 1600, the equipment 1604, and other components. The platform 5706 is coupled with multiple wheel-axle sets 5708 that each includes two or more wheels 5710 coupled with an axle 5712. The equipment 1604 can operate to rotate the axles 5712 and wheels 5710 to propel the rail vehicle 5704. Optionally, the rail vehicle 5704 represents another type of vehicle, such as an automobile, a truck, an aircraft (manned or unmanned), marine vessel, mining vehicle, or the like.

The vehicle controller 5702 can be in communication with the data acquisition circuitry 1606 (or the controller 1602, not shown) to determine when the equipment 1604 needs to have a lubricant (e.g., oil) in the equipment 1604 changed or otherwise replaced. The equipment 1604 includes a reservoir that holds the lubricant. The equipment 1604 optionally can represent another reservoir that holds lubricant. The equipment 1604 can be directly or indirectly coupled to the platform 5706.

The controller 5702 obtains measurements of contaminants and other contents of the lubricant from data acquisition circuitry 1606 that receives these measurements from one or more sensor probe assemblies 1608. The controller 5702 can store measurements of the lubricant from the sensor probe assemblies 1608, such as the presence of and/or concentrations of one or more contaminants in the oil of the equipment 1604 (e.g., water). In one embodiment, the controller 5702 obtains the measurements from the sensor probe assemblies 1608 via the data acquisition circuitry 1606 and stores the measurements in a memory device, such as the memory device 1612 shown in FIG. 16.

The controller 5702 can examine the measurements provided by the sensor probe assemblies 1608 and use the measurements to predict, self-correct, and forecast oil change intervals for the equipment 1604. The oil change interval can be predicted by the controller 5702 based on a current operational data (e.g., duty cycle) of the equipment 1604, as well as oil sample data obtained from one or more of the sensor probe assemblies 1608 described herein. This data can include information on which components or impurities are in the oil, as well as the concentration(s) of the impurities. In addition to operational data and oil sample data, fuel sulfur content and an oil top-up date can be obtained as inputs. The fuel sulfur content is a measurement of how much sulfur is in the fuel supplied to the equipment 1604, which can vary widely across different geographical locations. The oil top-up date is the date of the last time that oil was added to the equipment 1604 or a time period since the last time that oil was added to the engine. Optionally, one or more equipment characteristics of the equipment 1604 may be considered, such as whether the engine is a two- or four-stroke engine. As another example, the type of fuel (e.g., gas versus diesel versus a fuel used in hybrid vehicles) can be received as inputs.

The controller 5702 can obtain information related to the equipment 1604 such as operational data, lubricant sample data, and/or lubricant change data. The operational data can include information indicative of usage of the equipment 1604, such as measurements of impurities in oil of the equipment 1604, date of or time since the last oil change, operational cycles of the equipment 1604, locations where the equipment 1604 operated, types of fuel used by the equipment 1604, duration of use of the equipment 1604, temperatures at which the equipment 1604 operated, ambient temperatures in which the equipment 1604 operated, geometrical details or measurements of the equipment 1604 and/or chamber in the equipment 1604 that holds the lubricant, power rating of the equipment 1604, lube system parameters of the equipment 1604 (e.g., lubricant flow rate, lubricant film temperature, combustion characteristics of the equipment 1604, etc.), and the like.

In one embodiment, the operational data obtained by the controller 5702 includes a lubricant top-off date and/or an impurity content of fuel used by the equipment 1604. The top-off date can be the date of or time since lubricant (e.g., oil) was last added to the equipment 1604. The impurity content of the fuel can be the amount of one or more impurities in the fuel consumed by the equipment 1604, such as the sulfur content of fuel supplied to the equipment 1604. Optionally, the operational data obtained by the controller 5702 includes a base oil composition, such as a grade of the lubricant.

The lubricant sample data includes measurements of the lubricant in the equipment 1604 obtained by the sensor probe assembly or assemblies 1608. These measurements can include identification of and/or concentrations of one or more impurities in the lubricant, such as water or non-hydrocarbon components. The lubricant change data can include information on when the lubricant was last changed or replaced, as opposed to when lubricant was last added to the equipment 1604.

Optionally, the measurement of the amount of impurities in the lubricant can include a measurement of one or more additives to the lubricant. For example, base additives can be added to oil to extend the life of the oil. The amount of one or more additives also can be measured and used to determine when a lubricant change is needed. For example, if an impurity measurement trends upward (e.g., soot) and/or an additive measurement trends downward (e.g., a base additive), then a lubricant change may be needed sooner than if the impurity measurement trends downward or remains the same and/or the additive measurement does not decrease.

The controller 5702 can perform an analysis of the obtained information to determine a remaining useful life (RUL) of the lubricant in the equipment 1604 based on the information. The controller 5702 can examine the operational data, lubricant sample data, and/or lubricant change data to determine how much longer the lubricant can be used without being changed or otherwise replaced at a time that is a designated period of time ahead of a scheduled maintenance of the equipment 1604. For example, the equipment 1604 and/or the rail vehicle 5704 can be scheduled for maintenance or an oil change every three months or three to five thousand miles. At a designated date (e.g., fourteen days ahead of the scheduled oil change or five hundred miles before the next oil change), the controller 5702 can automatically obtain the operational data, lubricant sample data, and/or lubricant change data from the memory device and determine the remaining useful life of the lubricant based on this information. Depending on how much longer the remaining useful life is, the controller 5702 may direct that the oil change not occur at the next scheduled maintenance, that the next scheduled maintenance be delayed, or that the next scheduled maintenance be performed sooner than the previously scheduled date. Optionally, the controller 5702 can perform the analysis of the operational data, lubricant sample data, and/or lubricant change data to create and/or update a model (e.g., a digital twin) of the equipment 1604, as described above.

Figure 17:
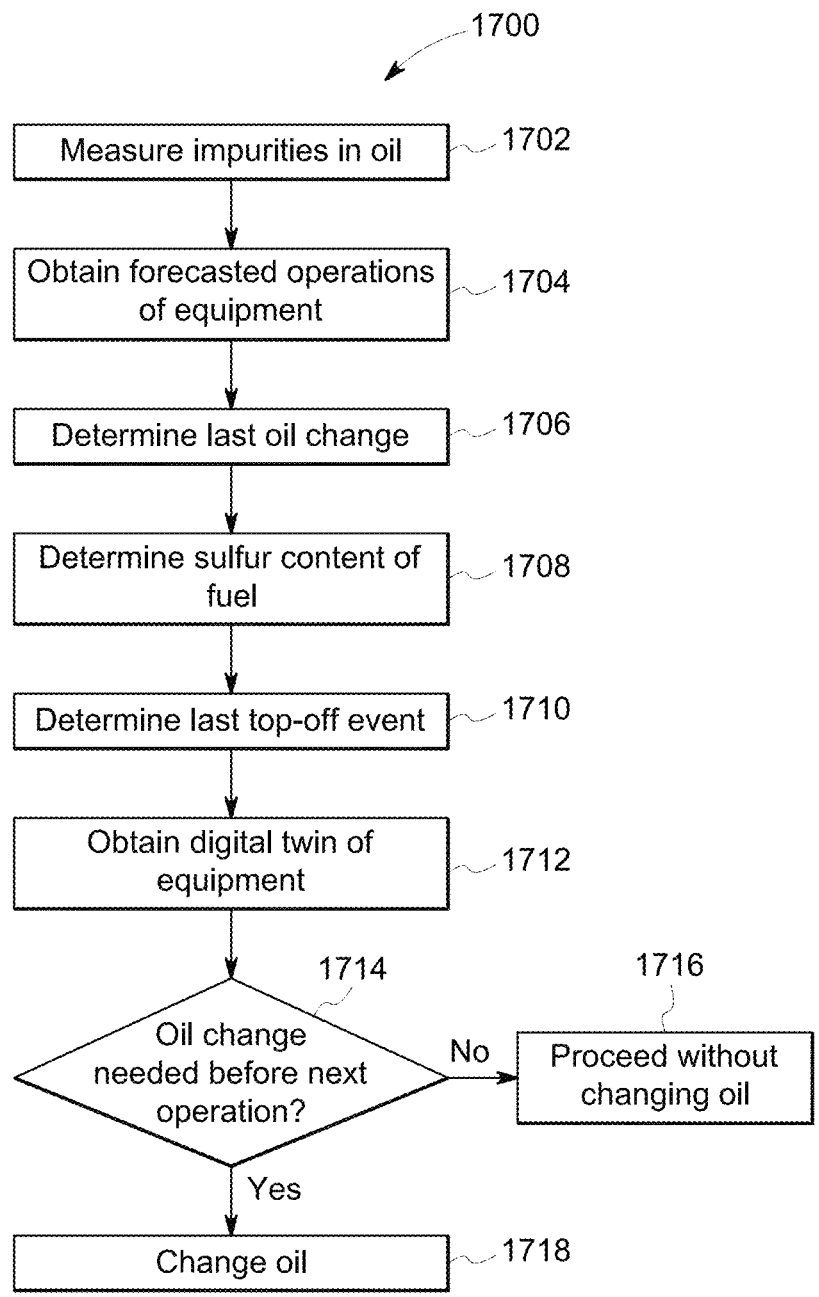
FIG. 17 illustrates a flowchart of one embodiment of a method for determining a maintenance event for equipment.

FIG. 17 illustrates a flowchart of one embodiment of a method 1700 for determining a maintenance event for equipment. The method 1700 can be used to determine when a lubricant change for the equipment 1604 is needed based on a variety of input data, which can include the sulfur content of fuel supplied to the equipment 1604 and/or the last time that lubricant was added to the equipment 1604. The flowchart of the method 1700 can represent operations performed by the controller 1602.

At 1702, the amount of one or more impurities in oil in an engine is determined. The impurity amount(s) can be measured by one or more of the sensor probe assemblies described herein. Alternatively, another type of sensor can be used. Optionally, the method 1700 does not include 1702. At 1704, forecasted operational conditions of the engine are obtained. For example, the ambient temperatures, engine speeds, engine temperatures, durations of operation, and the like, can be determined from operator inputs and/or from a scheduled or planned operation or mission of the engine. Optionally, the method 1700 does not include 1704. At 1706, the last time the oil of the engine was changed is determined. The date and/or time of this event can be stored in the memory device, and the time and/or number of duty cycles since the last time the oil was removed from the engine and then replenished is determined. Optionally, the method 1700 does not include 1706.

At 1708, the sulfur content of the fuel that is or will be supplied to the engine is determined. Different geographic areas may have different amounts of fuel impurities (e.g., sulfur) in the fuel that is available in those areas. Greater amounts of sulfur in fuel that is supplied to the equipment 1604 can result in the equipment 1604 operating at hotter temperatures, which can cause faster deterioration of the lubricant in the equipment 1604. One embodiment of the inventive subject matter described herein takes the amount of sulfur in fuel used to power the equipment 1604 into consideration when determining whether the existing lubricant in the equipment 1604 needs to be changed or whether the equipment 1604 can continue operating with the existing lubricant. The amount of sulfur in the fuel can be input by an operator of the system 1600, can be obtained from one or more remotely located memory devices (e.g., servers) via the network(s) 1610, or the like.

At 1710, a determination is made as to when lubricant was last added to the equipment 1604. At various times, one or more operators may add lubricant to the equipment 1604, such as when the operator(s) discover that the volume of lubricant in the equipment 1604 or a reservoir of the equipment 1604 is below a designated lower limit. Some volume of the lubricant can be added to the equipment 1604 and/or the reservoir of the equipment 1604 at a top-off event. The top-off event differs from the changing of the lubricant in that lubricant is added to, but not predominantly removed from, the equipment 1604 during a top-off event. Lubricant is predominantly removed (e.g., at least 90% by volume and/or weight) from the equipment 1604 and/or an associated reservoir, and then replaced during a changing of the lubricant. The time or date since the last top-off event can be input by an operator of the system 1600, can be obtained from one or more remotely located memory devices (e.g., servers) via the network(s) 1610, or the like.

At 1712, a digital twin of the equipment 1604 is obtained. The digital twin of the equipment 1604 can be created from the data and information obtained and/or determined at 1702, 1704, 1706, 1708, and/or 1710, and/or an existing digital twin of the equipment 1604 can be modified or updated based on some or all of this information. The digital twin can serve as an electronic representation of the equipment 1604, including some or all of the prior usage (duration of use, temperatures, sulfur contents of fuel, date/time of last top-off event, etc.).

At 1714, a decision is made by the controller 1602 as to whether a change of the lubricant is needed. This decision can be based on the controller 1602 examining the digital twin of the equipment 1604 (which electronically represents usage and/or wear and tear of the equipment 1604, deterioration or deteriorating conditions of the lubricant, etc.), determining forecasted operating conditions (e.g., planned, hypothetical, and/or predicted conditions in which the equipment 1604 will operate), the sulfur content of fuel previously supplied to the equipment 1604 and/or planned to be provided to the equipment 1604, and/or the time since the last top-off event. If the prior usage of the equipment 1604 and lubricant (as represented by the digital twin) indicates a longer time and/or more harsh operating conditions for the equipment 1604 (than a shorter operating time and/or less harsh operating conditions), then the controller 1602 may determine that an oil change is needed; if the previous sulfur content of the fuel used by the equipment 1604 is higher, then the controller 1602 may decide that an oil change is needed (when compared with lower sulfur contents); if it has been a longer period of time since the last top-off event, then the controller 1602 may determine that an oil change is needed (when compared with shorter periods of time since the last top-off event; and/or if the impurities measured in the oil by the sensor probe assemblies 1608 indicate greater amounts of impurities, then the controller 1602 may recommend changing the oil sooner (than if fewer amounts of impurities were measured). The controller 1602 can determine which combinations of these conditions indicate that an oil change is needed before operation of the equipment 1604 can continue, which combinations of conditions indicate that an oil change can be delayed, etc., based on empirically derived or determined combinations of conditions of other equipment 1604 and when oil changes for that other equipment 1604 occurred.

If the controller 1602 determines that a change in the lubricant is needed, then flow of the method 1700 can proceed toward 1718. At 1718, the lubricant of the equipment 1604 is changed. For example, the controller 1602 can prevent continued operation of the equipment 1604 by communicating one or more control signals to the equipment 1604 to shut down or prevent continued operation of the equipment 1604. As another example, the controller 1602 can send a warning signal to an operator that an oil change is needed. The controller 1602 can change or modify planned operational settings of the equipment 1604 to allow the equipment 1604 to continue operating without the oil change. For example, the equipment 1604 may be scheduled to propel a vehicle along a mountainous route in harsh conditions (e.g., elevated temperatures) carrying a heavy load before the next oil change. The controller 1602 can prevent this from occurring by either automatically directing the oil be changed or by changing the scheduled operational settings of the equipment 1604.

If the controller 1602 determines (at 1714) that a change in the lubricant is not needed, then flow of the method 1700 can proceed toward 1716. For example, the controller 1602 can determine that the equipment 1604 can continue operating (e.g., with the forecasted operating conditions) before an oil change is needed. As another example, the controller 1602 can determine that an oil change is needed, but that the previous and/or planned operating conditions of the equipment 1604 and/or lubricant allow for the equipment 1604 to continue operating longer without needed a change in lubricant. This can allow for maintenance of the equipment 1604 to be delayed without significant risk of damage to the equipment 1604.

Determining when or whether to change lubricant of the equipment 1604 as described herein provides for a condition-based performance of maintenance without significant changes in current operation of the equipment 1604. The useful life of lubricant can be extended beyond a designated oil-change schedule due to usage of the equipment 1604 in conditions that do not cause the lubricant to deteriorate as quickly, due to recent top-offs of the lubricant, due to low levels of impurities in the lubricant, etc. Additionally, the frequency at which the lubricant is sampled can be decreased in situations where usage of the equipment 1604 is in conditions that do not cause the lubricant to deteriorate as quickly, where the lubricant has been recently added, where there are low levels of impurities in the lubricant, etc. This can reduce the sampling cost involved in maintaining the equipment 1604. Additionally, the controller 1602 can determine when data outliers (e.g., measurements of abnormally elevated levels of impurities in oil) are false positive detections of impurities, versus when significant and real issues exist, due to examination of the digital twin and previous usage of the equipment 1604. For example, if the equipment 1604 has been used in less harsh conditions, lubricant has recently been added to the equipment 1604, other measurements of impurities were low or within acceptable limits, etc., then an abnormally high measurement of impurities in the lubricant can be identified by the controller 1602 as a data outlier, and not an actual problem with the lubricant.

In one embodiment, a method includes monitoring previous operational conditions of an engine that operates using fuel and a lubricant, identifying one or more of an impurity content of the fuel supplied to the engine or an elapsed time since a previous addition of additional lubricant to the lubricant in the engine, and determining whether a change of the lubricant is required prior to continued operation of the engine based on the previous operational conditions and the one or more of the impurity content of the fuel or the elapsed time since the previous addition of the additional lubricant to the lubricant in the engine.

Optionally, the method includes identifying the impurity content of the fuel and the impurity content is an amount of sulfur in the fuel.

Optionally, the method includes both identifying the impurity content of the fuel and the elapsed time since the previous addition of the additional lubricant. Determining whether the change of the lubricant is required can be based on the previous operational conditions, the impurity content of the fuel, and the elapsed time since the previous addition of the additional lubricant.

Optionally, the previous operational conditions include one or more of an elapsed operating time of the engine, an operating temperature of the engine, or an ambient temperature in which the engine operated.

Optionally, the method also can include creating or updating a digital twin of the engine based on the previous operational conditions of the engine, and forecasting upcoming operational conditions of the engine. Determining whether the change of the lubricant is required prior to the continued operation of the engine is based on the previous operational conditions, the one or more of the impurity content of the fuel or the elapsed time since the previous addition of the additional lubricant to the lubricant in the engine, the digital twin of the engine, and the upcoming operational conditions of the engine that are forecasted.

Optionally, the method also includes automatically changing the lubricant in the engine based on determining that the change in the lubricant is required. For example, one or more of the controllers described herein can generate and communicate control signals to a scheduling system that schedules the change or addition of lubricant to the engine.

Optionally, determining whether the change of the lubricant is required involves delaying the change of the lubricant beyond a previously scheduled maintenance of the engine that involves changing the lubricant.

Aging of chemical gas sensor systems such as the sensor probe assemblies described herein can pose a significant limitation in broad industrial application of the assemblies where long term stability of installed sensors is needed. To address this challenging problem, different approaches have been implemented. In particular, sensors are periodically recalibrated by removing the sensors from a measurement system, by bringing a carrier gas to the sensor without removing the sensors from the measurement system, and/or by simultaneously re-charging and calibrating the sensors on a regular basis (e.g., daily). Sensor aging is defined here as any detectable change in sensor sensitivity or sensor selectivity or sensor offset or sensor drift or sensor response time or sensor recovery time upon normal operation conditions of the sensor over time or upon exposure of the sensor to any undesired conditions. Nonlimiting examples of the undesired conditions may include poisoning, mechanical degradation, and any other undesired conditions.

These and other known calibration methods have significant limitations. For example, the methods can require calibrations with an analyte gas that occur more frequently than the maintenance cycle of the system itself (e.g., a transformer). As another example, the methods can require a calibration gas to be presented to the sensor.

One or more embodiments of the inventive subject matter described herein provide systems and methods that correct for the aging of one or more sensor probe assemblies without removal of the sensor probe assemblies from a measurement system and without the need for user interaction or recalibration with analyte. The systems and methods use the condition of the sensor probe assembly when the assembly is not responding to a gas or fluid of interest, but is quantitatively affected by aging of the sensor probe assembly. For example, when a sensor probe assembly is in the OFF state (i.e., not powered), this sensor condition or sensor state is quantitatively affected by the aging of the sensor probe assembly and can be detected by resistance and/or impedance spectroscopy readouts of the assembly at a specific range of frequencies. When the same sensor probe assembly is in the ON state (i.e., powered), the drift in the sensor response due to aging is correlated with the OFF state of the sensor probe assembly.

The response of the sensor probe assembly when in the OFF state (also referred to as the OFF sensor response) can be used to correct for drift in the response of the sensor probe assembly in the ON state (also referred to as the ON sensor response) due to aging. This technique of sensor correction is applied to one or more embodiments of the sensor probe assemblies having metal oxide semiconductor elements on the electrodes. The metal oxide semiconductor sensors can detect numerous gases by the selection of the base semiconductor material and the doping of the material. Impedance measurements of metal oxide semiconductor sensors are used to allow more selective sensor responses. When the sensor is in OFF state (not powered), the sensor output is measured and then utilized to correct for aging effects when the sensor is in the ON state.

This correction can reduce or eliminate the need for frequent sensor calibration using an analyte gas. Instead, when the sensor is aging, the aging condition of the sensor is quantified using the sensor response in the OFF state. The aging condition measured in the OFF state is then used to correct for effect of aging when the sensor is in the ON state and responding to the analyte gas, or gases of interest, and to known interferences. This aging condition of the sensor can be detected by resistance and/or impedance spectroscopy readouts at a specific range of frequencies.

Figure 18:
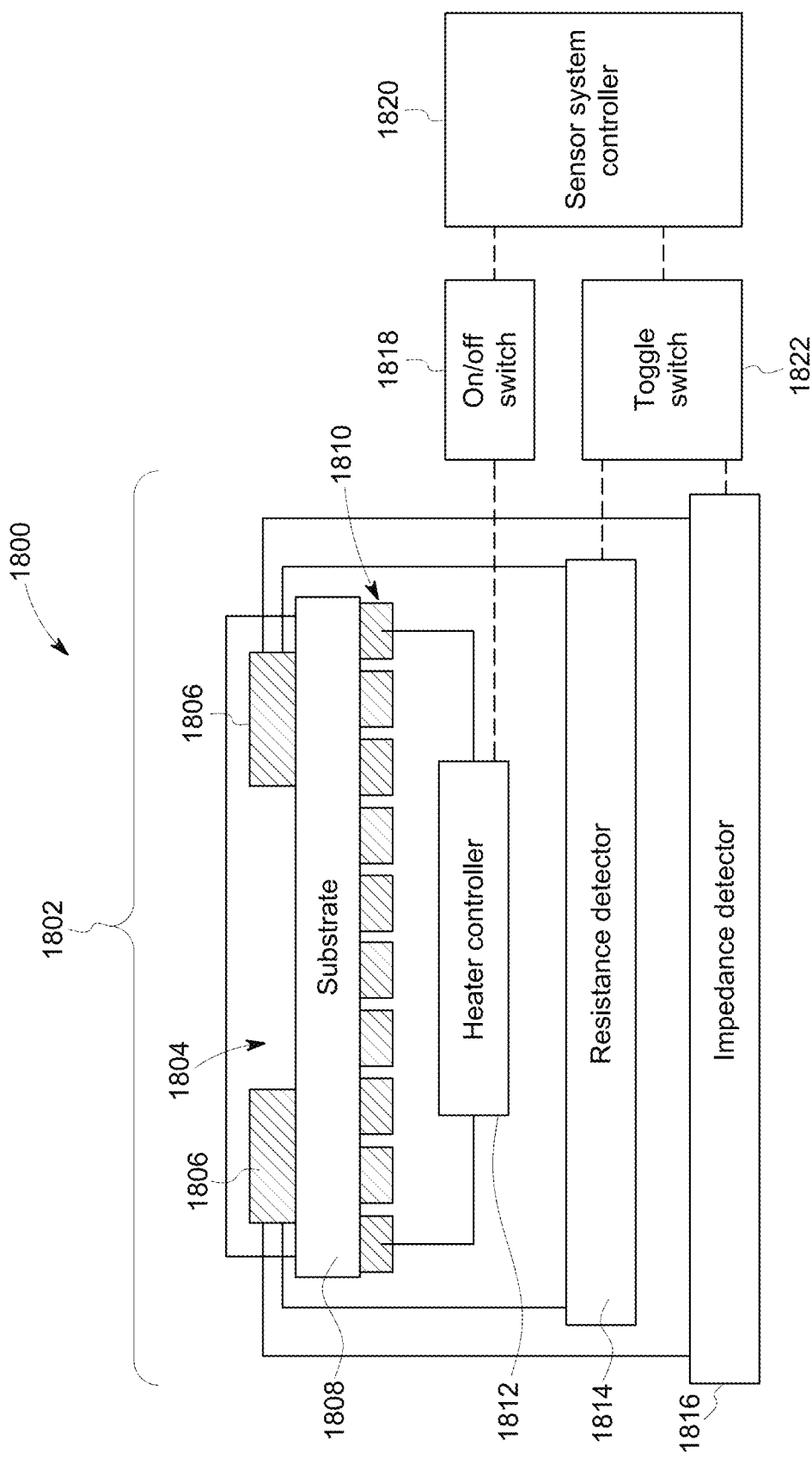
FIG. 18 illustrates one embodiment of a measurement system that corrects for aging in a sensor probe assembly.

FIG. 18 illustrates one embodiment of a measurement system 1800 that corrects for aging in a sensor probe assembly 1802. The sensor probe assembly 1802 can represent one or more of the sensor probe assemblies 100 described herein. Optionally, the sensor probe assembly 1802 can be another type of sensor probe assembly that measures concentrations of one or more analytes of interest in a fluid under examination using impedance spectral responses of a semiconductor material to the analytes and an electric field generated by electrodes. The fluid under examination can be gas.

The sensor probe assembly 1802 includes sensing material 1804 on and/or in contact with conductive electrodes 1806 that generate an electric field between the electrodes 1806. The sensing material 1804 can be a metal oxide semiconductor material, such as SnO2. The electrodes 1806 are shown as being deposited on a dielectric substrate 1808 (e.g., the substrate 102, 906), but alternatively may be the free-standing electrodes with the sensing material 1804 deposed thereon, as described above. One or more heating elements 1810 are formed from conductive bars, plates, or other resistive bodies that receive electric current to heat the substrate 1808, the sensing material 1804, and/or the electrodes 1806.

A heater controller 1812 represents hardware circuitry that is conductively coupled with and conducts electric current to or through the heating elements 1810 to generate heat. A resistance detector 1814 represents hardware circuitry that is conductively coupled with the electrodes 1806 to measure electric resistance between the electrodes 1806 (e.g., through the sensing material 1804, which can have a resistance and/or impedance that varies based on the presence and/or amount of impurities or analytes of interest in the fluid under examination). The resistance detector 1814 performs measurements of resistance of the sensing material 1804 while the sensor probe assembly 1802 is in the ON state (e.g., power is being supplied to the heating elements 1810 from the heater controller 1812).

The system 1800 also includes additional sensor components such as an impedance detector 1816, which represents hardware circuitry that is conductively coupled with the electrodes 1806 and that measures the impedance of the sensing material 1804 between the electrodes 1806 while the sensor probe assembly 1802 is in the ON state and/or the OFF state. The ON state of the sensor is when a nominal required power is supplied to the heating elements 1810 from the heater controller 1812 to achieve a desired response of the sensor to the analyte of interest. Such desired sensor response is achieved when the sensing material 1804 operates at needed temperature in the range from about 100 degrees Celsius to about 800 degrees Celsius and more particularly in the range from about 200 degrees Celsius to about 500 degrees Celsius. The OFF state of the sensor is when a nominal required power is not supplied to the heating elements 1810 from the heater controller 1812 so the sensor does not have a detectable response to the analyte of interest. Two examples of "no nominal required power" include (1) zero applied power when the heating elements 1810 have zero power from the heater controller 1812 and allows the sensing material 1804 to be at ambient temperature or (2) minimal applied power when the heating elements 1810 have minimal power from the heater controller 1812 that does not produce a desired response of the sensor to the analyte of interest but allows the sensing material 1804 to be slightly above ambient temperature. For example, if ambient temperature is below zero degrees Celsius, the sensing material 1804 can be slightly above zero degrees Celsius (for example at 5-20 degrees Celsius) to avoid freezing of condensed water from ambient air onto the sensing material 1804. A first switch 1818 ("ON/OFF switch" in FIG. 18) operates under the control of a sensor system controller 1820 to switch between activating the heater controller 1812 (to supply current to the heating elements 1810) and deactivating the heater controller 1812 (to stop supplying current to the heating elements 1810). A second switch 1822 ("Toggle switch" in FIG. 18) is controlled by the controller 1820 to alternate between activating the resistance detector or sensor 1814 (to measure the resistance in the sensing material 1804) or activating the impedance detector or sensor 1816 (to measure the impedance in the sensing material 1804). The controller 1820 represents hardware circuitry that includes and/or is connected with one or more processors to control whether the resistance detector 1814 or impedance detector 1816 is activated, and whether the heater controller 1812 is activated using the switches 1818, 1822. The controller 1820 can operate based off on input received from an operator and/or may automatically control the switches 1818, 1822 (e.g., based on a clock and/or schedule).

One example of a transfer function for predicting a gas concentration from a response of the sensing material 1804 of the sensor probe assembly described herein is:

$$[\text{gas}] = A^*[\text{sensor response}]^B$$

where [gas] is the predicted gas concentration (or concentration of an analyte of interest in a fluid such as a gas, [sensor response] is the measured response of the sensor probe assembly, and A and B are coefficients of the transfer function. These coefficients of the transfer function may be used for temperature correction and other factors, such as correction for humidity and other gases. The values of the coefficients can be set based on known concentrations of the analyte of interest in a gas sample during calibration of the sensor probe assembly.

Inventors of the inventive subject matter described herein have discovered that the values of the coefficients A and B of this transfer function are dependent on the aging status of the sensor probe assembly. To get the dependence of these coefficients on sensor aging, but not on the possible analyte gas concentration, the response of the sensor probe assembly can be measured when the sensor probe assembly is unpowered. Stated differently, when the sensor probe assembly is OFF, the sensor probe assembly does not respond to the gas of interest, and measurements of the response of the assembly may be indicative of or represent changes to the values of A and/or B due to aging.

The controller 1820 can direct the sensor probe assembly 1802 to operate in an impedance mode where the impedance of the sensing material 1804 is measured. The switch 1822 is actuated to activate the impedance detector 1816 and to measure the [sensor response] as Zorn (which is impedance of the sensor probe assembly 1802 at a designated frequency) while the sensor probe assembly 1802 is ON. The coefficients A and B can be related to the sensor probe assembly in the ON state and OFF state as follows:

$$[\text{gas}] = A_{ON,OFF} {}^* Z_{ON}^{B_{ON,OFF}}$$

where the changes in coefficients $A_{ON, OFF}$ and $B_{ON, OFF}$ are due to the response of the sensor probe assembly 1802 to an analyte of interest (e.g., H2) while the sensor probe assembly 1802 is in the ON state as correlated to sensor aging (as determined from measurements obtained while the sensor probe assembly 1802 is in the OFF state).

Figure 19:
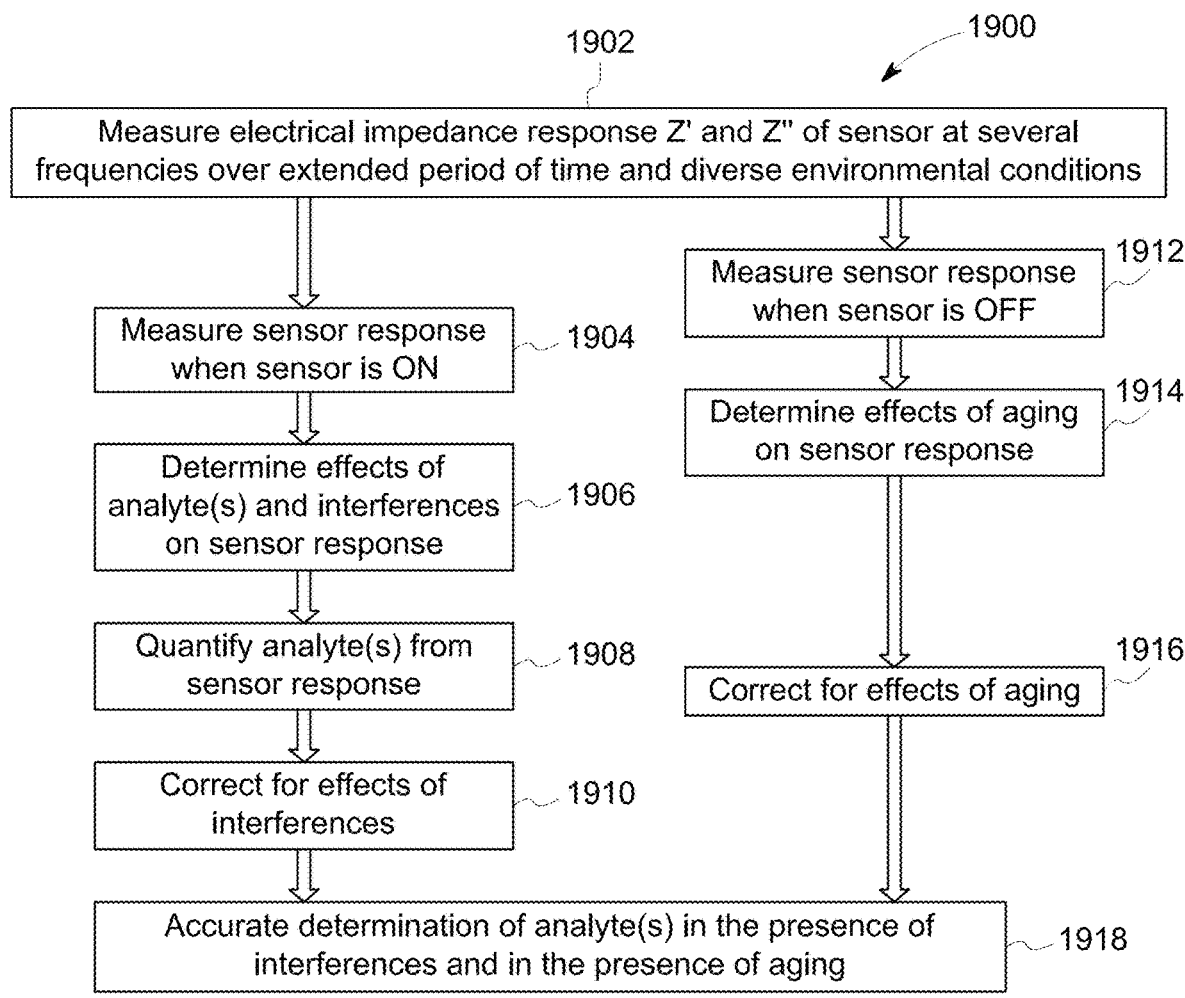
FIG. 19 illustrates a flowchart of one embodiment of a method for correcting measurements of a sensor probe assembly for aging.

FIG. 19 illustrates a flowchart of one embodiment of a method 1900 for correcting measurements of a sensor probe assembly for aging. The method 1900 can be performed by the system 1800 and/or the controller 1820 of the system 1800 to correct measurements obtained by one or more of the sensor probe assemblies described herein.

At 1902 and 1904, real (Z') and imaginary (Z") parts of the electrical impedance response of the sensing material of the sensor probe assembly are measured at several different frequencies while the sensor is in the ON state over an extended period of time and/or under diverse environmental conditions (e.g., exposure to different fluids of interest, different ambient temperatures, etc.). These responses of the sensor probe assembly can be measured by the controller 1802 based on output from the impedance detector 1816. At 1906, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 1908, the analyte(s) in the fluid under examination can be identified based on the sensor response, such as by identifying peaks in one or more impedance spectra of the sensor probe assembly that are associated with the analyte(s) of interest. At 1910, the effects of interferences can be corrected for, such as the impact of aging on the sensor probe assembly, as described in connection with 1912, 1914, 1916. At 1918, the accuracy of quantitation of analytes is achieved from the correction of sensor response based on the effects of the interferences (e.g., aging of the sensor probe assembly).

The method 1900 also includes, at 1902 and 1912, measuring the intrinsic impedance of the sensor probe assembly while the sensor probe assembly is OFF (not powered). These measurements can be performed at designated frequencies that allow the use of conventional measurement systems with detection of 1 GOhm, 100 MOhm, 10 MOhm, or 1 MOhm. At 1914, the values of the sensor impedance at one or more designated frequencies while the sensor probe assembly is in the OFF state are determined. These frequencies can be empirically determined from the same or other similar sensor probe assemblies. These values indicate the effects of aging on the sensor probe assembly.

At 1916, the values determined at 1914 are used for correction of the instabilities of the sensor response due to sensor aging. Also, the values of the sensor impedance at certain frequencies are used for correction of the instabilities of the sensor response to an analyte gas of interest when the sensor is powered. For example, these values may be subtracted or otherwise removed from the values determined at 1904 and/or 1908.

Figure 20:
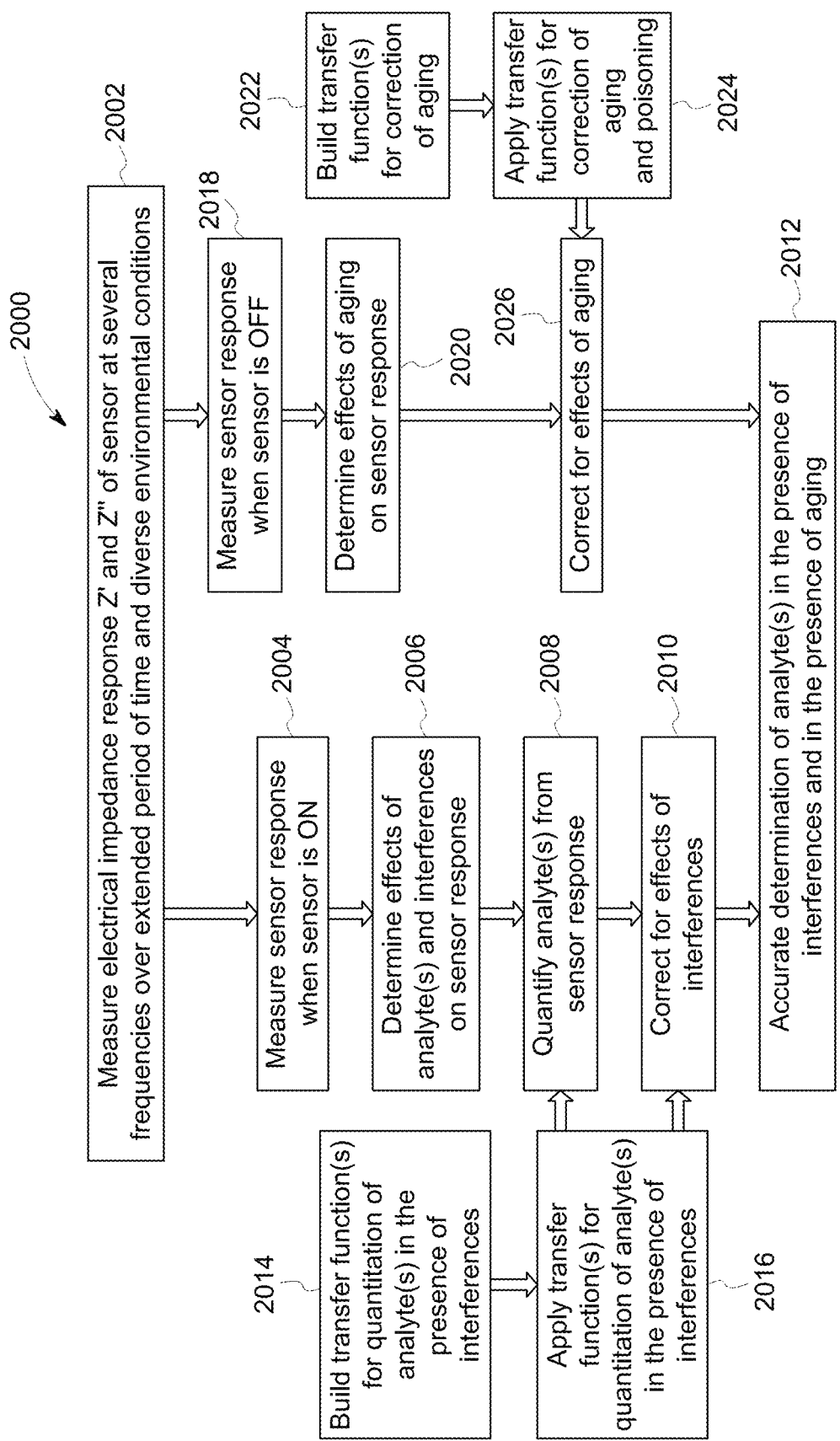
FIG. 20 illustrates another flowchart of one embodiment of a method for correcting measurements of a sensor probe assembly for aging.

FIG. 20 illustrates another flowchart of one embodiment of a method 2000 for correcting measurements of a sensor probe assembly for aging. The method 2000 can be performed by the system 1800 and/or the controller 1820 of the system 1800 to correct measurements obtained by one or more of the sensor probe assemblies described herein. At 2002 and 2004, the real part (Z') and imaginary part (Z") of the electrical impedance response of the sensor probe assembly are measured at several designated frequencies while the sensor probe assembly is in the ON state over extended period of time and while exposed to diverse environmental conditions.

At 2006, the values of the sensor impedance at designated frequencies are used to determine the effects of interferences and analytes on the sensor probe assembly. For example, the presence of some impurities in a fluid under examination can impact the real part (Z') and/or the imaginary part (Z") of the electrical impedance response of the sensor probe assembly, which also can be impacted by one or more analytes of interest in the fluid. At 2008, the analyte(s) in the fluid under examination can be identified based on the sensor response, such as by identifying peaks in one or more impedance spectra of the sensor probe assembly that are associated with the analyte(s) of interest.

At 2010, the accuracy of quantitation of analytes is achieved from the correction of sensor response based on the effects of the interferences. For example, the impact of sensor aging on the sensor response measured at 2004 can be removed from the measured sensor response. The analytes of interest in the fluid under examination can then be identified at 2012.

In one embodiment, one or more transfer functions are built or otherwise created for quantitation of one or more analytes of interest in the presence of interferences, such as impurities or manufacturing errors, at 2014. These transfer functions can be built during sensor fabrication and calibration. These transfer functions are applied to quantify one or more analytes in the presence of interferences. For example, at 2008 and/or 2010, one or more of the transfer functions (determined at 2014) can be applied to the sensor response to eliminate or reduce the impact of the sensor response on the interferences.

The method 2000 also includes, at 2002 and 2018, measuring the intrinsic impedance of the sensor probe assembly while the sensor probe assembly is OFF (not powered). These measurements can be performed at designated frequencies that allow the use of conventional measurement systems with detection of 1 GOhm, 100 MOhm, 10 MOhm, or 1 MOhm. At 2020, the values of the sensor impedance at one or more designated frequencies while the sensor probe assembly is in the OFF state are determined. These frequencies can be empirically determined from the same or other similar sensor probe assemblies. These values indicate the effects of aging on the sensor probe assembly.

One or more transfer functions are built or otherwise created for quantitation of the impact of sensor aging at 2022. These transfer functions can be created based on the sensor responses measured when the sensor probe assembly is OFF, as described above. These transfer functions are applied to quantify one or more analytes in the presence of interferences. For example, at 2024, one or more of the transfer functions (determined at 2022) can be applied to the sensor response to eliminate or reduce the impact of the sensor response due to aging (at 2026).

Figure 21:
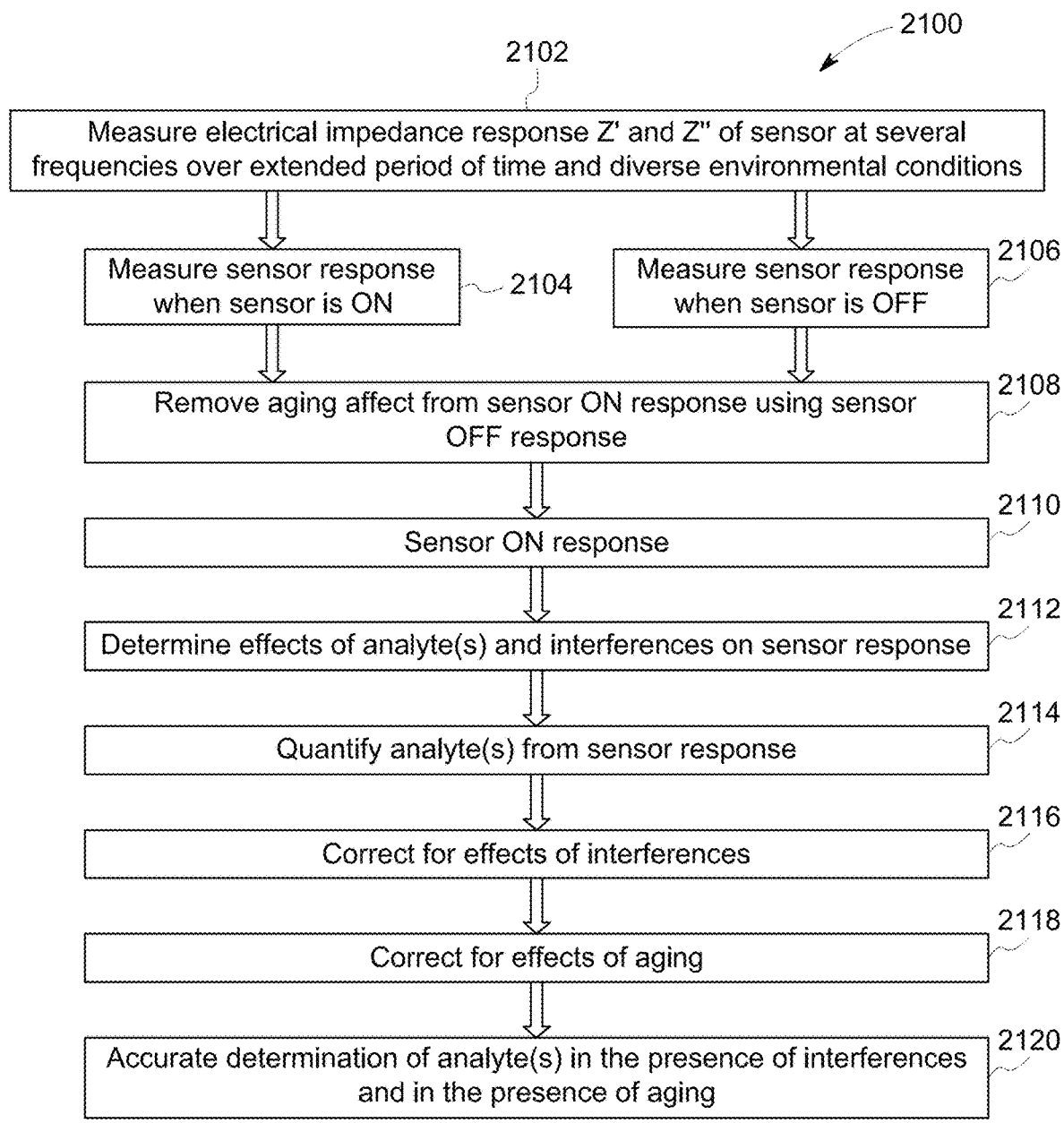
FIG. 21 illustrates a flowchart of one embodiment of a method for correcting measurements of a sensor probe assembly for aging.

FIG. 21 illustrates a flowchart of one embodiment of a method 2100 for correcting measurements of a sensor probe assembly for aging. The method 2100 can be performed by the system 1800 and/or the controller 1820 of the system 1800 to correct measurements obtained by one or more of the sensor probe assemblies described herein.

At 2102, real (Z') and imaginary (Z") parts of the electrical impedance response of the sensing material of the sensor probe assembly are measured at several different frequencies over an extended period of time and/or under diverse environmental conditions (e.g., exposure to different fluids of interest, different ambient temperatures, etc.). These responses can be measured while the sensor probe assembly is ON (at 2104) and while the sensor probe assembly is OFF (at 2106).

The effects of the sensor responses due to aging of the sensor probe assembly are removed from the sensor responses measured while the sensor probe assembly is ON at 2108. For example, the real (Z') and imaginary (Z") parts of the electrical impedance response of the sensing material of the sensor probe assembly may be measured while the sensor probe assembly is OFF (at 2106). The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

After removing the effects of sensor aging (or at least determining the impact of aging so that the impact can later be removed), the real (Z') and imaginary (Z") parts of the electrical impedance response of the sensing material of the sensor probe assembly can be measured for a fluid under examination at 2110. At 2112, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 2114, one or more analytes of interest in the fluid under examination are quantified or identified using the sensor response measured at 2110. At 2116, the effect of these interferences can be corrected for, such as by removing the effect of the interferences from the sensor response determined at 2112.

At 2118, the effects of the sensor responses due to aging of the sensor probe assembly optionally are removed from the sensor responses measured while the sensor probe assembly is ON (at 2110). For example, the real (Z') and imaginary (Z") parts of the electrical impedance response of the sensing material of the sensor probe assembly may be measured while the sensor probe assembly is OFF. The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

At 2120, one or more analytes of interest are identified in the fluid under examination with the effects of interferences and the effects of sensor aging removed or reduced from the sensor response. As described herein, different analytes of interest can be associated with different peaks in the real (Z') and/or imaginary (Z") parts of the impedance responses of the sensor probe assembly. After removing the effects of interferences and sensor aging from the sensor response to the fluid under examination, the sensor response may more accurately reflect the presence and/or amount of the analyte(s) of interest in the fluid under examination.

Figure 22:
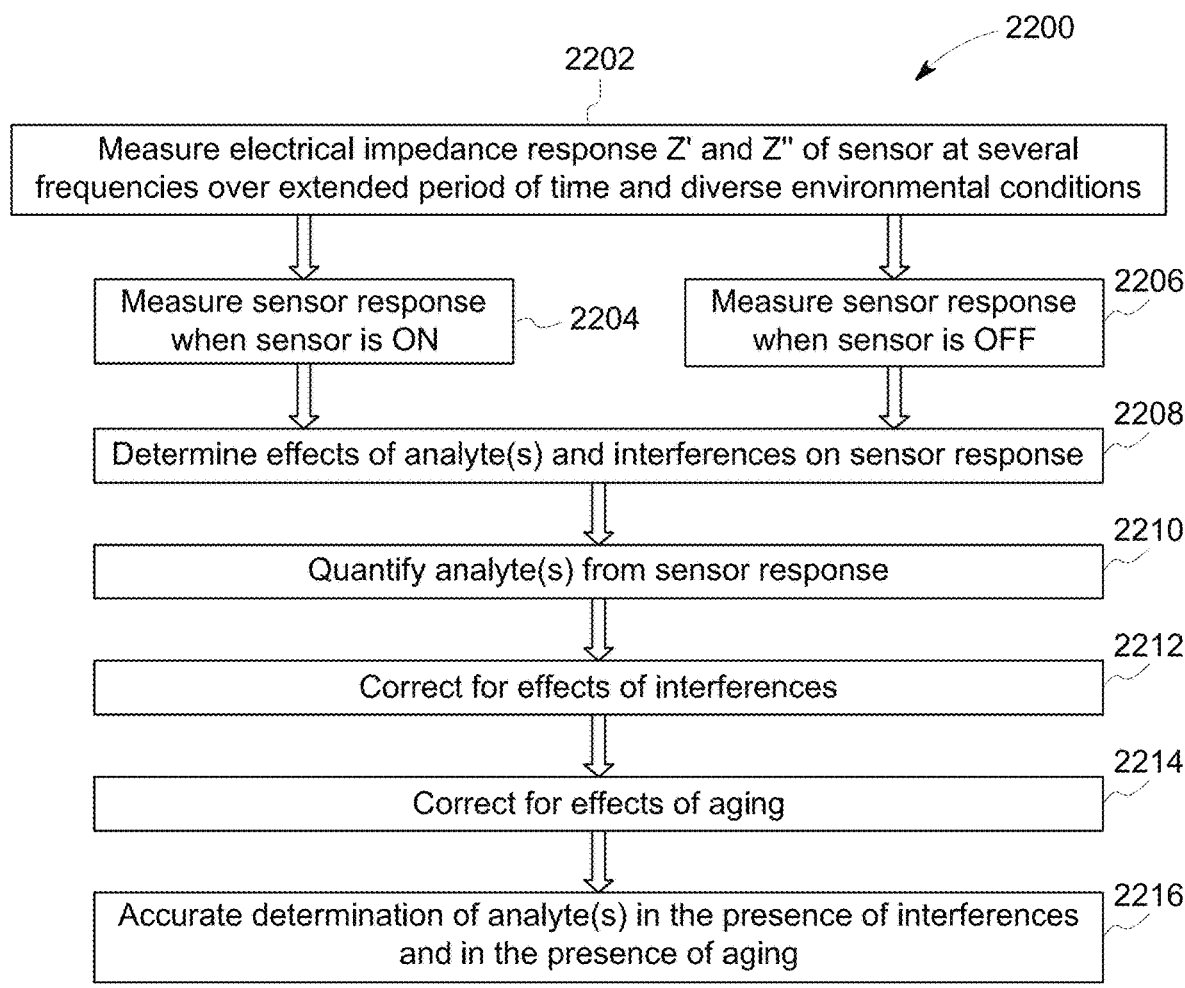
FIG. 22 illustrates a flowchart of one embodiment of a method for correcting measurements of a sensor probe assembly for aging.

FIG. 22 illustrates a flowchart of one embodiment of a method 2200 for correcting measurements of a sensor probe assembly for aging. The method 2200 can be performed by the system 1800 and/or the controller 1820 of the system 1800 to correct measurements obtained by one or more of the sensor probe assemblies described herein.

At 2202, real (Z') and imaginary (Z") parts of the electrical impedance response of the sensing material of the sensor probe assembly are measured at several different frequencies over an extended period of time and/or under diverse environmental conditions (e.g., exposure to different fluids of interest, different ambient temperatures, etc.). These responses can be measured while the sensor probe assembly is ON (at 2204) and while the sensor probe assembly is OFF (at 2206).

At 2208, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 2210, one or more analytes of interest in the fluid under examination are quantified or identified using the measured sensor responses.

At 2212, the effect of these interferences can be corrected for, such as by removing the effect of the interferences from the sensor response that was determined. At 2214, the effects of the sensor responses due to aging of the sensor probe assembly optionally are removed from the sensor responses measured while the sensor probe assembly is ON. For example, the real (Z') and imaginary (Z") parts of the electrical impedance response of the sensing material of the sensor probe assembly may be measured while the sensor probe assembly is OFF. The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

At 2216, one or more analytes of interest are identified in the fluid under examination with the effects of interferences and the effects of sensor aging removed or reduced from the sensor response. As described herein, different analytes of interest can be associated with different peaks in the real (Z') and/or imaginary (Z") parts of the impedance responses of the sensor probe assembly. After removing the effects of interferences and sensor aging from the sensor response to the fluid under examination, the sensor response may more accurately reflect the presence and/or amount of the analyte(s) of interest in the fluid under examination.

The sensor probe assemblies described herein can be used to quantify at least one analyte gas that is dissolved in insulating oil of an electrical transformer. The sensor probe assemblies can be used to quantify at least one analyte gas dissolved in insulating oil of an electrical transformer when the sensor probe assemblies are turned off for extended periods of time (e.g., time periods that are at least 10 times longer that the measurement time of the analyte gas dissolved in insulating oil of an electrical transformer). The sensor probe assembly can be used to quantify analytes of interest such as hydrogen, CO, or a hydrocarbon gas.

The measurement systems described herein can be used to measure a gas extracted from oil (e.g., transformer dissolved gas analysis). The measurement system can include a sensing element or material connected to an impedance detector or analyzer circuit, where the impedance detector or analyzer circuit measures the response of the sensing element when exposed to a gas that has been extracted from oil and corrects for sensor aging. The sensing element can be connected to a resistance detector or measurement circuit (or equivalent), where the resistance circuit measures the response of the sensing element when exposed to a gas that has been extracted from oil and corrects for sensor aging.

In one embodiment, the measurement system operates with a sensing element (e.g., the sensing material) in a gas sample which has been extracted from transformer oil. The sensing element is connected to an impedance analyzer and scanned as a function of frequency, where the impedance analyzer circuit provides data output enabling improved sensor selectivity across multiple gases and improved sensor stability based on the correction of the sensor response performed when the sensor is in the OFF state. Aging of the sensor probe assembly can induce significant error in predicted gas concentrations and when the use of sensor readings in a "sensor OFF" state corrects for sensor aging and when incorporation of the "sensor OFF" response into a transfer function reduces prediction error of gas concentrations.

A method also is provided herein where sensor aging induces significant error in predicted gas concentrations. The use of sensor readings in a "sensor OFF" state corrects for sensor aging and incorporation of the "sensor OFF" response into a transfer function reduces prediction error of gas concentrations. The sensor response in the OFF state can be quantified using a resistance measurement of the sensing material (i.e., instead of the impedance response), and the sensor response in the ON state can be quantified using the impedance response. Optionally, the sensor response in the OFF state can be quantified using a resistance measurement of the sensing material (i.e. instead of the impedance response), and the sensor response in the ON state is also quantified using the resistance response.

In one embodiment, the sensor response in the OFF state is quantified using the resistance measurement (i.e. instead of the impedance response), and the sensor response in the ON state is also quantified using the resistance response. Optionally, the sensor response in the OFF state is quantified using the resistance measurement (i.e. instead of the impedance response), and the sensor response in the ON state is also quantified using the resistance response.

The frequencies, or frequency ranges, used to measure the impedance response of the sensor probe assembly to quantify the sensor OFF and ON states are different. The sensor response in the OFF state can be used to correct the sensor response in the ON state prior to applying transfer functions that quantify the analyte gas, or gases of interest. The sensor response in the OFF state can be used simultaneously with the sensor response in the ON state to quantify the analyte gas, or gases of interest. The sensitivity of the transfer functions to the sensor OFF or ON responses can be increased by preprocessing the sensor OFF or ON responses.

In one embodiment, recalibration, realignment or correction for sensor aging using sensor response in the resistance or impedance domain is performed on a periodic basis, as opposed to being part of a standard measurement cycle. Sensor analysis can be performed on a cyclical basis (such as every 24 hours, weekly, monthly, etc.) and changes in measurement performance (drift, aging etc.) can be corrected based on a cyclic correction. The sensor resistance response in the sensor OFF state can be used as a diagnostic indicator for sensor performance. The information extracted from the resistive method will indicate whether the sensor performance is within an acceptable range or whether the sensor performance has drifted outside the acceptable range.

Several measurements were performed using a sensor probe assembly described herein with a SnO2 metal oxide semiconducting sensing material. The readout was performed using an impedance measurement over the relaxation region of the sensing material or classic resistance measurement. A SnO2 sensor probe assembly was aged by exposing the sensor probe assembly to D3 silicone vapor. Such aging reduces the magnitude of the response of the sensor probe assembly to analytes of interest. The sensor probe assembly was exposed to several concentrations of hydrogen gas before and after aging. Concentrations of H2 were 50, 100, 150, and 200 ppm. Exposure to silicone vapor was performed when the sensor probe assembly was in the OFF state to mimic the realistic conditions of the operation of the sensor. Exposures were performed for different durations of 15, 60, and 90 min by keeping the sensor probe assembly in the headspace above the silicone material.

Figure 23:
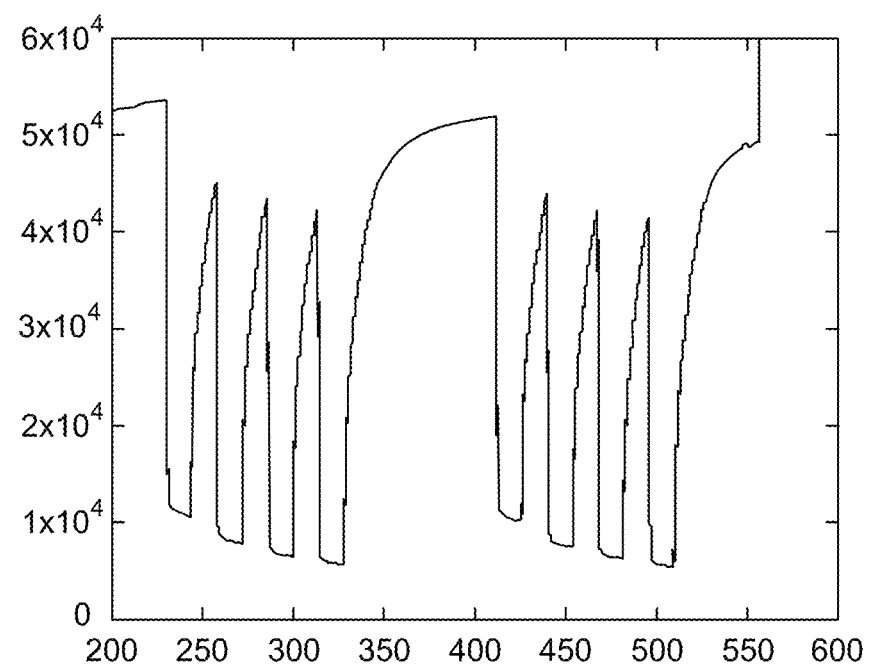
FIG. 23 illustrates response of a sensor probe assembly when the sensor probe assembly was tested during exposure to H2 before and after accelerated aging steps.
Figure 24:
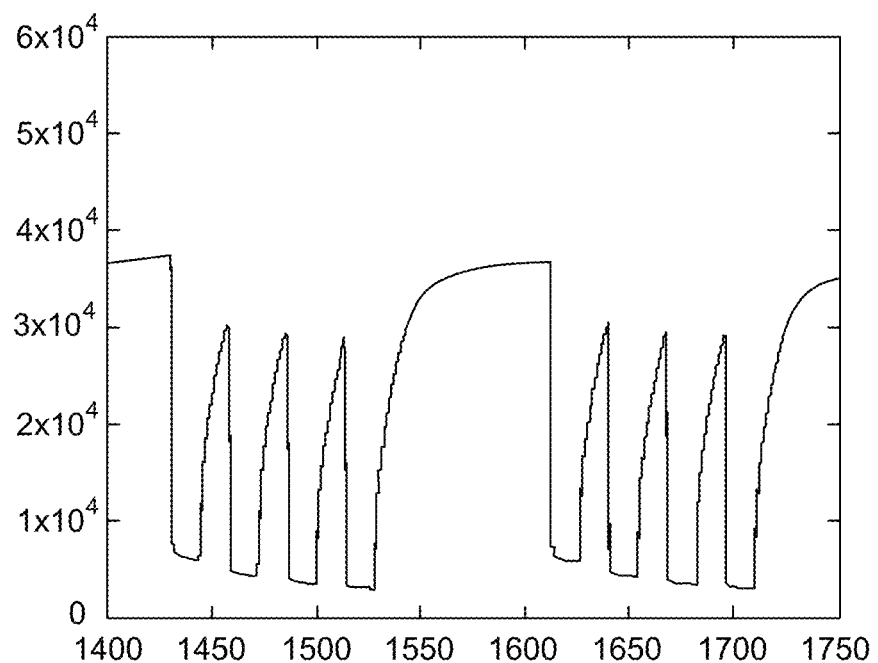
FIG. 24 illustrates additional response of a sensor probe assembly when the sensor probe assembly was tested during exposure to H2 before and after accelerated aging steps.
Figure 25:
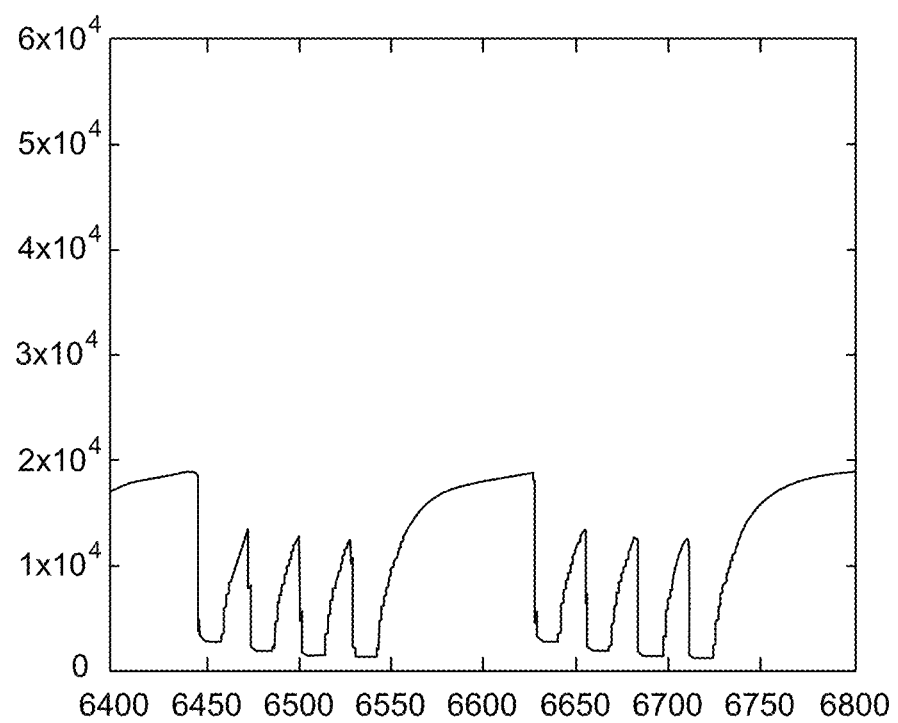
FIG. 25 illustrates additional response of a sensor probe assembly when the sensor probe assembly was tested during exposure to H2 before and after accelerated aging steps.
Figure 26:
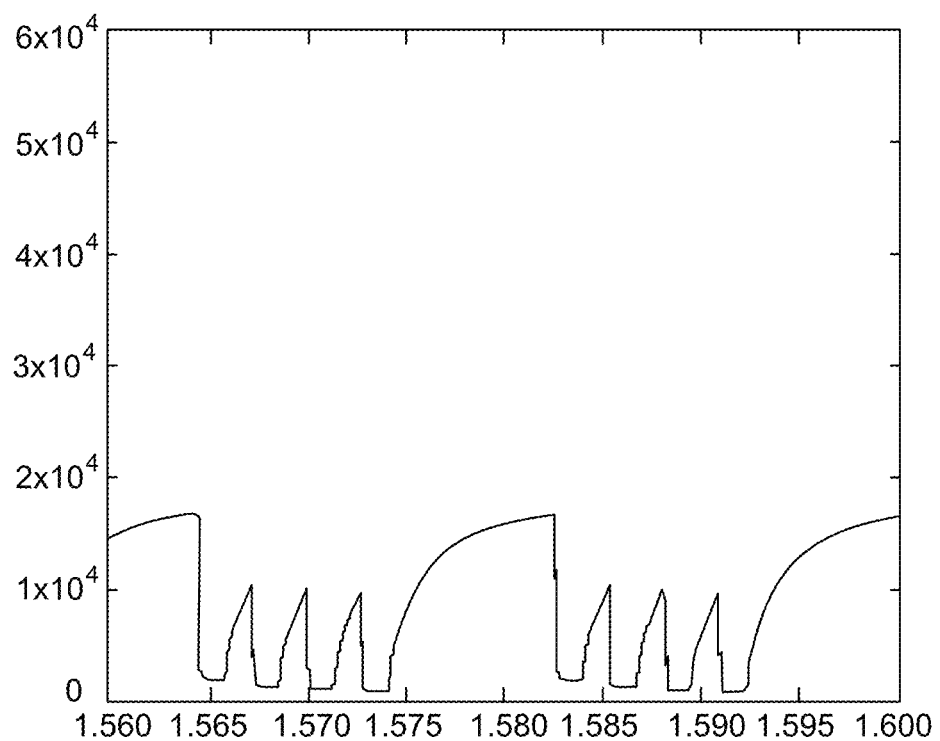
FIG. 26 illustrates additional response of a sensor probe assembly when the sensor probe assembly was tested during exposure to H2 before and after accelerated aging steps.

FIGS. 23 through 26 illustrate responses of the sensor probe assembly when the sensor probe assembly was tested during exposure to H2 before and after the accelerated aging steps described above. Before aging, the sensor probe assembly had a response to 0-200 ppm of H2 that was significantly decreased after aging. FIG. 23 illustrates the sensor response with no aging of the sensor probe assembly, FIG. 24 illustrates the sensor response with aging of the sensor probe assembly for fifteen minutes in silicone vapor, FIG. 25 illustrates the sensor response with aging of the sensor probe assembly for sixty minutes in silicone vapor, and FIG. 26 illustrates the sensor response with aging of the sensor probe assembly for ninety minutes in silicone vapor. The concentrations of H2 were 50, 100, 150, and 200 ppm. The sensor response was collected by using an impedance analyzer at 1.5 kHz.

Figure 27:
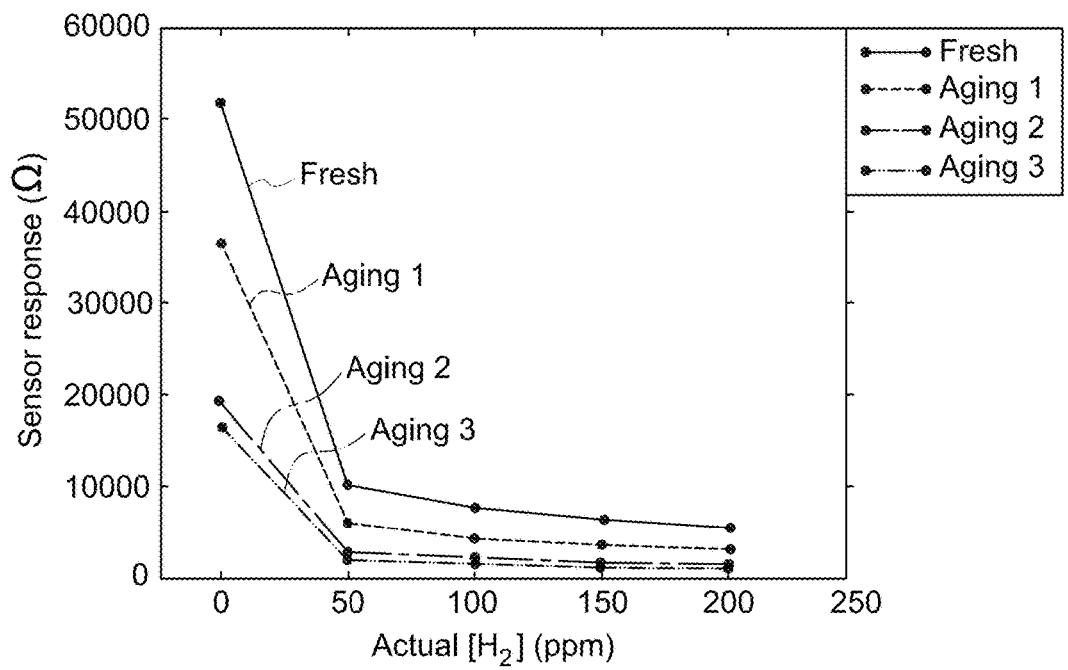
FIG. 27 depicts calibration curves of the response of the sensor probe assembly when the sensor probe assembly was tested H2 before and after the accelerated aging steps.

FIG. 27 depicts calibration curves of the response of the sensor probe assembly when the sensor probe assembly was tested H2 before and after the accelerated aging steps. The calibration curves were significantly affected by the aging of the sensor probe assembly, as shown by the decreasing magnitudes of the sensor response with increased aging. The different calibration curves are associated with aging of the sensor probe assembly by zero minutes (or no aging, referred to as "fresh" in FIG. 27), fifteen minutes ("aging 1" in FIG. 27), sixty minutes ("aging 2" in FIG. 27), or ninety minutes ("aging 3" in FIG. 27).

Figure 28:
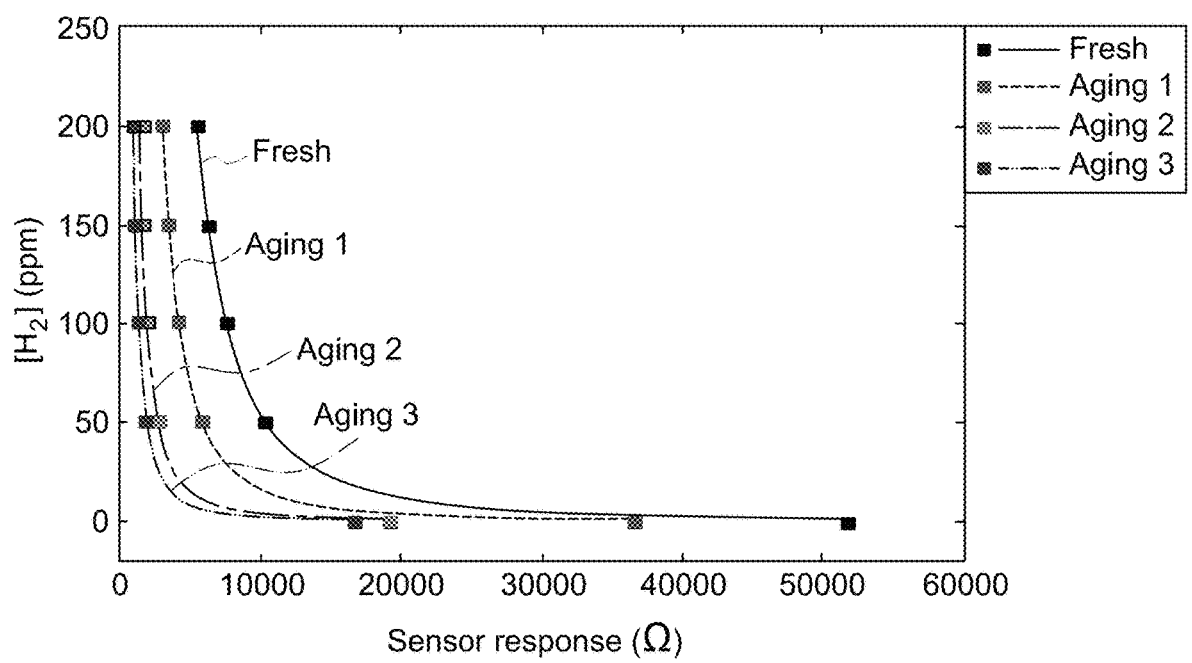
FIG. 28 illustrates responses of the sensor probe assembly to H2 at 1.5 kHz at various H2 concentrations.

FIG. 28 illustrates responses of the sensor probe assembly to H2 at 1.5 kHz at various H2 concentrations. The data shown in FIG. 28 has been fit with power law fits as:

$$[H2, ppm] = A * Z_{ON}^{B}$$

The coefficients A and B of the fits are presented in Table 1 below. These coefficients are related to the changes of the sensor response upon sensor aging.

TABLE 1

| Sensor condition | Coefficient A | Coefficient B |
|---|---|---|
| fresh | 3.46e+10 | −2.20e+00 |
| After aging 1 | 6.22e+09 | −2.14e+00 |
| After aging 2 | 4.12e+08 | −2.00e+00 |
| After aging 3 | 1.53e+08 | −1.96e+00 |

Figure 29:
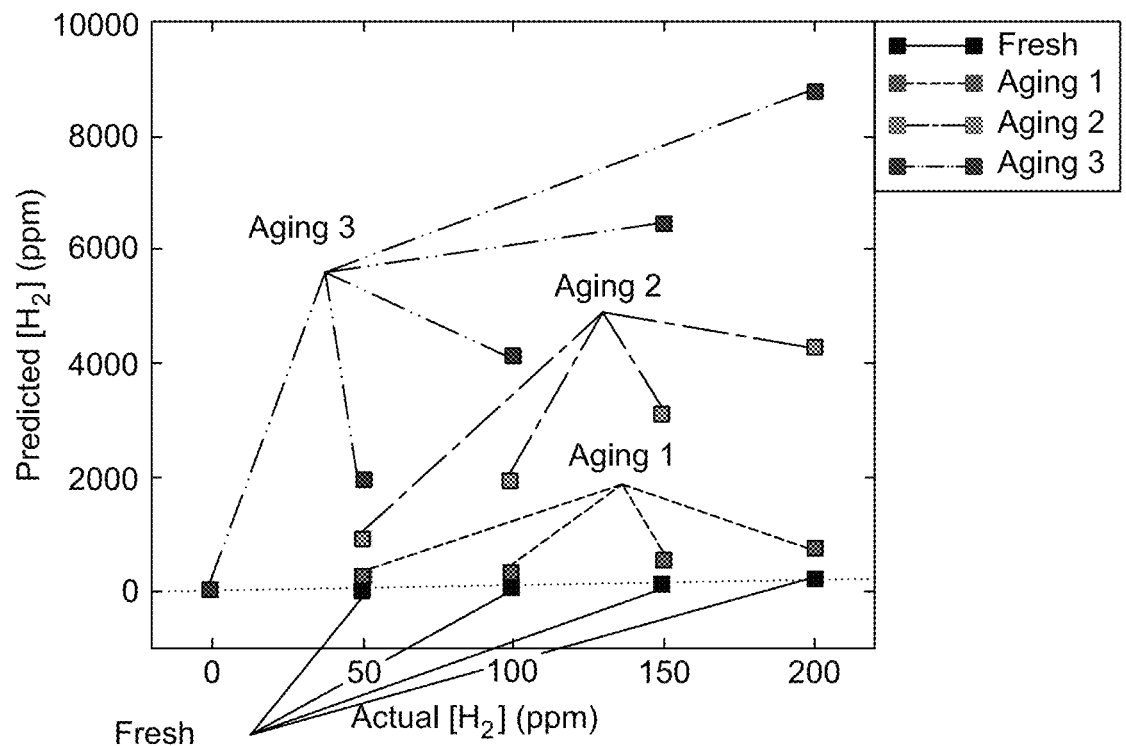
FIG. 29 depicts use of a transfer function developed for a fresh sensor probe assembly (with no aging)
Figure 30:
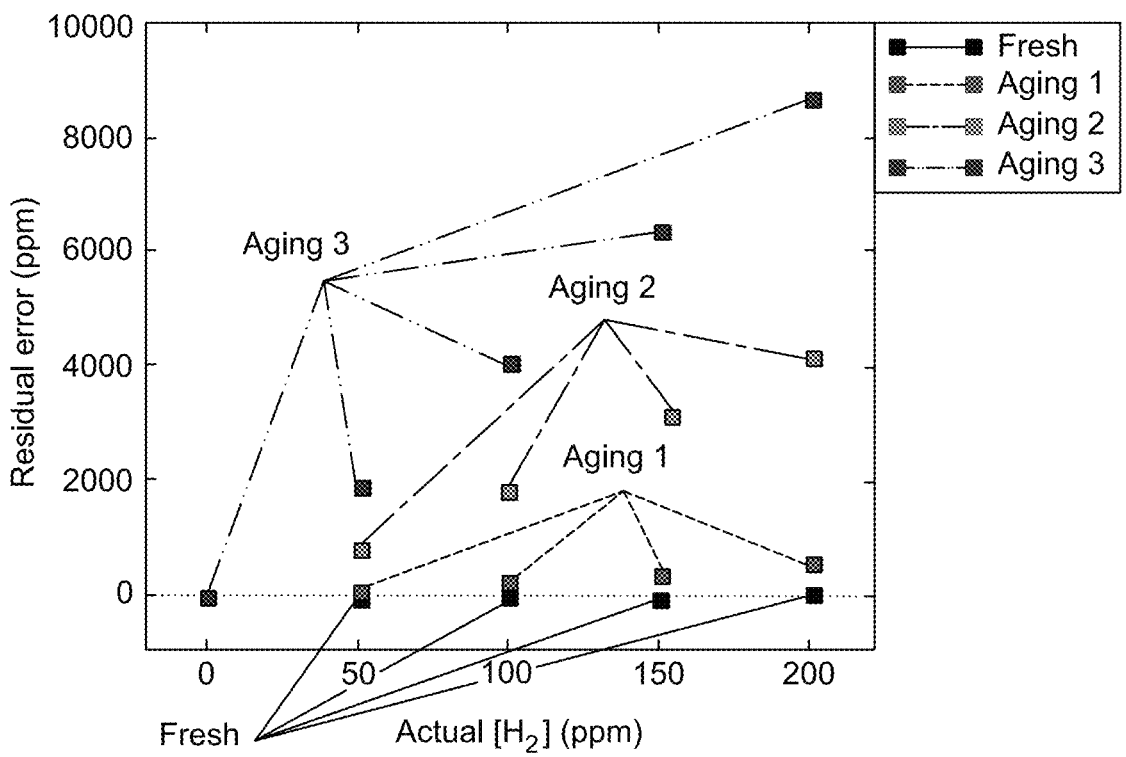
FIG. 30 also depicts use of a transfer function developed for a fresh sensor probe assembly (with no aging)

FIGS. 29 and 30 depict the use of a transfer function developed for a fresh sensor probe assembly (with no aging). FIG. 29 illustrates the correlation plot of the actual versus predicted analyte concentrations measured by the sensor probe assembly, and FIG. 30 illustrates the residual error plot for the sensor responses. This transfer function was used for the response of the fresh sensor probe assembly and also applied the responses of aged sensor probe assemblies after different aging. The predicted concentrations of H2 had significant errors shown in the correlation plot of the actual vs predicted H2 concentrations (FIG. 29) and as the residual error plot (FIG. 30).

Figure 31:
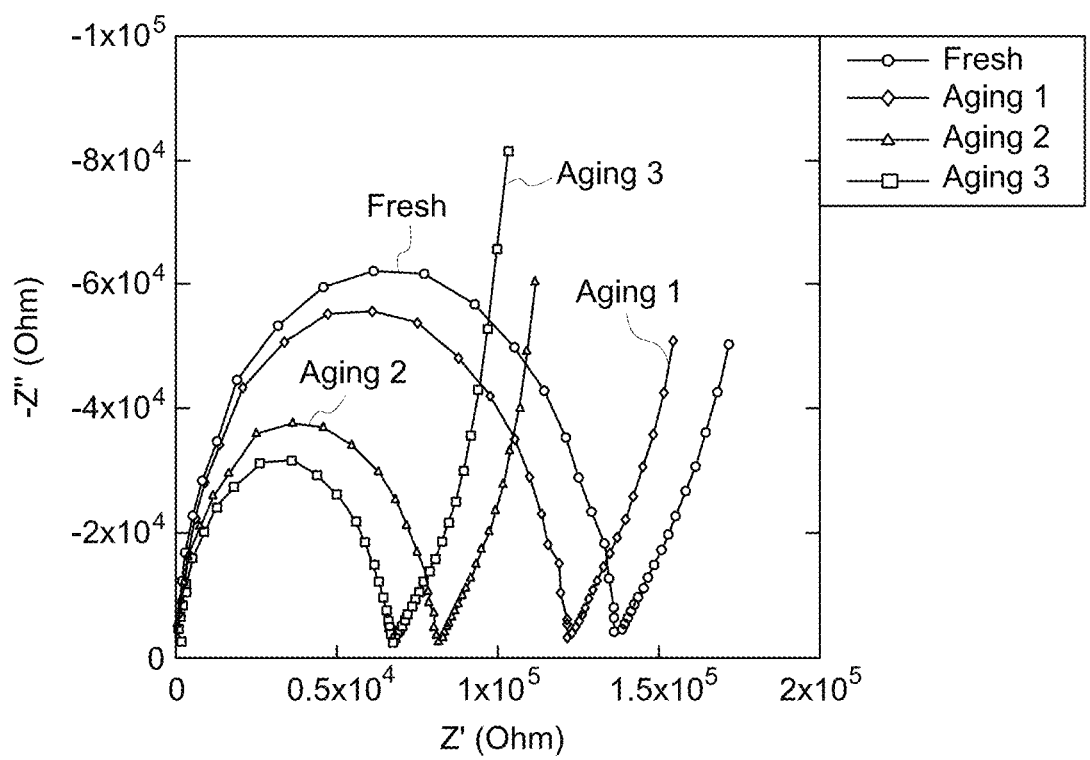
FIG. 31 illustrates a Nyquist plot of the response of the sensor probe assembly before and after three phases of aging.

FIG. 31 illustrates a Nyquist plot of the response of the sensor probe assembly before and after three phases of aging. This plot shows the sensor responses with no aging ("fresh"), with aging of fifteen minutes ("aging 1"), sixty minutes ("aging 2"), and ninety minutes ("aging 3"), as also shown in the other Figures. The aging correction of the sensor response was completed by measuring the impedance response of the sensor probe assembly when the sensor probe assembly was OFF. The Nyquist plot demonstrates the monotonic change in the spectral properties of the sensor probe assembly while the assembly is OFF. These spectral properties were utilized for the correction of the loss of sensor sensitivity to H2 upon aging.

Figure 32:
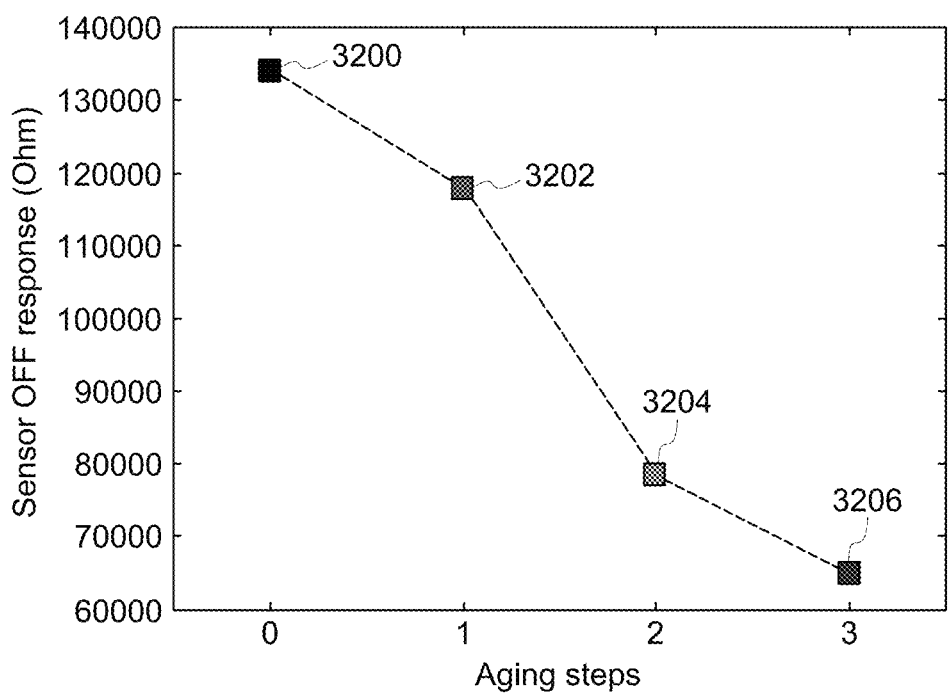
FIG. 32 illustrates the decrease of the sensor response at 100 kHz when the sensor probe assembly was OFF as a function of sensor aging.

Correction of the sensor response for aging effects was performed by selecting a frequency of 100 kHz when the sensor probe assembly was OFF and using the sensor values at that frequency in a transfer function. FIG. 32 illustrates the decrease of the sensor response at 100 kHz when the sensor probe assembly was OFF as a function of sensor aging. Different data points 3200, 3202, 3204, 3206 represent different amounts of aging of the sensor probe assembly, with the data point 3200 representing no aging, the data point 3202 representing aging of fifteen minutes, the data point 3204 representing aging of sixty minutes, and the data point 3206 representing aging of ninety minutes.

These transfer functions for the performance of the sensor probe assembly in H2 responses were further combined with the sensor signal when the sensor probe assembly was powered OFF. The transfer function that included the sensor OFF signal was given by:

$$[H2, ppm] = A_{ON,OFF} * Z_{ON}^{B_{ON,OFF}}$$

Figure 33:
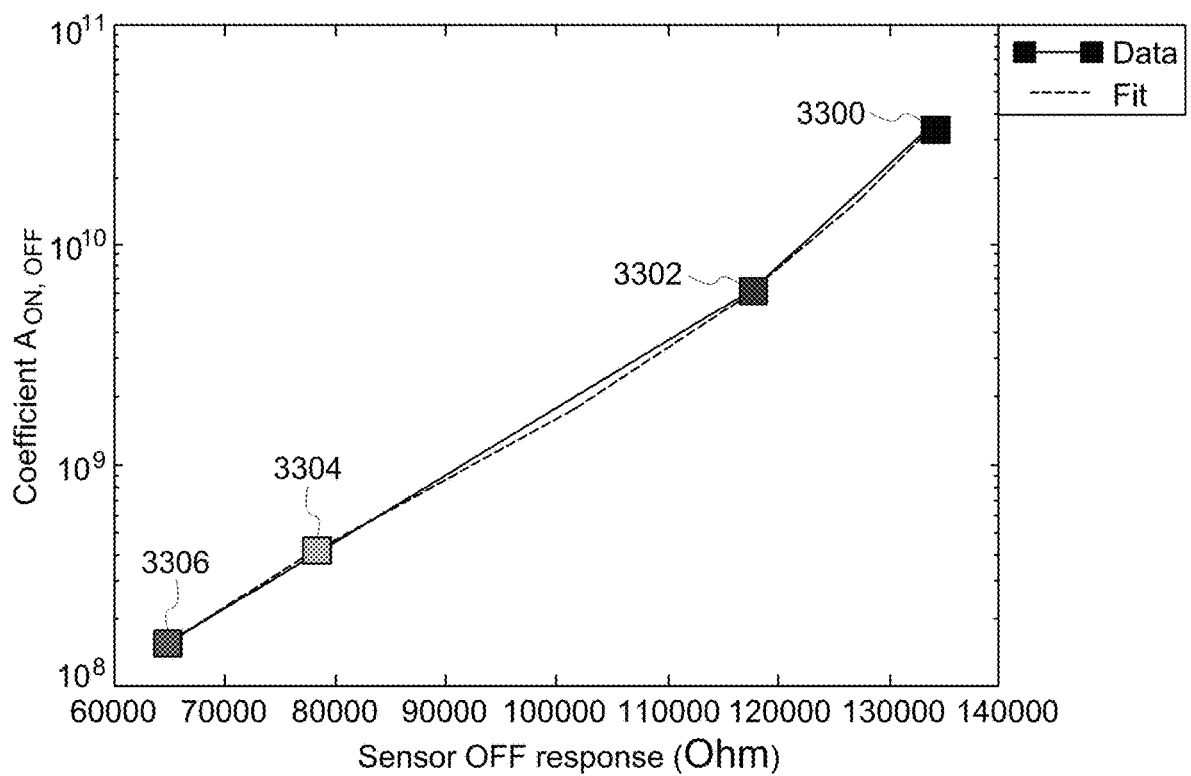
FIG. 33 illustrates the coefficients $A_{ON,\ OFF}$.
Figure 34:
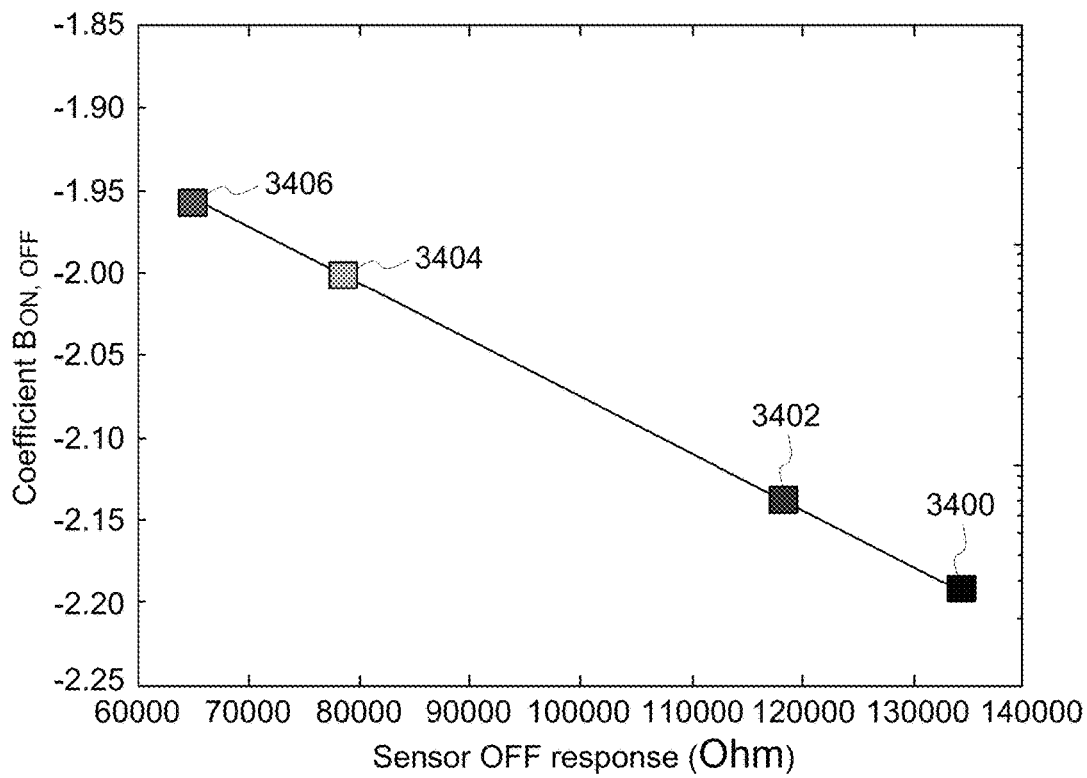
FIG. 34 illustrates the coefficients $B_{ON,\ OFF}$.

The coefficients $A_{ON,\ OFF}$ and $B_{ON,\ OFF}$ of the response to H2 (when the sensor probe assembly is in the ON state, as shown in FIG. 28) were correlated to sensor aging (as determined from the sensor OFF state, as shown in FIG. 32). This correlation was determined by plotting the values of coefficients A or B as a function of the sensor OFF response as depicted in FIGS. 33 and 34. FIGS. 33 and 34 represents the correlation of power law coefficients $A_{ON,\ OFF}$ and $B_{ON,\ OFF}$ of the sensor response to H2 (when the sensor in the ON state) to sensor aging (as determined from the sensor OFF state). FIG. 33 illustrates the coefficients $A_{ON,\ OFF}$ and FIG. 34 illustrates the coefficients $B_{ON,\ OFF}$. Each of FIGS. 33 and 34 includes several data points 3300, 3302, 3304, 3306 (FIG. 33) and 3400, 3402, 3404, 3406 (FIG. 34) represent different amounts of aging of the sensor probe assembly, with the data points 3300, 3400 representing no aging, the data points 3302, 3402 representing aging of fifteen minutes, the data points 3304, 3404 representing aging of sixty minutes, and the data points 3306, 3406 representing aging of ninety minutes. The coefficient $A_{ON,\ OFF}$ was fit with an exponential function and the coefficient $B_{ON,\ OFF}$ was fit with a linear function as a function of sensor aging using sensor OFF responses $Z_{OFF}$.

The fit coefficients included in the responses of the sensor OFF state were defined as follows:

$$A_{ON,OFF} = e^{A_1 \cdot Z_{OFF} + A_2 \cdot Z_{OFF}^2 + A_3 \cdot Z_{OFF}^3 + A_4}$$

$$B_{ON,OFF} = B_1 \cdot Z_{OFF} + B_2$$

where $A_1 = 3.30e-04$, $A_2 = -2.98e-09$, $A_3 = 1.11e-14$, $A_4 = 6.96e+00$, $B_1 = -3.43e-06$, and $B_2 = -1.74e+00$.

Figure 35:
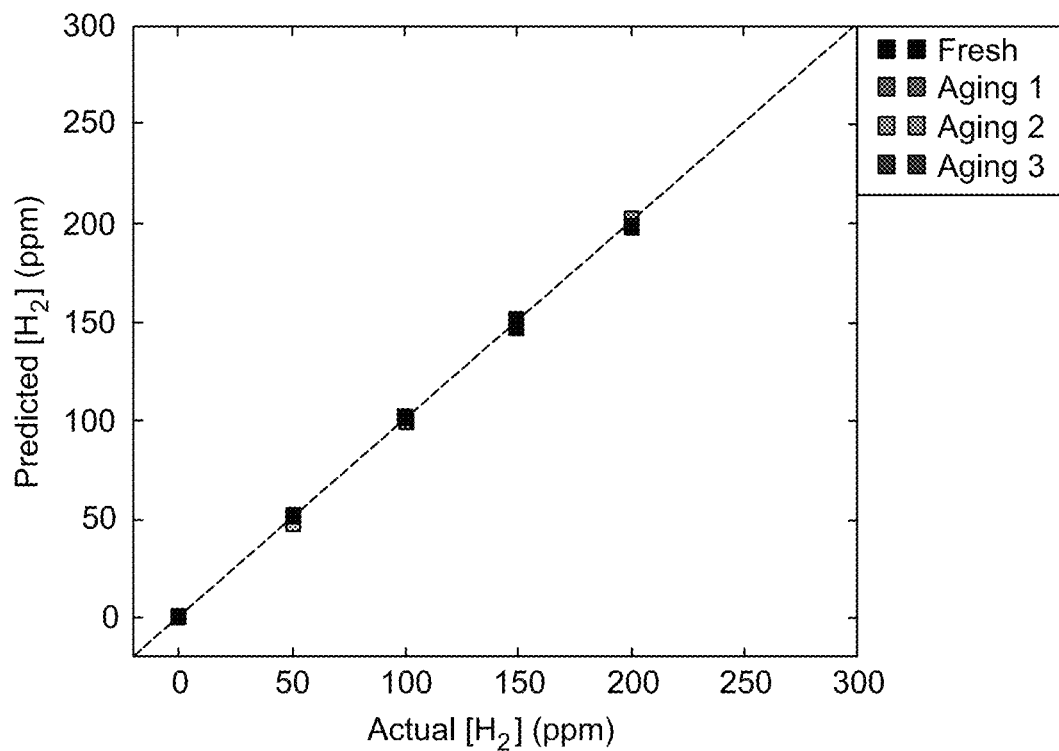
FIG. 35 depicts one example of a prediction ability of the sensor probe assembly upon aging when the new transfer function of the inventive subject matter described herein is applied.
Figure 36:
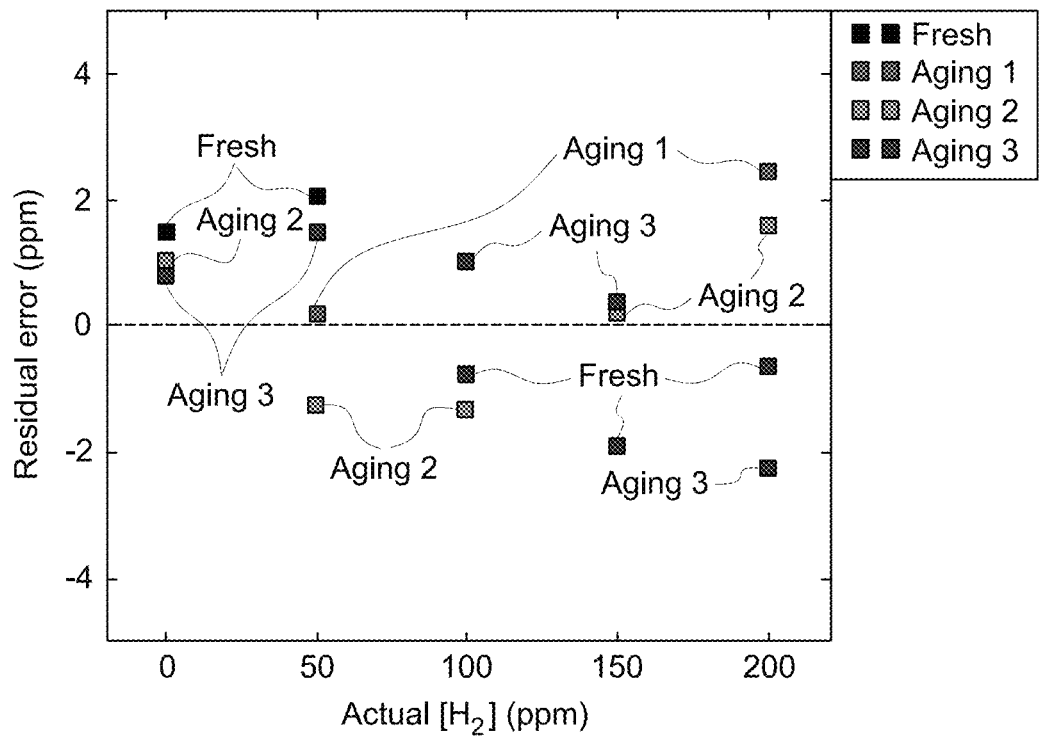
FIG. 36 depicts one example of a prediction ability of the sensor probe assembly upon aging when the new transfer function of the inventive subject matter described herein is applied.

FIGS. 35 and 36 depict one example of a prediction ability of the sensor probe assembly upon aging when the new transfer function of the inventive subject matter described herein is applied. FIG. 35 is a correlation plot between the actual and predicted H2 concentrations for the sensor probe assembly before and after three steps of aging. FIG. 36 are residual errors of predicted H2 concentrations for the sensor probe assembly before and after three steps of aging. The correlation plot between the actual and predicted H2 concentrations for the sensor probe assembly before and after three steps of aging is presented in FIG. 35. The residual errors of predicted H2 concentrations for the sensor before and after three steps of aging are presented in FIG. 36. These results illustrate that the developed concept for the correction of the sensor response upon aging significantly improves sensor performance.

In another experiment, a SnO2 sensor probe assembly was aged by exposing the sensor to oil. The sensor is designed to respond to hydrogen gas. Thus, the sensor was exposed to several concentrations of H2 gas before and after aging. Exposure to oil was performed when the sensor was in the OFF state. The exposure was performed by applying 10 microliters of oil onto the sensor when the sensor was OFF, waiting the oil to spread on the sensor surface and evaporating the oil by turning the sensor ON.

Figure 37:
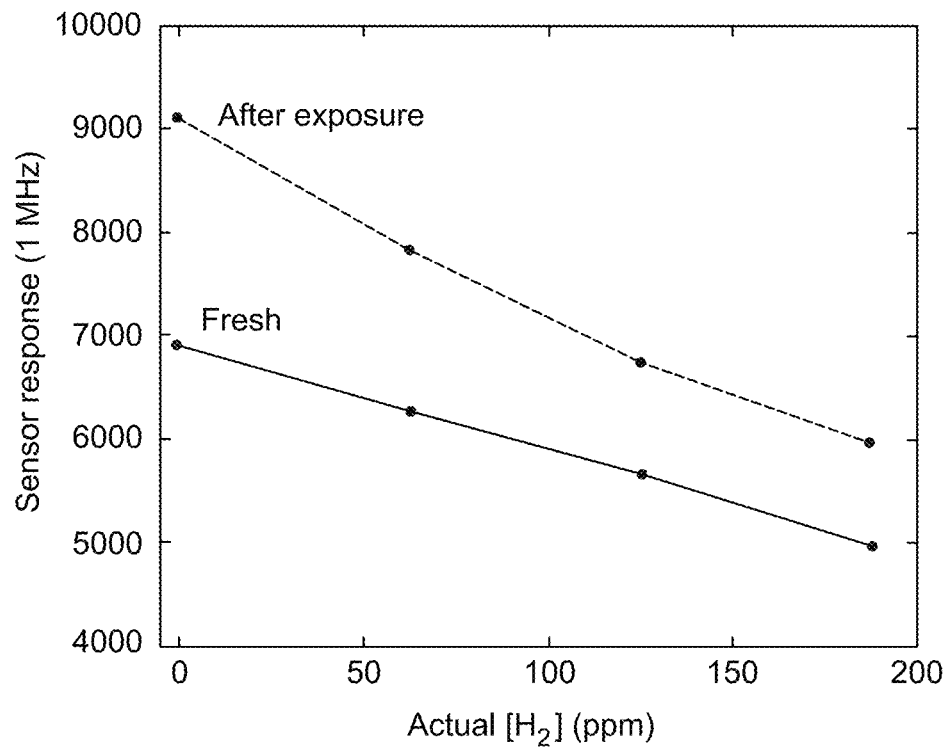
FIG. 37 illustrates the response of the sensor operated in an impedance mode (at 1 MHz, showing the measured imaginary part of the impedance) when the sensor was tested for the sensor response to hydrogen before and after the accelerated aging step.

FIG. 37 illustrates the response of the sensor operated in an impedance mode (at 1 MHz, showing the measured imaginary part of the impedance) when the sensor was tested for the sensor response to hydrogen before and after the accelerated aging step. Before aging, the sensor had a response to H2 that was significantly modified after aging.

Figure 38:
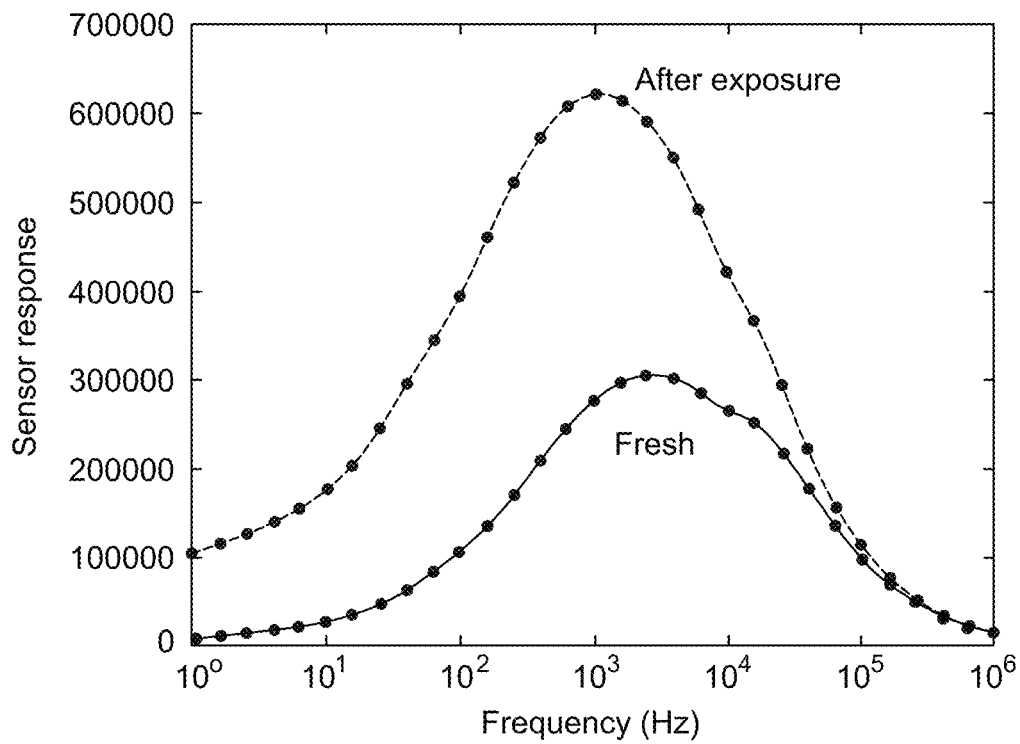
FIG. 38 illustrates the response of the sensor to the ambient environment when the sensor operated in the impedance mode over the range of frequencies from 1 Hz to 1 MHz (with the imaginary part of impedance being measured) when the sensor was tested in ambient air before and after the accelerated aging step.

FIG. 38 illustrates the response of the sensor to the ambient environment when the sensor operated in the impedance mode over the range of frequencies from 1 Hz to 1 MHz (with the imaginary part of impedance being measured) when the sensor was tested in ambient air before and after the accelerated aging step. This response illustrates the frequency range at about 100 to 10,000 Hz where the sensor has the largest response before and after aging.

Figure 39:
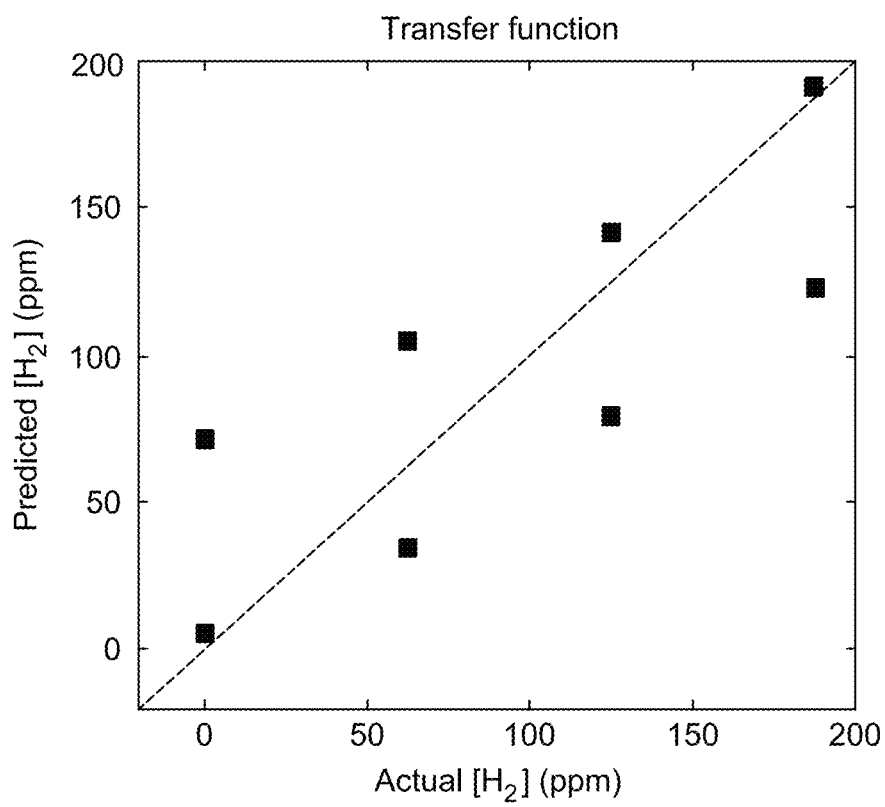
FIG. 39 depicts the response of the sensor to hydrogen when operated in the impedance mode before and after the accelerated aging step and without correction of sensor response when the sensor was in the OFF state.
Figure 40:
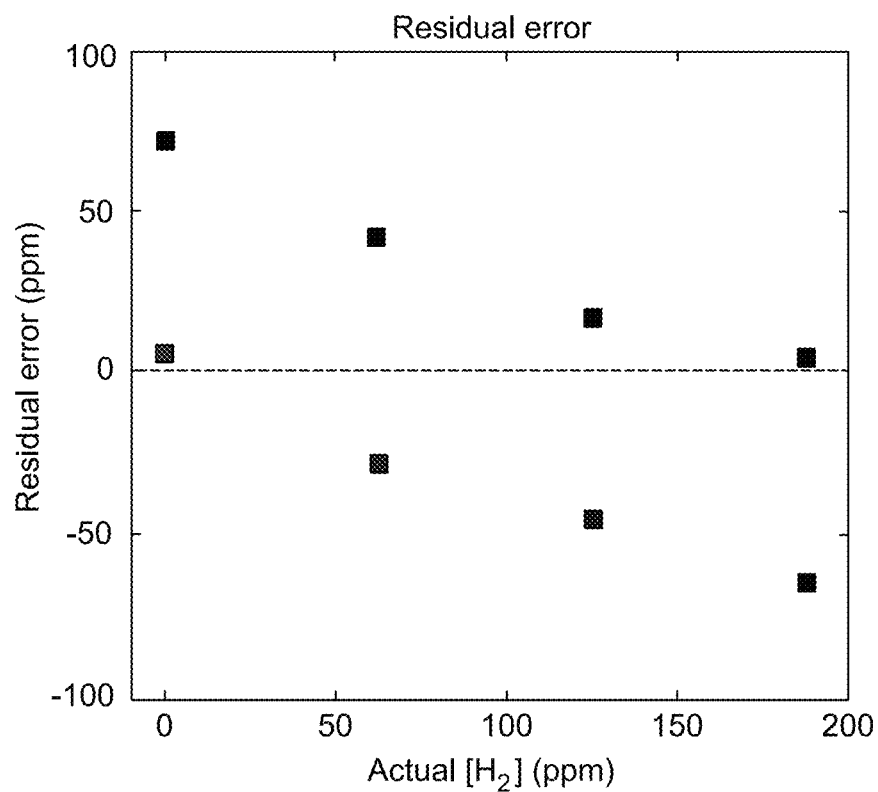
FIG. 40 depicts the response of the sensor to hydrogen when operated in the impedance mode before and after the accelerated aging step and without correction of sensor response when the sensor was in the OFF state.

FIGS. 39 and 40 depict the response of the sensor to hydrogen when operated in the impedance mode before and after the accelerated aging step and without correction of sensor response when the sensor was in the OFF state. FIG. 39 depicts the predicted vs actual concentrations of hydrogen gas before and after the accelerated aging step and without correction of sensor response showing a large spread in predicted values. FIG. 40 depicts the residual error of predictions of concentrations of hydrogen gas before and after the accelerated aging step and without correction of sensor response showing a large spread in residual error values.

Figure 41:
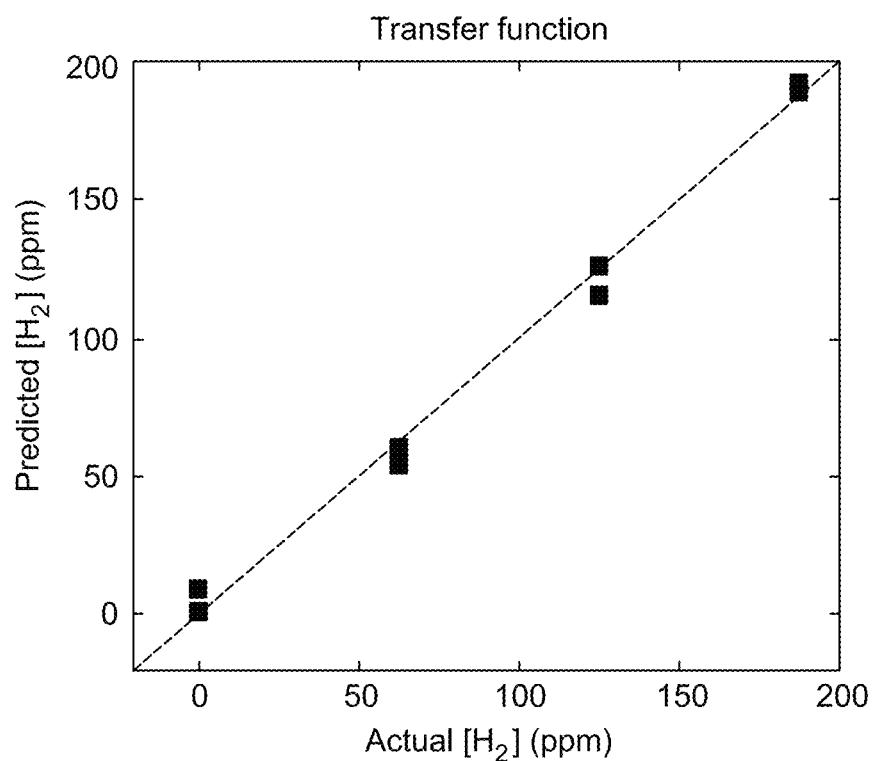
FIG. 41 illustrates predicted versus actual concentrations of hydrogen gas before and after the accelerated aging step and with correction of sensor response showing a relatively small spread in predicted values.
Figure 42:
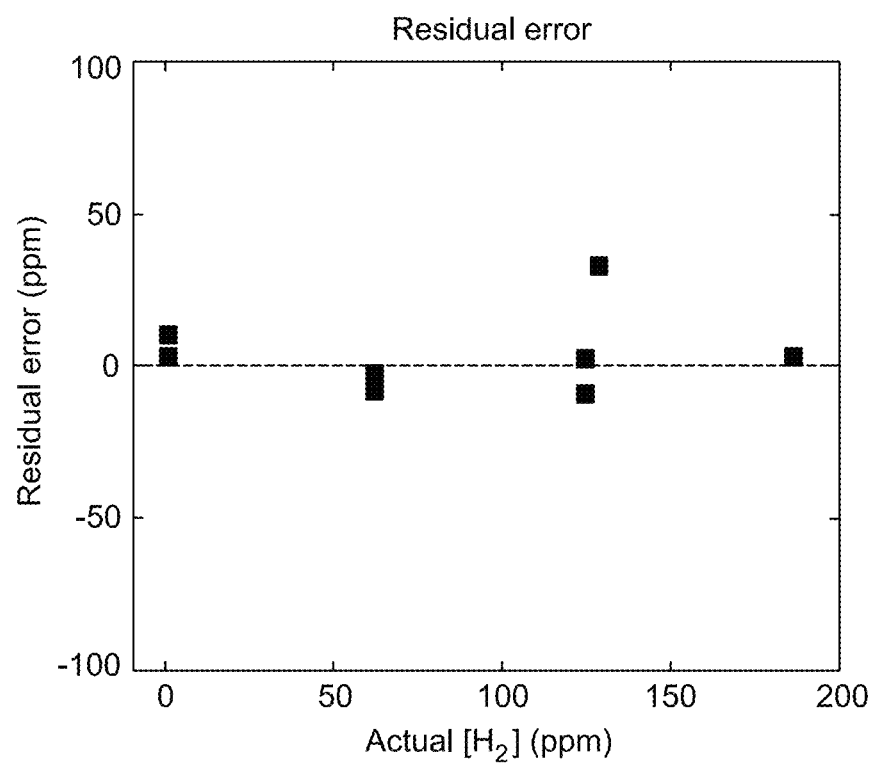
FIG. 42 illustrates residual error of predictions of concentrations of hydrogen before and after an accelerated aging step and with correction of sensor response showing a relatively small spread in residual error values.

FIGS. 41 and 42 illustrate a response of the sensor probe assembly to hydrogen when operated in impedance mode before and after the accelerated aging step with correction of sensor response when the sensor was in OFF state. FIG. 41 illustrates predicted versus actual concentrations of hydrogen gas before and after the accelerated aging step and with correction of sensor response showing a relatively small spread in predicted values. FIG. 42 illustrates residual error of predictions of concentrations of hydrogen before and after accelerated aging step and with correction of sensor response showing a relatively small spread in residual error values.

Figure 43:
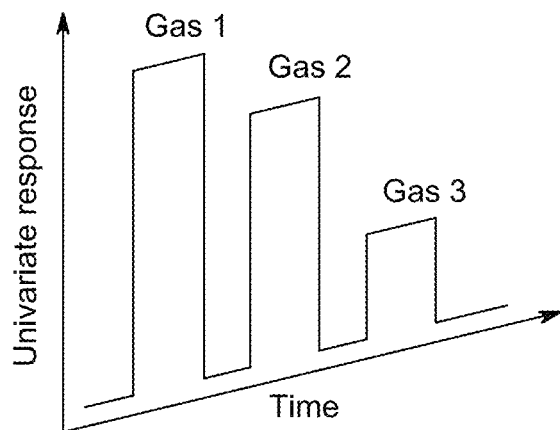
FIG. 43 illustrates a schematic of responses from a conventional sensor to diverse gases that produce only different response magnitudes.
Figure 44:
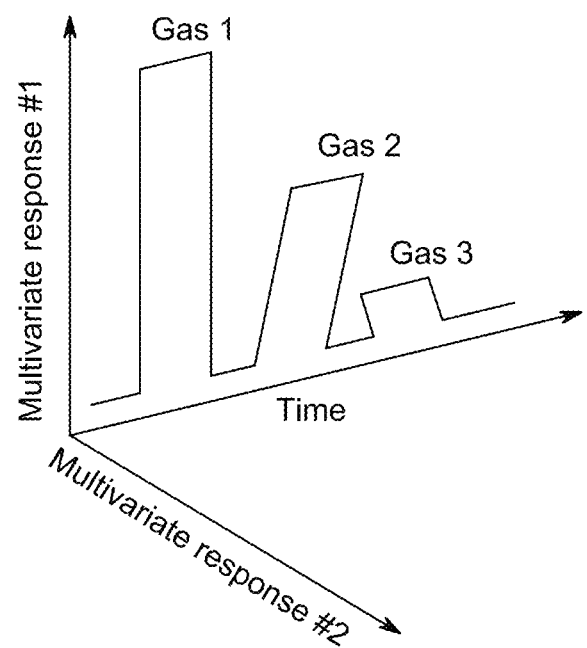
FIG. 44 depicts a schematic of discrimination of gases using a multivariable gas sensor, where the discrimination of gases is not completely orthogonal.
Figure 45:
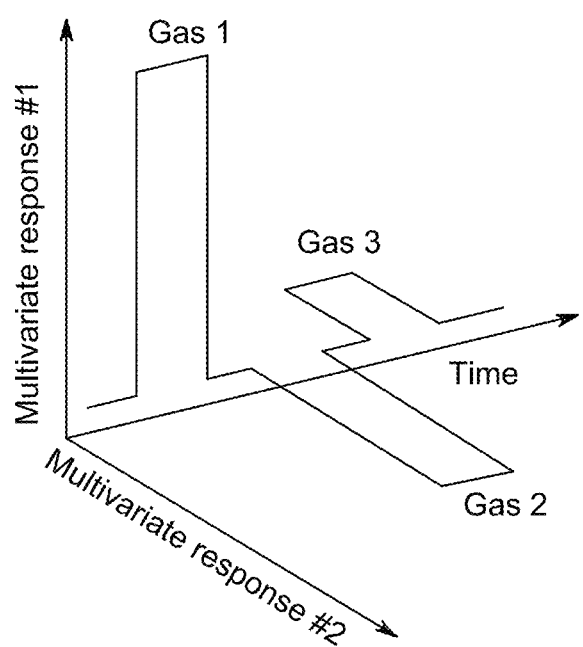
FIG. 45 depicts a schematic of approach of one embodiment of the inventive subject matter described herein for improved orthogonality of response of a multivariable sensor to gases of interest.

Expanding orthogonality of multivariable sensor response can be important in achieving reliable discrimination of different fluids and predicting concentrations of individual fluids in their mixtures. For example, conventional sensors may not discriminate different gases because of the nature of the single-output design principles of the conventional sensors. FIG. 43 illustrates a schematic of responses from a conventional single-output sensor to diverse gases where a conventional single-output sensor produces only different response magnitudes to diverse gases. Thus, when diverse gases are measured at their various concentrations using a conventional single-output sensor, same response magnitudes may be obtained without providing any information about was the particular gas that produced such response. Discrimination of gases can be achieved using multivariable sensors. FIG. 44 depicts a schematic of discrimination of gases using a multivariable gas sensor, where the discrimination of gases is not completely orthogonal, limiting analysis of multiple individual gases or gas mixtures. One or more embodiments of the inventive subject matter described herein improves the orthogonality of responses of a multivariable sensor to gases of interest. FIG. 45 depicts a schematic of approach of the inventive subject matter described herein for improved orthogonality of response of a multivariable sensor to gases of interest.

Figure 46:
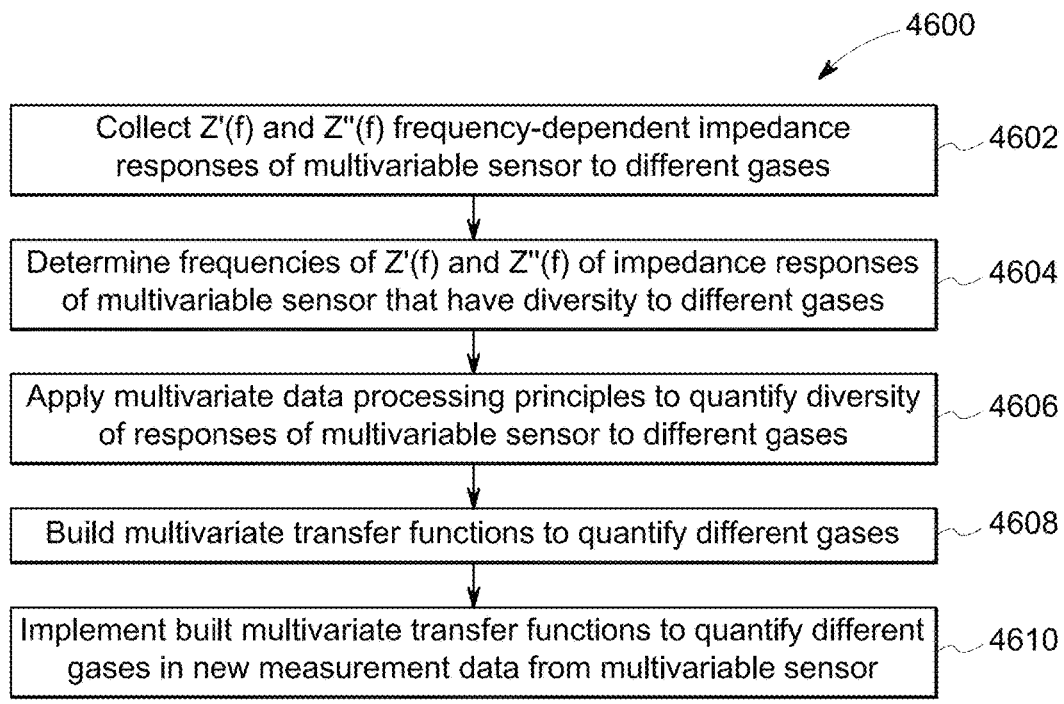
FIG. 46 illustrates one embodiment of a method for quantitation of different gases using a multivariable sensor.

In one embodiment, one embodiment of a method for quantitation of different gases using a multivariable sensor is depicted in FIG. 46. The operations described in connection with this method can be performed partially or entirely by the data acquisition circuitry described herein. In this method, frequency-dependent impedance responses of a multivariable sensor $Z'(f)$ and $Z''(f)$ to different gases are collected at 4602. Next, frequencies of $Z'(f)$ and $Z''(f)$ of impedance responses of a multivariable sensor are determined that have diversity to different gases at 4604. Next, multivariate data processing principles are applied to quantify diversity of responses of a multivariable sensor to different gases at 4606. Next, multivariate transfer functions are built to quantify different gases at 4608. Finally, these built multivariate transfer functions are implemented to quantify different gases in new measurement data from this multivariable sensor at 4610.

For example, at any measured frequency f1, the multivariable sensor can have a response $Z'(f1)$ and $Z''(f1)$ to gas 1 as $Z'(gas1\ at\ f1)$ and $Z''(gas1\ at\ f1)$. Similarly, the multivariable sensor can have its response $Z'(f1)$ and $Z''(f1)$ to gas 2 as $Z'(gas2\ at\ f1)$ and $Z''(gas2\ at\ f1)$.

Response pattern of the multivariable sensor to gas 1 and gas 2 can be defined as the different ratios of responses of $Z'(f1)$ and $Z''(f1)$ such as:

$Z'(gas1\ at\ f1)/Z'(gas2\ at\ f1)$, or $Z''(gas1\ at\ f1)/Z''(gas2\ at\ f1)$, or $Z'(gas1\ at\ f1)/Z''(gas2\ at\ f1)$, or $Z''(gas1\ at\ f1)/Z'(gas2\ at\ f1)$.

Other ratios between responses are also possible, for example when the responses are combinations of more than two frequencies. If the response pattern of the multivariable sensor to gas 1 and gas 2 stays the same for all measured frequencies, this means that this multivariable sensor does not have a diversity in response to gas 1 and gas 2 and thus, gas 1 and gas 2 cannot be discriminated with this multivariable sensor at these measurement conditions.

However, if the response pattern of the multivariable sensor to gas 1 and gas 2 is different for some or all measured frequencies, this means that this multivariable sensor has diversity in response to gas 1 and gas 2 and these two gases can be discriminated with this multivariable sensor at these measurement conditions.

Nonlimiting examples of multivariate data processing principles include methods to perform quantitation of gases. Nonlimiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), or Neural Network Analysis (NNA).

Figure 47:
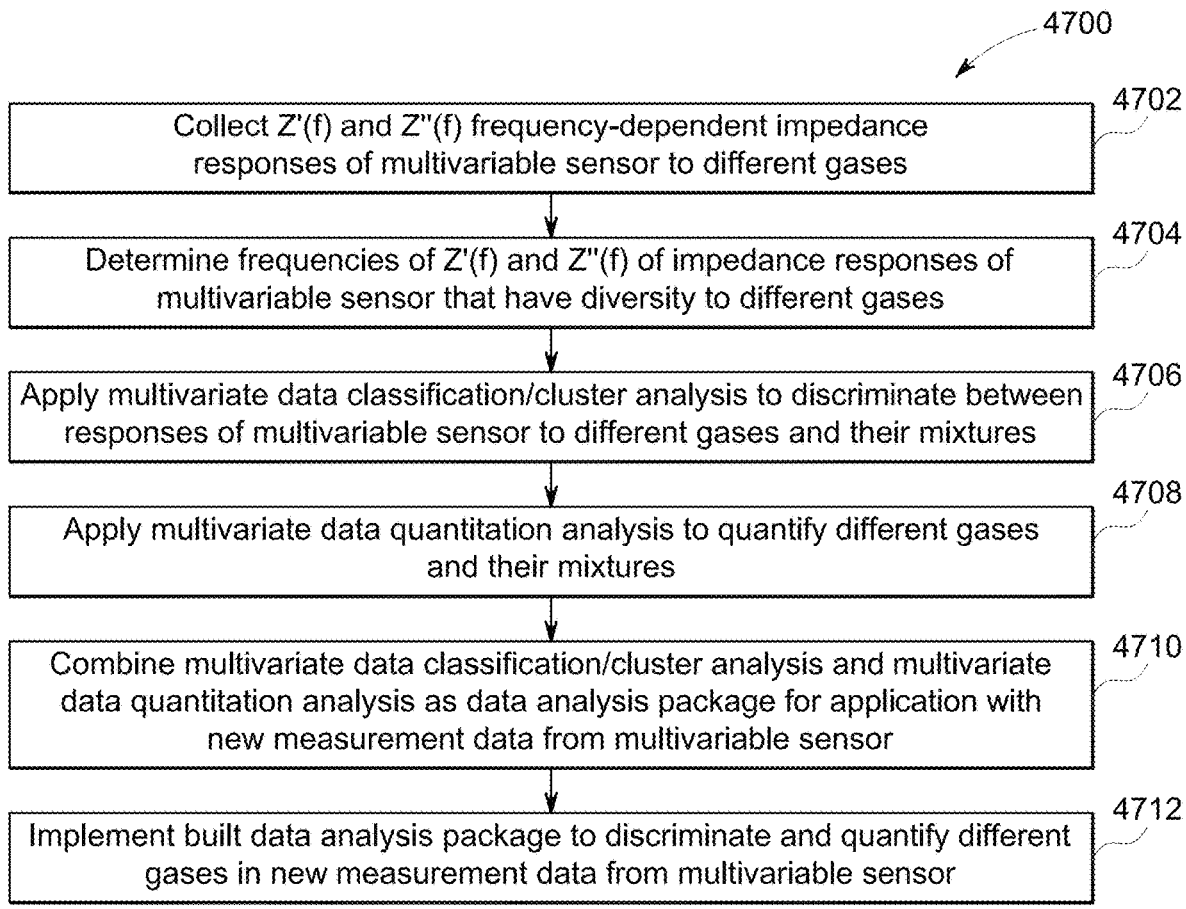
FIG. 47 illustrates one embodiment of a method for classification and quantitation of different gases using a multivariable sensor.

In one embodiment, a method for classification and quantitation of different gases using a multivariable sensor is depicted in FIG. 47. The operations described in connection with this method can be performed partially or entirely by the data acquisition circuitry described herein. In this method, frequency-dependent impedance responses of a multivariable sensor Z'(f) and Z"(f) to different gases are collected (at 4702). Next, frequencies of Z'(f) and Z"(f) of impedance responses of a multivariable sensor are determined that have diversity to different gases (at 4704). Next, multivariate data classification/cluster analysis is applied to discriminate between responses of multivariable sensor to different gases and mixtures of the gases (at 4706). Next, multivariate data quantitation analysis is applied to quantify different gases and mixtures of the gases (at 4708). Next, multivariate data classification/cluster analysis and multivariate data quantitation analysis are combined to produce a data analysis package for application with new measurement data from the multivariable sensor (at 4710). Finally, the built data analysis package is implemented to discriminate and quantify different gases in new measurement data from multivariable sensor (at 4712).

Nonlimiting examples of multivariate data processing principles include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis methods include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Nonlimiting examples of methods for performing analyte quantitation to determine the concentration of a particular analyte gas include Principal Component Regression (PCR) and Independent Component Regression (ICR). In certain aspects of the inventive subject matter described herein, a classification algorithm can be followed by quantitation algorithm.

Figure 48:
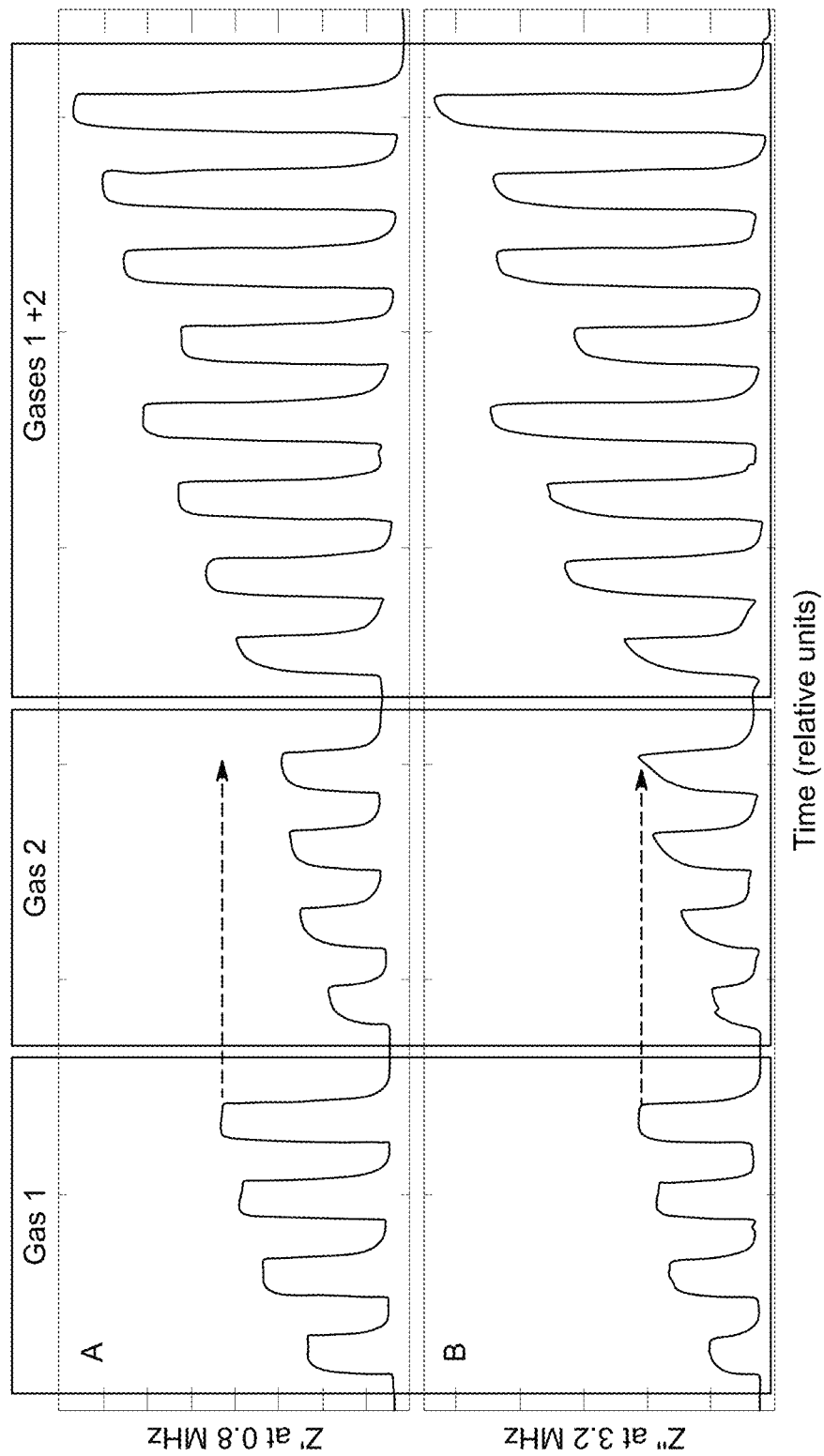
FIG. 48 illustrates an example of detection of acetylene C2H2 (gas 1) and water vapor (H2O, gas 2) and mixtures of these components using an impedance sensor according to one embodiment of the inventive subject matter described herein.

FIG. 48 illustrates an example of detection of acetylene C2H2 (gas 1) and water vapor (gas 2) and their mixtures (gas 1+2) diluted with air using an impedance sensor of this invention. The sensor utilized a semiconducting metal oxide as a sensing material such as tin dioxide SnO2. Using a computer-controlled gas dilution and mixing system, four concentrations of C2H2 (gas 1) were generated such as 312.5 ppm (1), 625 ppm (2), 937.5 ppm (3), and 1250 ppm (4); four concentrations of $H_2O$ (water vapor, gas 2) were generated such as $5.3 \times 10^3$ ppm (1), $1.1 \times 10^4$ ppm (2), $1.6 \times 10^4$ ppm (3), and $2.1 \times 10^4$ ppm (4); and eight mixtures of gas 1 and gas 2 were generated such as:

312.5 ppm of C2H2 and $5.3 \times 10^3$ ppm of $H_2O$ (mixture 1),
312.5 ppm of C2H2 and $1.6 \times 10^4$ ppm of $H_2O$ (mixture 2),
625 ppm of C2H2 and $1.1 \times 10^4$ ppm of $H_2O$ (mixture 3),
625 ppm of C2H2 and $2.1 \times 10^4$ ppm of $H_2O$ (mixture 4),
937.5 ppm of C2H2 and $5.3 \times 10^3$ ppm of $H_2O$ (mixture 5),
937.5 ppm of C2H2 and $1.6 \times 10^4$ ppm of $H_2O$ (mixture 6),
1250 ppm of C2H2 and $1.1 \times 10^4$ ppm of $H_2O$ (mixture 7),
1250 ppm of C2H2 and $2.1 \times 10^4$ ppm of $H_2O$ (mixture 8).

Concentrations of gases were presented to the sensor in sequence with a blank (clean air) between exposures to gases. Results depicted in FIG. 48 illustrate detection of acetylene C2H2 and $H_2O$ and their mixtures. For example, Graph A illustrates the sensor response Z' at 0.8 MHz and Graph B illustrates the sensor response Z" response at 3.2 MHz. Each Graph A and Graph B includes a horizontal dotted arrow line. These lines highlight the response magnitudes of the sensor to the highest tested C2H2 concentration and compare these response magnitudes with the response magnitudes of the sensor to tested $H_2O$ concentrations. Graph A demonstrates that at the illustrated frequency, Z' sensor response has bigger magnitude to C2H2 as compared to H2O. However, as demonstrated in Graph B, at the illustrated frequency Z" sensor response has same magnitude to C2H2 and H2O. Thus, operation of the impedance sensor at different frequencies and detection at Z' and Z" provides different response patterns to C2H2 and H2O and their mixtures where the relative response magnitudes to C2H2 and H2O are varied depending on the detection frequency and Z' or Z" operation.

Figure 49:
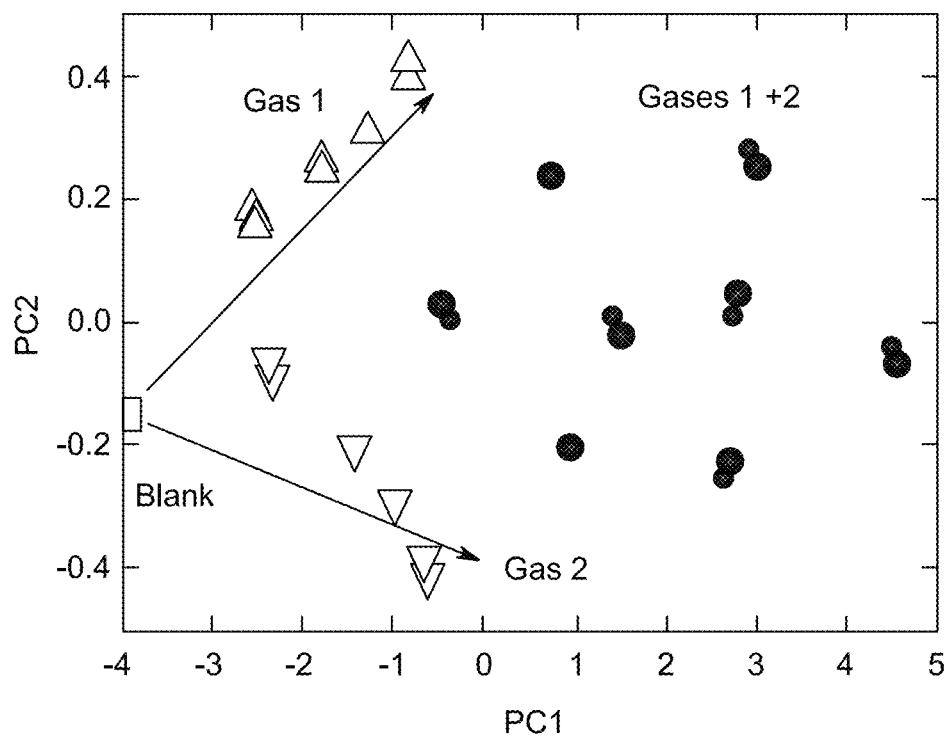
FIG. 49 depicts a scores plot of principal component 1 vs principal component 2 of a built principal component analysis model that discriminates between individual gases and mixtures of these gases based on Z' and Z'' spectral features of a single multivariable sensor according to one embodiment of the inventive subject matter described herein.

Several frequencies were used to build a multivariate model using principal components analysis (PCA) tool. PCA is a widely accepted unsupervised pattern recognition technique for classification of multivariate data. PCA reduces a multidimensional data set for its easier interpretation. PCA calculates orthogonal principal components (PCs) that are oriented in the direction of the maximum variance within the data set. The first principal component contains the highest degree of variance, and other PCs follow in the order of decreasing variance. Thus, the PCA concentrates the most significant characteristics (variance) of the data into a lower dimensional space. The distribution of data points in the PCA plot allows the visualization of relations between the original impedance spectra. FIG. 49 illustrates a two-dimensional plot of a first principal component (PC1) versus a second principal component (PC2). This score plot of PCs visualizes the response pattern of the sensor to different gases and their mixtures based on their Z' and Z" spectral features. Such plot illustrates that PCA response of a single impedance sensor based on a SnO2 sensing material starts from the response to a blank (clean air) and is further directed into different directions that are dependent on the type of detected gas 1 and gas 2 and mixtures of gas 1 and gas 2.

Figure 50:
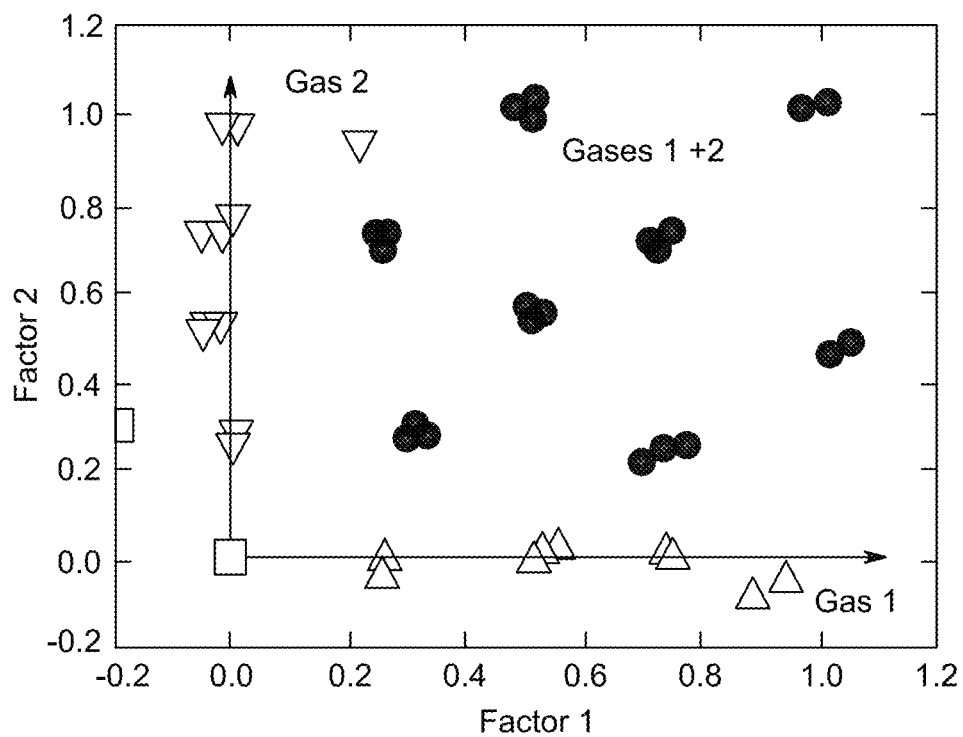
FIG. 50 depicts a plot of factor 1 vs factor 2 of the built model that produces orthogonal response to different individual gases 1 and 2 to discriminate mixtures of gases 1 and 2 with an improved linearity over principal component analysis (PCA)

FIG. 50 depicts a plot of factor 1 vs factor 2 of the built model. This plot illustrates the ability to produce orthogonal response to different individual gases 1 and 2 to discriminate mixtures of gases 1 and 2 with an improved linearity over PCA.

Figure 51:
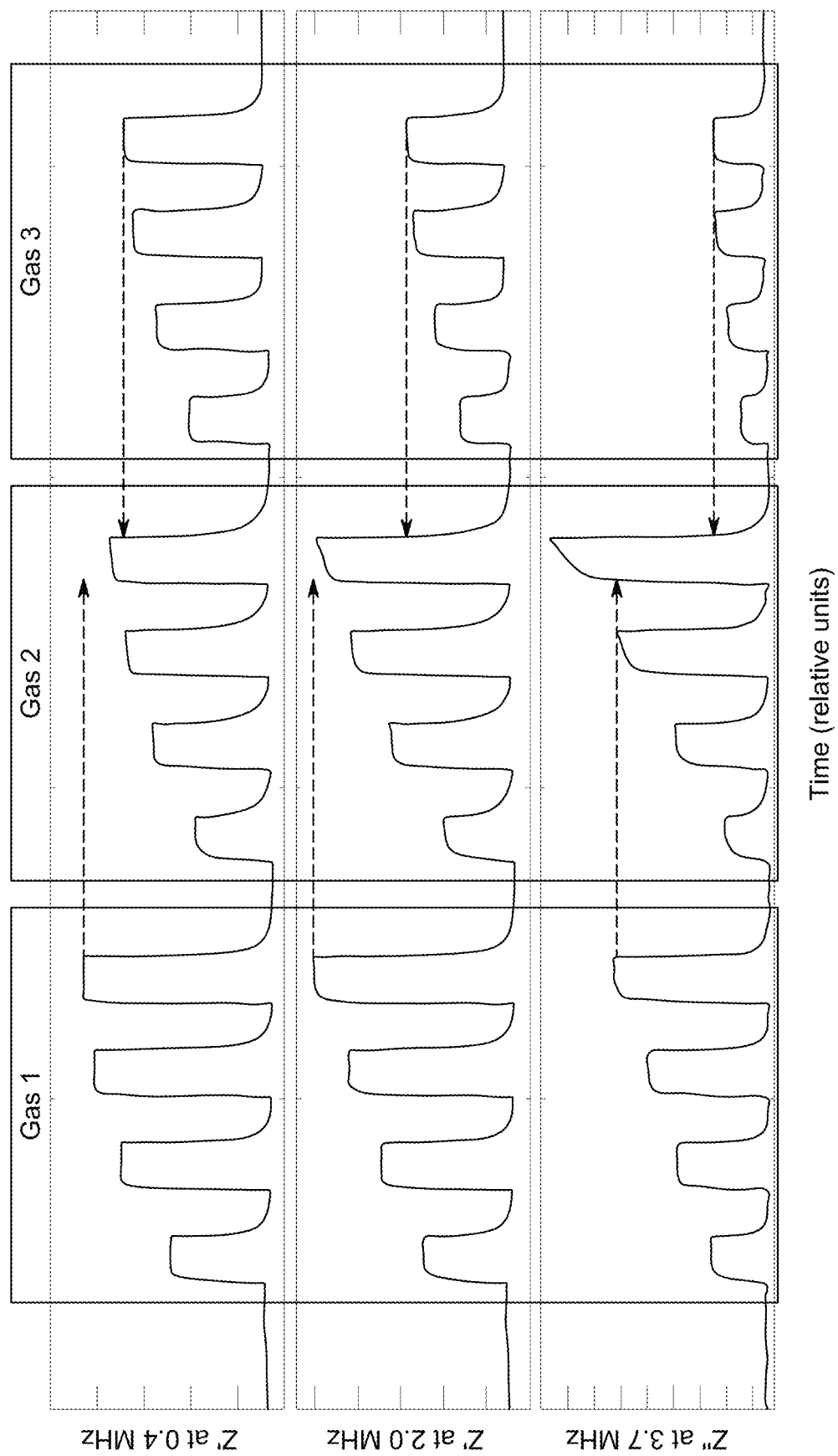
FIG. 51 illustrates an example detection of acetylene C2H2 as gas 1, hydrogen H2 as gas 2, and methane CH4 as gas 3 using one embodiment of an impedance sensor of the inventive subject matter described herein.

FIG. 51 illustrates an example of detection of three gases with a single multivariable sensor. The sensor utilized a semiconducting metal oxide such as tin dioxide SnO2 as a sensing material. The example gases were acetylene C2H2 as gas 1, hydrogen H2 as gas 2, and methane CH4 as gas 3. Using a computer-controlled gas dilution and mixing system, four concentrations of each gas were generated.

Gas 1 had concentrations 1042 ppm (1), 2083 ppm (2), 3125 ppm (3), and 4167 ppm (4). Gas 2 had concentrations 4 ppm (1), 8 ppm (2), 13 ppm (3), and 17 ppm (4).

Gas 3 had concentrations 2083 ppm (1), 4167 ppm (2), 6250 ppm (3), and 8333 ppm (4).

Gas concentrations were presented to the sensor in sequence with a blank (clean air) between exposures to gases. Graph A illustrates the sensor response Z' at 0.4 MHz, Graph B illustrates the sensor response Z' at 2.0 MHz, and Graph C illustrates the sensor response Z" at 3.7 MHz. Each Graph A through C includes two horizontal dotted arrow lines. Left lines go from gas 1 to gas 2 to highlight the response magnitude of the sensor to the highest tested concentration of gas 1 and to compare this response magnitude with the response magnitude of the sensor to tested concentrations of gas 2. Right lines go from gas 3 to gas 2 to highlight the response magnitude of the sensor to the highest tested concentration of gas 3 and to compare this response magnitude with the response magnitude of the sensor to tested concentrations of gas 2.

Graph A demonstrates that at the illustrated frequency, Z' sensor response to gas 1 has approximately similar magnitude as compared to response magnitude to gas 2 and sensor response to gas 3 has approximately similar magnitude as compared to response magnitude to gas 2. Graph B demonstrates that at the illustrated frequency, Z' sensor response to gas 1 has approximately similar magnitude as compared to response magnitude to gas 2 and sensor response to gas 3 has smaller magnitude as compared to response magnitude to gas 2. Graph C demonstrates that at the illustrated frequency, Z' sensor response to gas 1 has smaller magnitude as compared to response magnitude to gas 2 and sensor response to gas 3 has smaller magnitude as compared to response magnitude to gas 2. Thus, operation of the impedance sensor at different frequencies and detection at Z' and Z'' provides different response patterns to gas 1, gas 2, and gas 3 where the relative response magnitudes to gas 1, gas 2, and gas 3 are varied depending on the detection frequency and Z' or Z'' operation.

As shown in FIG. 51, the sensor responses to gas 1, gas 2, and gas 3 had different relative magnitudes with respect to each other as illustrated at different frequencies and as measured as Z' or Z''. To visualize this frequency dependence of sensor responses to gas 1, gas 2, and gas 3, correlation matrices were created with rows and columns that were frequencies of Z'' responses of the sensor. These correlation matrices were depicting difference of the sensor responses between pairs of gases such as gas 1 vs gas 2, gas 1 vs gas 3, and gas 2 vs gas 3. The frequencies were from 100 Hz to about 10 MHz with the total number of 75 frequencies. The color maps were visualizing regions of response difference of the sensor between pairs of gases such as gas 1 vs gas 2, gas 1 vs gas 3, and gas 2 vs gas 3. Regions without significant response difference had values of about zero, while regions with significant response difference had values from about 0.5 to about unity.

Figure 52:
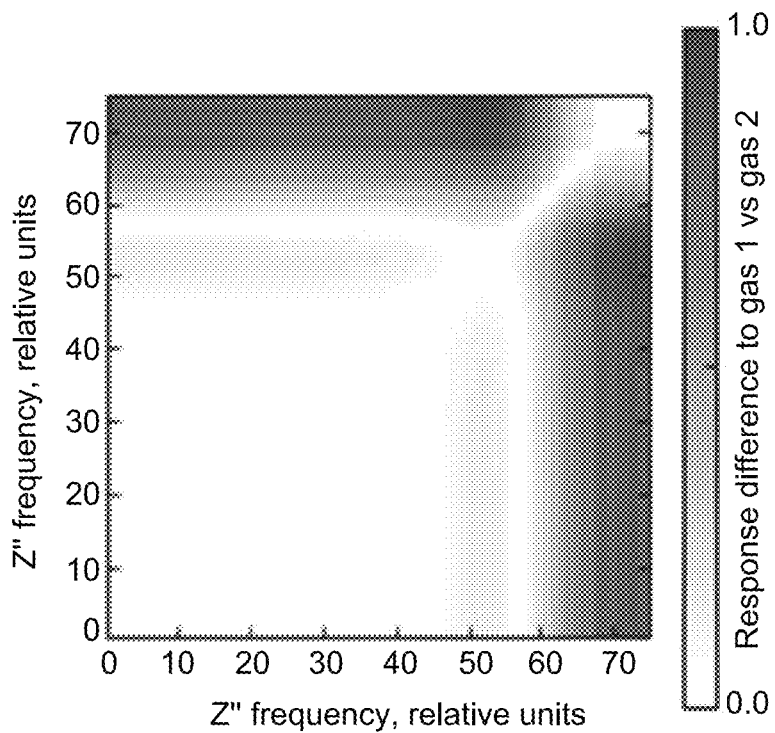
FIG. 52 illustrates a correlation matrix of the sensor response to gas 1 in relation to the sensor response to gas 2.

FIG. 52 illustrates a correlation matrix that depicts the diversity of the sensor response at different frequencies to gas 1 in relation to the sensor response at different frequencies to gas 2. The map visualizes regions of response difference for pairs of frequencies. The significant response difference of the sensor between gas 1 vs gas 2 was observed when the region of frequencies starting from about frequency 65 to about frequency 75 was paired with the region of frequencies starting from about frequency 1 to about frequency 60.

Figure 53:
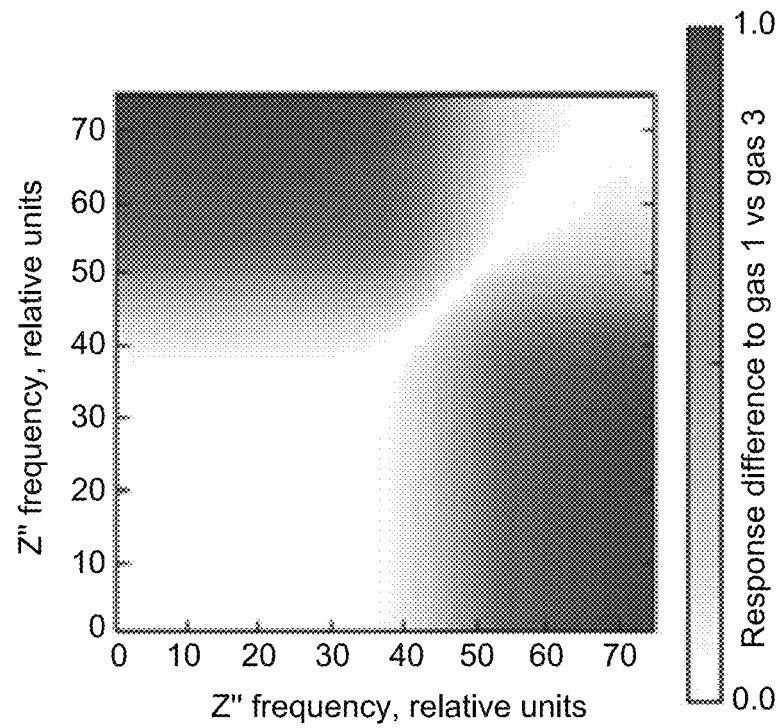
FIG. 53 illustrates a correlation matrix of the sensor response to gas 1 in relation to the sensor response to gas 3.

FIG. 53 illustrates a correlation matrix that depicts the diversity of the sensor response at different frequencies to gas 1 in relation to the sensor response at different frequencies to gas 3. The map visualizes regions of response difference for pairs of frequencies. The significant response difference of the sensor between gas 1 vs gas 3 was observed when the region of frequencies starting from about frequency 45 to about frequency 75 was paired with the region of frequencies starting from about frequency 1 to about frequency 50.

Figure 54:
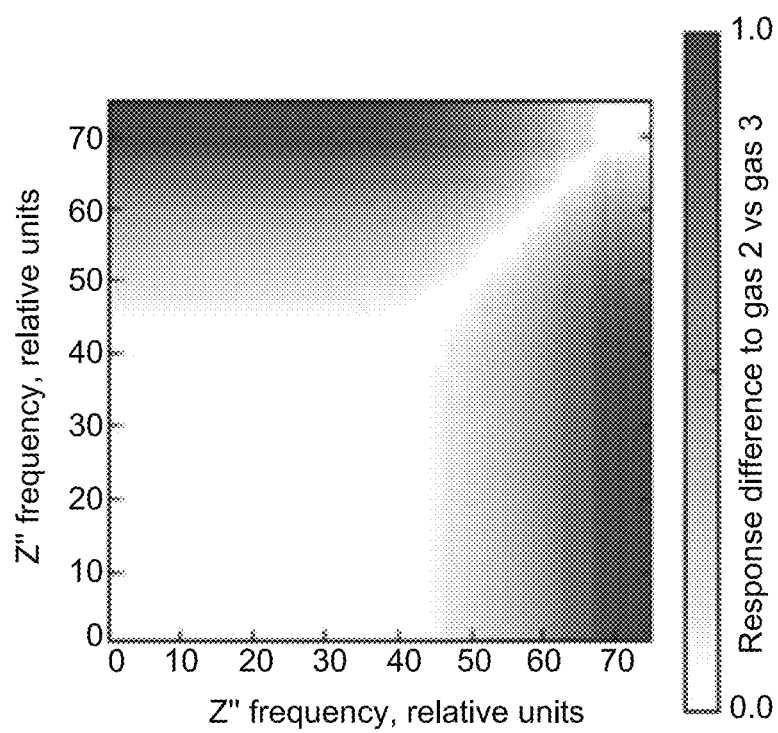
FIG. 54 illustrates a correlation matrix of the sensor response to gas 2 in relation to the sensor response to gas 3.

FIG. 54 illustrates a correlation matrix that depicts the diversity of the sensor response at different frequencies to gas 2 in relation to the sensor response at different frequencies to gas 3. The map visualizes regions of response difference for pairs of frequencies. The significant response difference of the sensor between gas 2 vs gas 3 was observed when the region of frequencies starting from about frequency 65 to about frequency 75 was paired with the region of frequencies starting from about frequency 1 to about frequency 60.

These correlation matrices depicted in FIG. 52, FIG. 53, and FIG. 54 demonstrated that the developed multivariable sensor had diverse responses to gas 1, gas 2, and gas 3 over the broad range of frequencies. These diverse responses to gas 1, gas 2, and gas 3 allowed the discrimination between these gases with a single multivariable sensor.

Figure 55:
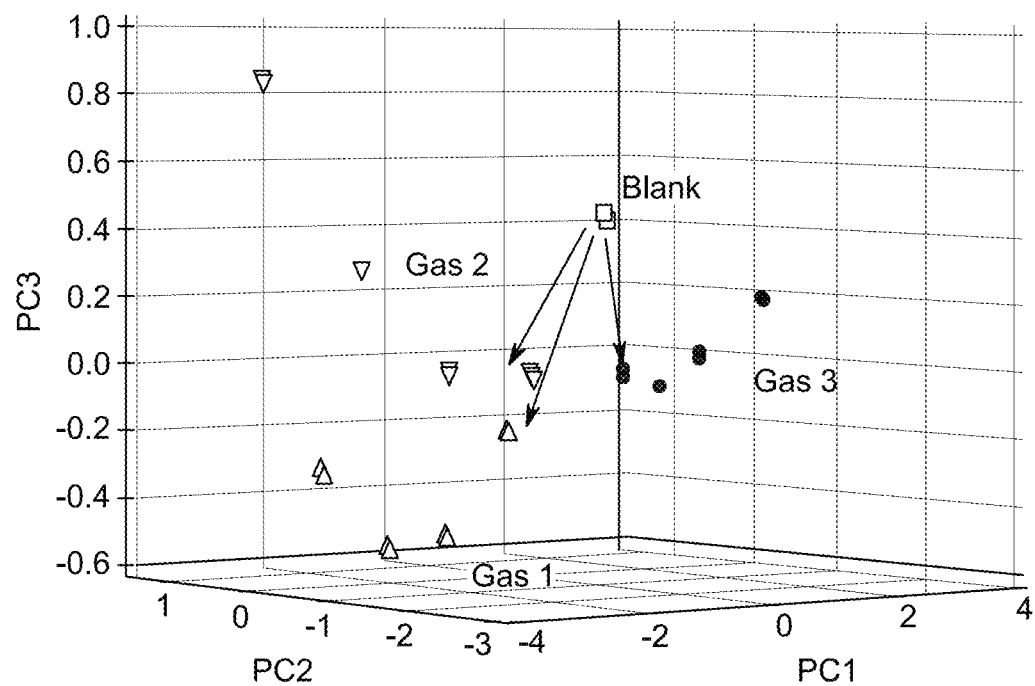
FIG. 55 depicts a scores plot of principal component 1 vs principal component 2 vs principal component 3 of the built principal component analysis model that discriminates between three individual gases such acetylene C2H2 (gas 1), hydrogen H2 (gas 2), and methane CH4 (gas 3) based on the Z' and Z'' spectral features of a single multivariable sensor.

Several frequencies were used to build multivariate models that enabled visualization of how the multivariate sensor responds to gas 1, gas 2, and gas 3. One multivariate model was built using PCA. FIG. 55 illustrates a three-dimensional plot of a first principal component (PC1) versus a second principal component (PC2) and versus a third principal component (PC3). This score plot of PCs visualizes the response pattern of the sensor to gas 1, gas 2, and gas 3 based on their Z' and Z'' spectral features. Acetylene C2H2 was gas 1, hydrogen H2 was gas 2, and methane CH4 was gas 3. Such plot illustrates that PCA response of a single impedance sensor based on a SnO2 sensing material starts from the response to a blank (clean air) and is further directed into different directions that are dependent on the type of detected gas 1, gas 2, and gas 3. FIG. 55 illustrates that PCA response of a single impedance sensor based on a SnO2 sensing material has a high response dimensionality such as three dimensions. The higher the response dimensionality, the differentiation between the gases improves relative to lower response dimensionality.

Figure 56:
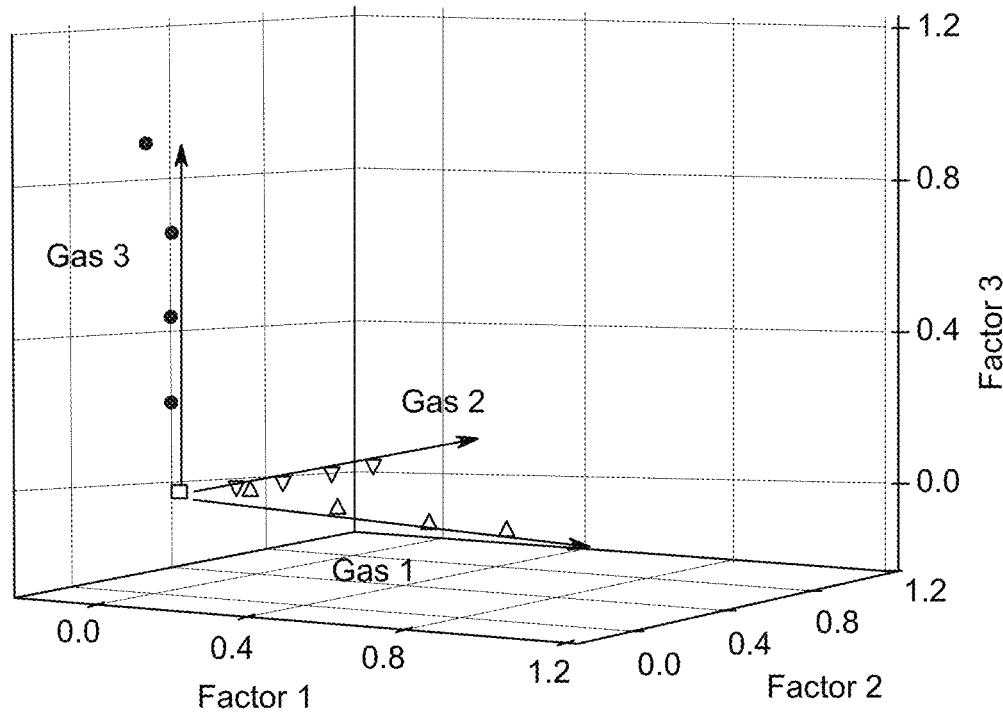
FIG. 56 depicts a plot of factor 1 vs factor 2 vs factor 3 of the built model that produces orthogonal response to three individual gases (gas 1 is acetylene C2H2, gas 2 is hydrogen H2, and methane CH4 is gas 3) with an improved linearity over PCA.

FIG. 56 depicts a plot of factor 1 versus factor 2 and versus factor 3 of another built model using a multivariate technique that is different from PCA. This plot illustrates the ability to produce orthogonal response to different individual gases such as gas 1, gas 2, and gas 3 with an improved linearity over PCA.

In one embodiment, a method includes measuring an electrical response of a sensing material in a gas sensor probe assembly while the gas sensor probe assembly is in an OFF state, determining an aging effect of the gas sensor probe assembly based on the electrical response of the sensing material in the gas sensor probe assembly while the gas sensor probe assembly is in the OFF state, measuring an electrical response of the sensing material in the gas sensor probe assembly while the sensing material is exposed to a fluid under examination and while the gas sensor probe assembly is in an ON state, and correcting the electrical response of the sensing material in the gas sensor probe assembly that is measured while the gas sensor probe assembly is in the ON state using the aging effect of the gas sensor probe assembly.

Optionally, the electrical response that is measured while the gas sensor probe assembly is in the ON state represents an amount of at least one analyte gas that is dissolved in an insulating oil of an electrical transformer.

Optionally, measuring the electrical response of the sensing material in the gas sensor probe assembly while the gas sensor probe assembly is in the OFF state occurs for a time period that is at least ten times longer than measuring the electrical response of the sensing material in the gas sensor probe assembly while the sensing material is exposed to the insulating oil and while the gas sensor probe assembly is in the ON state.

Optionally, the electrical response that is measured while the gas sensor probe assembly is in the ON state and that is corrected using the aging effect quantifies an amount of one or more of hydrogen, carbon monoxide, or a hydrocarbon gas in the fluid under examination.

Optionally, the gas sensor probe assembly measures the electrical response in the ON state by heating the sensing material and the gas sensor probe assembly measures the electrical response in the OFF state by not heating the sensing material.

Optionally, the electrical response that is measured while the gas sensor probe assembly is in the OFF state is an impedance response and the electrical response that is measured while the gas sensor probe assembly is in the ON state is a resistance response.

Optionally, the electrical response that is measured while the gas sensor probe assembly is in the OFF state is a resistance response and the electrical response that is measured while the gas sensor probe assembly is in the ON state is an impedance response.

Optionally, the electrical response that is measured while the gas sensor probe assembly is in the OFF state and the electrical response that is measured while the gas sensor probe assembly is in the ON state is an impedance response.

Optionally, the electrical response that is measured while the gas sensor probe assembly is in the OFF state and the electrical response that is measured while the gas sensor probe assembly is in the ON state is a resistance response.

Optionally, the electrical response of the gas probe sensor assembly is measured while in the OFF state and the electrical response of the gas probe sensor assembly is measured while in the ON state at different frequencies.

Optionally, correcting the electrical response that is measured while the gas sensor probe assembly is in the ON state uses the aging effect of the gas sensor probe assembly and one or more transfer functions associated with one or more analytes of interest.

In one embodiment, a locomotive system is provided that includes a platform, plural wheel-axle sets operably coupled to the platform, a reservoir attached to the platform and configured to hold a fluid, and a resonant sensor probe assembly coupled to the reservoir. The sensor probe assembly includes a substrate formed from one or more dielectric materials and free-standing electrodes coupled with the substrate. The free-standing electrodes are configured to be placed into the fluid, to generate an electric field between the free-standing electrodes, and to measure an impedance response of the sensor to the fluid between the electrodes.

Optionally, the free-standing electrodes are not directly mounted on the substrate. The free-standing electrodes may not be disposed within a footprint of the substrate. The free-standing electrodes may be configured to be placed into the fluid and to measure the impedance response of the sensor to the fluid without the substrate being placed into the fluid. The free-standing electrodes may include opposing planar plates positioned to receive at least some of the fluid between the plates. The free-standing electrodes can include an inner tube electrode disposed within and spaced apart from an outer tube electrode.

In one embodiment, a method for monitoring a health of equipment lubricant of a locomotive system is provided. The method includes monitoring previous operational conditions of a locomotive engine of the locomotive system that operates using fuel and a lubricant, identifying one or more of an impurity content of the fuel supplied to the locomotive engine or an elapsed time since a previous addition of additional lubricant to the lubricant in the locomotive engine, and determining whether a change of the lubricant is required prior to continued operation of the locomotive engine based on the previous operational conditions and the one or more of the impurity content of the fuel or the elapsed time since the previous addition of the additional lubricant to the lubricant in the locomotive engine.

Optionally, the method includes identifying the impurity content of the fuel and the impurity content is an amount of sulfur in the fuel. The method may include both identifying the impurity content of the fuel and the elapsed time since the previous addition of the additional lubricant and determining whether the change of the lubricant is required is based on the previous operational conditions, the impurity content of the fuel, and the elapsed time since the previous addition of the additional lubricant. The previous operational conditions can include one or more of an elapsed operating time of the locomotive engine, an operating temperature of the locomotive engine, or an ambient temperature in which the locomotive engine operated.

The method also can include creating or updating a digital twin of the locomotive engine based on the previous operational conditions of the locomotive engine and forecasting upcoming operational conditions of the locomotive engine. Determining whether the change of the lubricant is required prior to the continued operation of the locomotive engine can be based on the previous operational conditions, the one or more of the impurity content of the fuel or the elapsed time since the previous addition of the additional lubricant to the lubricant in the locomotive engine, the digital twin of the locomotive engine, and the upcoming operational conditions of the locomotive engine that are forecasted.

The method optionally can include changing the lubricant in the locomotive engine based on determining that the change in the lubricant is required. Determining whether the change of the lubricant is required can involve delaying the change of the lubricant beyond a previously scheduled maintenance of the locomotive engine that involves changing the lubricant.

In one embodiment, a locomotive system includes a platform, plural wheel-axle sets operably coupled to the platform, and a reservoir attached to the platform. The reservoir is configured to hold a fluid. The locomotive system also can include a sensor probe assembly having a substrate formed from one or more dielectric materials and free-standing electrodes coupled with the substrate and configured to be placed into the fluid, to generate an electric field between the electrodes, and to measure an electric response of the sensor to the fluid between the electrodes. The locomotive system also includes a controller configured to determine the electric response of the sensor while the sensor is not generating the electric field between the electrodes and to determine the electric response of the sensor while the sensor is generating the electric field between the electrodes. The controller also is configured to determine an aging effect of the sensor based on the electric response that is measured while the sensor is not generating the electric field between the electrodes. The controller is configured to correct the electric response of the sensor that is measured while the sensor is generating the electric field between the electrodes using the aging effect that is determined.

Optionally, the electric response that is measured while the sensor is generating the electric field between the electrodes represents an amount of at least one analyte gas that is dissolved in an insulating oil of an electrical transformer onboard the platform. The sensor can be configured to measure the electric response of the sensor while the sensor is not generating the electric field occurs for a time period that is longer than the sensor measures the electric response while the sensor is not generating the electric field between the electrodes. The sensor can be configured to measure the electric response while the sensor is generating the electric field between the electrodes and that is corrected using the aging effect quantifies an amount of one or more of hydrogen, carbon monoxide, or a hydrocarbon gas in the fluid.

The controller can be configured to direct one or more heating elements to heat the sensor while the sensor measures the electric response. The sensor can be configured to measure an impedance response of the sensor while the sensor is not generating the electric field between the electrodes, and wherein the electrical response that is measured while the gas sensor probe assembly is in the ON state is a resistance response. The sensor can be configured to measure the electric response while the sensor is not generating the electric field between the electrodes as a resistance response of the sensor, and the sensor can be configured to measure the electric response while the sensor is generating the electric field between the electrodes as an impedance response.

As used herein, the terms "module", "system," "device," "circuit," or "unit," may include a hardware and/or software system and circuitry that operates to perform one or more functions. For example, a module, unit, device, circuit, or system may include a computer processor, controller, or other logic-based device that performs operations based on instructions stored on a tangible and non-transitory computer readable storage medium, such as a computer memory. Alternatively, a module, unit, device, circuit, or system may include a hard-wired device that performs operations based on hard-wired logic and circuitry of the device. The modules, units, circuits, or systems shown in the attached figures may represent the hardware and circuitry that operates based on software or hardwired instructions, the software that directs hardware to perform the operations, or a combination thereof. The modules, systems, devices, circuits, or units can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, including the best mode, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general-purpose signal processor, microcontroller, random access memory, hard disk, or the like). Similarly, the programs may be stand alone programs, may be incorporated as subroutines in an operating system, may be functions in an installed software package, or the like. The various embodiments are not limited to the arrangements and instrumentality shown in the drawings.

As used herein, an element or step recited in the singular and proceeded with the word "a" or "an" should be understood as not excluding plural of said elements or operations, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

What is claimed is:

1. A resonant sensor probe assembly comprising:
   a substrate formed from one or more dielectric materials;
   free-standing electrodes coupled with the substrate, the free-standing electrodes configured to be placed into a fluid, and to generate an electric field between the free-standing electrodes; and
   a controller configured to measure an impedance response of the sensor probe assembly to the fluid between the electrodes responsive to generation of the electric field between the free-standing electrodes.

2. The resonant sensor probe assembly of claim 1, wherein the free-standing electrodes are not directly mounted on the substrate.

3. The resonant sensor probe assembly of claim 1, wherein the free-standing electrodes are not disposed within a footprint of the substrate.

4. The resonant sensor probe assembly of claim 1, wherein the free-standing electrodes are configured to be placed into the fluid and the controller is configured to measure the impedance response of the sensor probe assembly to the fluid while the substrate is outside of the fluid.

5. The resonant sensor probe assembly of claim 1, wherein the free-standing electrodes include opposing planar plates positioned to receive at least some of the fluid between the plates.

6. The resonant sensor probe assembly of claim 1, wherein the free-standing electrodes include an inner tube electrode disposed within and spaced apart from an outer tube electrode.

7. A method comprising:
monitoring previous operational conditions of a powered system that operates using a fuel and a lubricant;
measuring one or more of an impurity content of the fuel supplied to the powered system or an elapsed time since a previous addition of additional lubricant to the lubricant in the powered system; and
controlling a change of the lubricant prior to continued operation of the powered system based on the previous operational conditions and the one or more of the impurity content of the fuel or the elapsed time since the previous addition of the additional lubricant to the lubricant in the powered system.

8. The method of claim 7, wherein the method includes measuring the impurity content of the fuel and the impurity content is an amount of sulfur in the fuel.

9. The method of claim 7, wherein the method includes both measuring the impurity content of the fuel and the elapsed time since the previous addition of the additional lubricant, and
wherein controlling the change of the lubricant is based on the previous operational conditions, the impurity content of the fuel, and the elapsed time since the previous addition of the additional lubricant.

10. The method of claim 7, wherein the previous operational conditions include one or more of an elapsed operating time of the powered system, an operating temperature of the powered system, or an ambient temperature in which the powered system operated.

11. The method of claim 7, further comprising:
creating or updating a digital twin of the powered system based on the previous operational conditions of the powered system; and
forecasting upcoming operational conditions of the powered system,
wherein determining whether the change of the lubricant is required prior to the continued operation of the powered system is based on the previous operational conditions, the one or more of the impurity content of the fuel or the elapsed time since the previous addition of the additional lubricant to the lubricant in the powered system, the digital twin of the powered system, and the upcoming operational conditions of the powered system that are forecasted.

12. The method of claim 7, further comprising changing the lubricant in the powered system based on determining that the change in the lubricant is required.

13. The method of claim 7, wherein determining whether the change of the lubricant is required involves delaying the change of the lubricant beyond a previously scheduled maintenance of the powered system that involves changing the lubricant.

14. A system comprising:
a sensor probe assembly having a substrate formed from one or more dielectric materials and free-standing electrodes coupled with the substrate and configured to be placed into a fluid, the free-standing electrodes configured to generate an electric field between the free-standing electrodes; and
a controller configured to measure an electric response of the sensor probe assembly to the fluid between the electrodes and to determine the electric response of the sensor probe assembly while the sensor is not generating the electric field between the electrodes, the controller configured to determine the electric response of the sensor probe assembly while the sensor probe assembly is generating the electric field between the electrodes, the controller also configured to determine an aging effect of the sensor probe assembly based on the electric response that is measured while the sensor probe assembly is not generating the electric field between the electrodes,
wherein the controller is configured to correct the electric response of the sensor probe assembly that is measured while the sensor probe assembly is generating the electric field between the electrodes using the aging effect that is determined.

15. The system of claim 14, wherein the electric response that is measured while the sensor probe assembly is generating the electric field between the electrodes represents an amount of at least one analyte gas that is dissolved in an insulating oil of an electrical transformer.

16. The system of claim 14, wherein the sensor probe assembly is configured to measure the electric response of the sensor probe assembly while the sensor probe assembly is not generating the electric field occurs for a time period that is longer than the sensor probe assembly measures the electric response while the sensor probe assembly is not generating the electric field between the electrodes.

17. The system of claim 14, wherein the sensor probe assembly is configured to measure the electric response while the sensor probe assembly is generating the electric field between the electrodes and that is corrected using the aging effect quantifies an amount of one or more of hydrogen, carbon monoxide, or a hydrocarbon gas in the fluid.

18. The system of claim 14, wherein the controller is configured to direct one or more heating elements to heat the sensor probe assembly while the sensor probe assembly measures the electric response.

19. The system of claim 14, wherein the sensor probe assembly is configured to measure an impedance response of the sensor probe assembly while the sensor probe assembly is not generating the electric field between the electrodes, and wherein the electrical response that is measured while the sensor probe assembly is in an on state is a resistance response.

20. The system of claim 14, wherein the sensor probe assembly is configured to measure the electric response while the sensor probe assembly is not generating the electric field between the electrodes as a resistance response of the sensor probe assembly, and the sensor probe assembly is configured to measure the electric response while the sensor probe assembly is generating the electric field between the electrodes as an impedance response.

* * * * *